US012577620B2

(12) United States Patent
Spira et al.

(10) Patent No.: US 12,577,620 B2
(45) Date of Patent: Mar. 17, 2026

(54) NASAL EPITHELIUM GENE EXPRESSION SIGNATURE AND CLASSIFIER FOR THE PREDICTION OF LUNG CANCER

(71) Applicant: Trustees of Boston University, Boston, MA (US)

(72) Inventors: Avrum Spira, Newton, MA (US); Marc E. Lenburg, Brookline, MA (US); Joseph Perez-Rogers, San Mateo, CA (US); Christina Anderlind, Newton, MA (US)

(73) Assignee: Trustees of Boston University, Boston, MA (US)

( * ) Notice: Subject to any disclaimer, the term of this patent is extended or adjusted under 35 U.S.C. 154(b) by 997 days.

(21) Appl. No.: 17/397,905

(22) Filed: Aug. 9, 2021

(65) Prior Publication Data

US 2021/0381062 A1 Dec. 9, 2021

Related U.S. Application Data

(63) Continuation of application No. 16/300,947, filed as application No. PCT/US2017/032517 on May 12, 2017, now abandoned.

(60) Provisional application No. 62/335,391, filed on May 12, 2016.

(51) Int. Cl.
| | |
|---|---|
| *C12Q 1/6886* | (2018.01) |
| *C12Q 1/68* | (2018.01) |
| *G01N 33/53* | (2006.01) |
| *G01N 33/574* | (2006.01) |

(52) U.S. Cl.
CPC ............. *C12Q 1/6886* (2013.01); *C12Q 1/68* (2013.01); *G01N 33/53* (2013.01); *G01N 33/574* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,640,268 | A | 2/1972 | Davis |
| 4,641,662 | A | 2/1987 | Jaicks |
| 4,800,896 | A | 1/1989 | Jalowayski |
| 5,422,273 | A | 6/1995 | Garrison et al. |
| 5,440,942 | A | 8/1995 | Hubbard |
| 5,477,863 | A | 12/1995 | Grant |
| 5,726,060 | A | 3/1998 | Bridges |
| 5,795,782 | A | 8/1998 | Church et al. |
| 5,876,978 | A | 3/1999 | Willey et al. |
| 6,085,907 | A | 7/2000 | Hochmeister et al. |
| 6,667,154 | B1 | 12/2003 | Wang et al. |
| 6,676,609 | B1 | 1/2004 | Rutenberg et al. |
| 6,746,846 | B1 | 6/2004 | Wang et al. |
| 10,927,417 | B2 | 2/2021 | Beane-Ebel et al. |
| 2002/0081612 | A1 | 6/2002 | Katz et al. |
| 2002/0094547 | A1 | 7/2002 | Burstein |
| 2002/0160388 | A1 | 10/2002 | Macina et al. |
| 2003/0104499 | A1 | 6/2003 | Pressman et al. |
| 2003/0186248 | A1 | 10/2003 | Erlander et al. |
| 2004/0005294 | A1 | 1/2004 | Lee |
| 2004/0009489 | A1 | 1/2004 | Golub et al. |
| 2004/0063120 | A1 | 4/2004 | Beer et al. |
| 2004/0197785 | A1 | 10/2004 | Willey et al. |
| 2004/0241725 | A1 | 12/2004 | Xiao et al. |
| 2004/0241728 | A1 | 12/2004 | Liew |
| 2005/0260586 | A1 | 11/2005 | Demuth et al. |
| 2005/0266409 | A1 | 12/2005 | Brown et al. |
| 2006/0127928 | A1 | 6/2006 | Bacus et al. |
| 2006/0140960 | A1 | 6/2006 | Wang et al. |
| 2006/0154278 | A1 | 7/2006 | Brody et al. |
| 2006/0183144 | A1 | 8/2006 | Willey et al. |
| 2006/0188909 | A1 | 8/2006 | Willey et al. |
| 2006/0190192 | A1 | 8/2006 | Willey et al. |
| 2006/0194216 | A1 | 8/2006 | Willey et al. |
| 2007/0092891 | A1 | 4/2007 | Willey et al. |
| 2007/0092892 | A1 | 4/2007 | Willey et al. |
| 2007/0092893 | A1 | 4/2007 | Willey et al. |
| 2007/0148650 | A1 | 6/2007 | Brody et al. |

(Continued)

FOREIGN PATENT DOCUMENTS

| | | |
|---|---|---|
| CN | 1688582 A | 10/2005 |
| DE | 10219117 C1 | 10/2003 |

(Continued)

OTHER PUBLICATIONS

Han, Seon-Sook, et al. "RNA sequencing identifies novel markers of non-small cell lung cancer." Lung Cancer 84.3 (2014): 229-235.*
Collins, Lauren G., et al. "Lung cancer: diagnosis and management." American family physician 75.1 (2007): 56-63.*
Non-Final Office Action for U.S. Appl. No. 16/579,798 mailed Jun. 27, 2023.
Whitehead, et al., "Variation in tissue-specific gene expression among natural populations," Genome Biology, 6:R13, 2005.
Notice of Allowance for U.S. Appl. No. 16/579,798 mailed Dec. 19, 2023.
Abrahamson, et al., Cystatins. Biochem. Soc. Symp. 70: 179-199 (2003).

(Continued)

*Primary Examiner* — G. Steven Vanni
(74) *Attorney, Agent, or Firm* — Morse, Barnes-Brown & Pendleton, P.C.; Lisa M. Warren, Esq.; Erin E. Bryan, Esq.

(57) ABSTRACT

This application provides assays and methods for diagnosis and prognosis of lung cancer using expression analysis of one or more genes from a biological sample comprising nasal epithelial cells. The assays and methods are non-invasive and accurately detect the presence or absence of lung cancer relative to, for example, more invasive techniques, such as bronchoscopy. Similarly, the assays and methods described provide non-invasive ways of accurately identifying the smoking history of a subject.

23 Claims, 6 Drawing Sheets
(3 of 6 Drawing Sheet(s) Filed in Color)

(56) References Cited

U.S. PATENT DOCUMENTS

| 2009/0061454 A1 | 3/2009 | Brody et al. |
|---|---|---|
| 2009/0186951 A1 | 7/2009 | Brody et al. |
| 2009/0246779 A1 | 10/2009 | Rabinovitch et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2011/0053158 A1 | 3/2011 | Mambo et al. |
| 2011/0190150 A1 | 8/2011 | Brody et al. |
| 2011/0217717 A1 | 9/2011 | Brody et al. |
| 2012/0041686 A1 | 2/2012 | Brody et al. |
| 2012/0190567 A1 | 7/2012 | Brody et al. |
| 2012/0288860 A1 | 11/2012 | Van Hoek et al. |
| 2012/0322673 A1 | 12/2012 | Brody et al. |
| 2013/0023437 A1 | 1/2013 | Brody et al. |
| 2013/0303826 A1 | 11/2013 | Jurisica et al. |
| 2014/0378425 A1 | 12/2014 | Wilde et al. |
| 2015/0080243 A1 | 3/2015 | Whitney et al. |
| 2015/0088430 A1 | 3/2015 | Whitney |
| 2015/0152474 A1 | 6/2015 | Pawlowski et al. |
| 2015/0232945 A1 | 8/2015 | Brody et al. |
| 2015/0354008 A1 | 12/2015 | Brody et al. |
| 2016/0024583 A1 | 1/2016 | Whitney et al. |
| 2016/0130656 A1 | 5/2016 | Whitney et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2018/0171418 A1 | 6/2018 | Brody et al. |
| 2023/0235401 A1 | 7/2023 | Brody et al. |

FOREIGN PATENT DOCUMENTS

| WO | WO-1999/060160 A1 | 11/1999 |
|---|---|---|
| WO | WO-2000/006780 A1 | 2/2000 |
| WO | WO-2000/035473 A2 | 6/2000 |
| WO | WO-2001/028428 A1 | 4/2001 |
| WO | WO-2002/006791 A2 | 1/2002 |
| WO | WO-02/44331 A2 | 6/2002 |
| WO | WO-2002/072866 A2 | 9/2002 |
| WO | WO-2002/086443 A2 | 10/2002 |
| WO | WO-2003/015613 A2 | 2/2003 |
| WO | WO-2003/029273 A2 | 4/2003 |
| WO | WO-03/040317 A2 | 5/2003 |
| WO | WO-2003/040325 A2 | 5/2003 |
| WO | WO-2003/062389 A2 | 7/2003 |
| WO | WO-2004/005891 A2 | 1/2004 |
| WO | WO-2004/029055 A1 | 4/2004 |
| WO | WO-2004/091511 A2 | 10/2004 |
| WO | WO-2004/111197 A2 | 12/2004 |
| WO | WO-2005/000098 A2 | 1/2005 |
| WO | WO-2005/020784 A2 | 3/2005 |
| WO | WO-2005/047451 A2 | 5/2005 |
| WO | WO-2006/056080 A1 | 6/2006 |
| WO | WO-2006/113467 A3 | 4/2007 |
| WO | WO-2007/103541 A2 | 9/2007 |
| WO | WO-2009/039457 A2 | 3/2009 |
| WO | WO-2009/121070 A1 | 10/2009 |
| WO | WO-2010/054233 A1 | 5/2010 |
| WO | WO-2013/033640 A1 | 3/2013 |
| WO | WO-2013/049152 A2 | 4/2013 |
| WO | WO-2013/163568 A2 | 10/2013 |
| WO | WO-2013/177060 A2 | 11/2013 |
| WO | WO-2014/144564 A2 | 9/2014 |
| WO | WO-2014/186036 A1 | 11/2014 |
| WO | WO-2016/011068 A1 | 1/2016 |
| WO | WO-2017/197335 A1 | 11/2017 |
| WO | WO-2018/009915 A1 | 1/2018 |
| WO | WO-2018/048960 A1 | 3/2018 |

OTHER PUBLICATIONS

Anderson, et al., National Vital Statistics Report; 52(9): 1-88 (Nov. 7, 2003).

Anthonisen, et al., Effects of Smoking Intervention and the Use of an Inhaled Anticholinergic Bronchodilator on the Rate of Decline of FEV1. JAMA; 272(19):1497-1505 (Nov. 16, 1994).

Beane, et al., A Prediction Model for Lung Cancer Diagnosis that Integrates Genomic and Clinical Features, Cancer Prev Res 2008, 1:56-64 (2008).

Beane, et al., Reversible and permanent effects of tobacco smoke exposure on airway epithelial gene expression. Genome Biology 2007, 8:R201 (Sep. 25, 2007).

Beer, et al., Gene-expression profiles predict survival of patients with lung adenocarcinoma. Nature Medicine, 8: 816-824 (2002).

Belinksky, et al., Aberrant promoter methylation in bronchial epithelium and sputum from current and former smokers. Cancer Res., 62(8): 2370-7 (2002).

Berman, Jeffrey S, Abstract Immunopathology of the nasal mucosa in sarcoidosis National Institutes of Health Grant No. 1 R21 HL077498-01 (Funding Start Date Sep. 15, 2004).

Beum, et al., Epidermal Growth Factor Downregulates Core 2 Enzymes in a Human Airway Adenocarcinoma Cell Line. Am. J. Respir. Cell Mol. Biol., 29:48-56 (2003).

Bhattacharjee, et al., Classification of human lung carcinoma by mRNA expression profiling reveals distinct adenocarcinoma subclasses. Proc Natl Acad Sci USA, 98(24): 13790-5 (Nov. 20, 2001).

Bild, et al., Oncogenic pathway signatures in human cancers as a guide to targeted therapies. Nature, 439: 353-357 (2006).

Chari, et al., Effect of active smoking on the human bronchial epithelium transcriptome. BMC Genomics, 8:297 (Aug. 29, 2007).

Clark, A., et al., "Altered Protein Kinase C (PKC) Isoforms in Non-Small Cell Lung Cancer Cells: PKCdelta Promotes Cellular Survival and Chemotherapeutic Resistance," Cancer Research, 63(4): 780-786 (2003).

Crawford, et al., Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).

Cummings, SR. et al., Estimating the probability of malignancy in solitary pulmonary nodules. A Bayesian approach, Am Rev Respir Dis 1986;134:449-52 (1986).

Demeo, et al., The SERPINE2 gene is associated with chronic obstructive pulmonary disease. Am J Hum Genet., 78(2): 253-264 (Feb. 2006).

Denis, et al., RING3 Kinase Transactivates Promoters of Cell Cycle Regulatory Genes through E2F1 Cell. Growth Differ; 11: 417-424 (Aug. 2000).

Doll, R. et al., Mortality in relation to smoking: 40 years' observations on male British doctors. BMJ; 309:901-911 (Oct. 8, 1994).

Ebbert, et al., Lung Cancer Risk Reduction After Smoking Cessation: Observations From a Prospective Cohort of Women. J Clin Oncol; 21(5):921-926 (Mar. 1, 2003).

Fahy, JV. Remodeling of the Airway Epithelium in Asthma. Am. J. Respir. Crit. Care Med. 164:S46-S51 (2001).

Freeman, et al., DNA from Buccal Swabs Recruited by Mail: Evaluation of Storage Effects on Long-term Stability and Suitability for Multiplex Polymerase Chain Reaction Genotyping, Behavior Genetics, 33: 67 (2003).

Garber, et al., Diversity of gene expression in adenocarcinoma of the lung. PNAS, 98(24): 13784-13789 (Nov. 20, 2001).

Garcia-Closas, Collection of Genomic DNA from Adults in Epidemiological Studies by Buccal Cytobrush and Mouthwash, Cancer Epidemiology, Biomarkers and Prevention, 10: 687-696, (2001).

Gebel, et al., Gene expression profiling in respiratory tissues from rats exposed to mainstream cigarette smoke. Carcinogenesis, 25(2): 169-178 (2004).

Golub, et al., Molecular classification of cancer: Class discovery and class prediction by gene expression monitoring, Science, American Association for the Advancement of Science, 286:5439 (Oct. 15, 1999).

Greenlee, et al., Cancer Statistics, 2001. CA Cancer J Clin; 51(1):15-36 (2001).

Gurney, JW. Determining the likelihood of malignancy in solitary pulmonary nodules with Bayesian analysis, Part 1, Theory. Radiology 1993;186:405-13 (2005).

(56) References Cited

OTHER PUBLICATIONS

Hackett, et al., Variability of antioxidant-related gene expression in the airway epithelium of cigarette smokers. Am J Respir Cell Mol Biol., 29: 331-43 (2003).

Hecht, SS., Tobacco carcinogens, their biomarkers and tobacco-induced cancer. Nature Review Cancer; 3:733-744 (Oct. 2003).

Jang, et al., Activation of melanoma antigen tumor antigens occurs early in lung carcinogenesis. Cancer Research 61: 7959-7963 (2001).

Kanner, et al., Effects of randomized assignment to a smoking cessation intervention and changes in smoking habits on respiratory symptoms in smokers with early chronic obstructive pulmonary disease: the lung health study. American Journal of Medicine; 106:410-416 (1999).

Kao, et al., Tumor-associated Antigen L6 and the Invasion of Human Lung Cancer Cells. Clin Cancer Res. 9:2807-2816 (Jul. 2003).

Katz, et al., Automated detection of genetic abnormalities combined with cytology in sputum is a sensitive predictor of lung cancer, Modern Pathology;21:950-960 (2008).

Kazemi-Noureini, et al., Differential gene expression between squamous cell carcinoma of esophageus and its normal epithelium; altered pattern of mal, akr1c2, and rab11a expression. World J Gastroenterol, 10(12): 1716-1721 (2004).

Kitahara, et al. Alternations of Gene Expression during Colorectal Carcinogenesis; Revealed by cDNA Microarrays after Laser-Capture Microdissection of Tumor Tissues and Normal Epithelia. Cancer Research, 61: 3544-3549 (May 1, 2001).

Lander, et al., Initial sequencing and analysis of the human genome. Nature, 409: 860-921 (Feb. 15, 2001).

Li, L., Survival prediction of diffuse large-B-cell lymphoma based on both clinical and gene expression information, Bioinformatics 2006; 22:466-71 (2006).

Liao, et al., Expression and significance of PTEN/PI3K signal transduction-related proteins in non-small cell lung cancer, Ai Zheng 25: 10, p. 1238-42. Abstract (2006).

Liu et al., Effects of physiological versus pharmacological ß-carotene supplementation on cell proliferation and histopathological changes in the lungs of cigarette smoke-exposed ferrets. Carcinogenesis, 21: 2245-2253 (2000).

Mannino, DM. et al., Low lung function and incident lung cancer in the United States: data From the First National Health and Nutrition Examination Survey follow-up, Arch Intern Med. 163(12):1475-80 (2003).

Medical News: Targeted, Oral Agent Enzastaurin Shows Favorable Results in Late-Stage Lung Cancer. (Jun. 11, 2007), Retrieved from the Internet <URL: <http://www.medicalnewstoday.com/articles/73761.php>>.

Michalczyk, et al., Fresh and cultured buccal cells as a source of mRNA and protein for molecular analysis. Biotechniques. 37(2):262-4, 266-9 (2004).

Miklos, et al., Microarray reality checks in the context of a complex disease. Nature Biotechnology, 22:5 (May 2005).

Miura, et al., Laser capture microdissection and microarray expression analysis of lung adenocarcinoma reveals tobacco smoking- and prognosis-related molecular profiles. Cancer Res., 62(11): 3244-50 (Jun. 1, 2002).

Mongiat, et al., Fibroblast Growth Factor-binding Protein Is a Novel Partner for Perlecan Protein Core. The Journal of Biological Chemistry; 276(13):10263-10271 (Mar. 30, 2001).

Neubauer, et al., Cure of Helicobacter pylori Infection and Duration of Remission of Low-Grade Gastric Mucosa-Associated Lymphoid Tissue Lymphoma. J. Natl. Cancer Inst., 89(18): 1350-1378 (Sep. 17, 1997).

Okudela, K., et al., "K-ras Gene Mutation Enhances Motility of Immortalized Airway Cells and Lung Adenocarcinoma Cells Via Akt Activation: Possible Contribution to Non-Invasive Expansion of Lung Adenocarcinoma," The American Journal of Pathology, 164(1): 91-100 (2004).

Pittman, J. et al., Integrated modeling of clinical and gene expression information for personalized prediction of disease outcomes, Proc Natl Acad Sci U S A 2004; 101:8431-6 (2004).

Potti et al., A Genomic Strategy to Refine Prognosis in Early-Stage Non Small-Cell Lung Cancer, The New England Journal of Medicine 2006; 335(6):570-580 (2006).

Powell, et al., Patterns of allelic loss differ in lung adenocarcinomas of smokers and nonsmokers. Lung Cancer, 39(1): 23-29 (2003).

Powell, et al., Gene expression in lung adenocarcinomas of smokers and nonsmokers. American Journal of Respiratory Cell and Molecular Biology, 29: 157-162 (Aug. 2003).

Proctor RN., Tobacco and the global lung cancer epidemic. Nature Reviews Cancer, 1: 82-86 (Oct. 2001).

Rusznak, et al., Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).

Saheki, et al., Pathogenesis and pathophysiology of citrin (a mitochondrial aspartate glutamate carrier) deficiency. Metabolic Brain Disease; 17(4):335-346 (Dec. 2002).

Schembri, Frank et al., MicroRNAs as modulators of smoking-induced gene expression changes in human airway epithelium, Proc Natl Acad Sci U S A, 106(7):2319-24 (Feb. 2009).

Shields, PG., Molecular epidemiology of lung cancer. Annals of Oncology, 10(5):S7-S11 (1999).

Shriver, et al., Sex-Specific Expression of Gastrin-Releasing Peptide Receptor: Relationship to Smoking History and Risk of Lung Cancer. J. Natl. Cancer Inst., 92: 24-33 (2000).

Spira, et al., Noninvasive method for obtaining RNA from buccal mucosa epithelial cells for gene expression profiling. Biotechniques, 36(3): 484-7 (2004).

Spira, et al., Effects of cigarette smoke on the human airway epithelial cell transcriptome, PNAS, 101: 27, p. 10143-10148 (Jul. 6, 2004).

Spira, et al., Airway epithelial gene expression in the diagnostic evaluation of smokers with suspect lung cancer. Nature Medicine 13: 361-366 (2007).

Spira, et al., Gene Expression Profiling of Human Lung Tissue from Smokers with Severe Emphysema. Am J Respir Cell Mol Biol., 31(6):601-10 (2004).

Spira, et al., Impact of cigarette smoke on the normal airway transcriptome. Chest. 125 (5 Suppl):115S (May 2004).

Spira, Avrum E., Abstract The airway transcriptome as a biomarker for lung cancer National Institutes of Health Grant No. 1 R21 CA106506-01 (Funding Start Date Aug. 9, 2005).

Spira, Avrum E., Abstract Airway gene expression in smokers: an early diagnostic biomarker for lung cancer National Institutes of Health Grant No. 1 R01 CA124640-01 (Funding Start Date May 1, 2007).

Spivack, et al., Gene-environment interaction signatures by quantitative mRNA profiling in exfoliated buccal mucosal cells, Cancer Research, 64: 18, p. 6805-6813 (2004).

Sridhar, et al. Smoking-induced gene expression changes in the bronchial airway are reflected in nasal and buccal epithelium. BMC Genomics, 9: 259 (May 2008).

Stephenson, AJ. et al., Integration of gene expression profiling and clinical variables to predict prostate carcinoma recurrence after radical prostatectomy, Cancer 2005; 104:290-8 (2005).

Stewart, JH. Lung Carcinoma in African Americans, A Review of the Current Literature. Cancer; 91(12): 2476-2482 (Jun. 15, 2001).

Swensen, SJ. et al., The probability of malignancy in solitary pulmonary nodules. Application to small radiologically indeterminate nodules, Arch Intern Med 1997; 157:849-55 (1997).

Swensen, SJ. et al., Abstract Solitary pulmonary nodules: clinical prediction model versus physicians, Mayo Clinic Proc 1999; 74:319-29 (1999).

Theocharis, et al., Metallothionein: a multifunctional protein from toxicity to cancer. Int Biol Markers, 18(3):162-169 (2003).

Thurston, SW. et al., Modeling lung cancer risk in case-control studies using a new dose metric of smoking, Cancer Epidemiol Biomarkers Prev 2005; 14(10): 2296-302 (2005).

(56) References Cited

OTHER PUBLICATIONS

Trunk, G. et al., The management and evaluation of the solitary pulmonary nodule, Chest 1974; 66:236-9 (1974).

Ung, YC. et al., Fluorodeoxyglucose positron emission tomography in the diagnosis and staging of lung cancer: a systematic review, J Nat'l Cancer Institute, 99(23): 1753-67 (2007).

Volm, et al., Prognostic significance of the expression of c-fos, c-jun and c-erbB-1 oncogene products in human squamous cell lung carcinomas. J Cancer Res Clin Oncol, 119: 507-510 (1993).

Wahidi, MM. et al., Evidence for the treatment of patients with pulmonary nodules: when is it lung cancer? ACCP evidence-based clinical practice guidelines 2nd Edition, Chest 2007; 132:94-107S (2007).

West, M., et al. Embracing the complexity of genomic data for personalized medicine, Genome Res 2006; 16:559-66 (2006).

Wistuba, et al., Molecular damage in the bronchial epithelium of current and former smokers. J Natl Cancer Inst., 89(18): 1366-73 (Sep. 17, 1997).

Wistuba, et al., High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).

Zeeberg, et al.. GoMiner: a resource for biological interpretation of genomic and proteomic data. Genome Biology, 4(4): R28.1-R28.8 (2003).

Zhang, et al. Comparison of smoking-induced gene expression on Affymetrix Exon and 3'-based expression arrays. Genome Inform. 18: 247-57 (2007).

Retracted in Jan. 2011—Potti, A., et al., "Genomic Signatures to Guide the Use of Chemotherapeutics," Nature Medicine, 12(11): 1294-1300 (2006). (Retracted in Jan. 2011—Potti, A., et al., "Genomic Signatures to Guide the Use of Chemotherapeutics," Nature Medicine, 12(11): 1294-1300 (2006).).

Ambion, Inc. "GeneAssist Pathway Atlas for P13K Signaling," Accessed from <http://www5.appliedbiosystems.com/tools/pathway/pathway_proteins.php?pathway=P13K> on May 3, 2011.

Arimura, et al. Elevated Serum β-Defensins Concentrations in Patients with Lung Cancer, *Anticancer Research*, 24: 4051-4058 (2004).

Baker, Stuart. "The Central Role of Receiver Operating Characteristic (ROC) Curves in Evaluating Tests for the Early Detection of Cancer," *Journal of the National Cancer Institute*, 95(7): 511-515 (2003).

Braakhuis, et al. "A Genetic Explanation of Slaughter's Concept of Field Cancerization Evidence and Clinical Implications," *Cancer Research*, 63: 1727-1730 (2003).

Chen, et al. "Discordant Protein and mRNA Expression in Lung Adenocarcinomas," *Molecular and Cellular Proteomics*, 1: 304-313 (2001).

Dauletbaev, et al. "Expression of Human Beta Defensin (HBD-1 and HBD-2) mRNA in Nasal Epithelia of Adult Cystic Fibrosis Patients, Healthy Individuals, and Individuals with Acute Cold," *Respiration*, 69:46-51 (2002).

Franklin, et al. "Widely Dispersed p53 Mutation in Respiratory Epithelium," *The Journal of Clinical Investigation*, 100(8): 2133-2137 (1997).

Hellmann, et al. "Gene Profiling of Cultured Human Bronchia Epithelial and Lung Cacinoma Cells," *Toxicological Sciences*, 61: 154-163 (2001).

Ikeda, et al. "Malignancy associated changes in bronchial epithelial cells and clinical application as a biomarker," *Lung Cancer*, 19(3): 161-166 (1998).

Kraft, et al. "Expression of epithelial markers in nocturnal asthma," *Journal of Allergy and Clinical Immunology*, 102(3): 376-381 (1998).

Liu, et al. "Quantitative Proteome Analysis Reveals Annexin A3 as a Novel Biomarker in Lung Adenocarcinoma," *Journal of Pathology*, 217: 54-64 (2009).

Reynolds, et al. "Pre-protachykinin-A mRNA is increased in the airway epithelium of smokers with chronic bronchitis." *Respiratory*, 6:187-197 (2001).

Riise, et al. "Bronchial Brush Biopsies for Studies of Epithelial Inflammation in Stable Asthma and Nonobstructive Chronic Bronchitis," *European Respiratory Journal*, 9: 1665-1671 (1996).

Slonim, Donna. "From Patterns to Pathways: Gene Expression Data Analysis Comes of Age," *Nature Genetics Supplement*, 32: 502-508 (2002).

Takizawa, et al. "Increased expression of transforming growth factor-beta1 in small airway epithelium from tobacco smokers and patients with chronic obstructive pulmonary disease (COPD)," *American Journal of Respiratory and Critical Care Medicine*, 163:1476-1483 (2001).

Watters, et al. "Developing Gene Expression Signatures of Pathway Deregulation in Tumors," *Molecular Cancer Therapeutics*, 5: 2444-2449 (2006).

Ohtsuka, et al., "ADAM28 is overexpressed in human non-small cell lung carcinomas and correlates with cell proliferation and lymph node metastasis," *International Journal of Cancer*, 118(2): 263-273 (2006).

Hamilton and Sharp, "Diagnosis of lung cancer in primary care: a structured review," *Family Practice*, 21(6), 605-611 (2004).

Akita, et al., "Molecular Biology of Lung Cancer," *The Journal of the Japanese Respiratory Society*, 42(5): (2004).

Printout from database NCBI GEO accession No. GSE4115 [Online] NCB, dated Feb. 27, 2006.

Brody, Jerome S., Abstract "Airway epithelial gene expression in COPD" National Institutes of Health Grant No. 1 R01 HL071771-01 (Funding Start Date Sep. 30, 2002).

Bohula et al., "The Efficacy of Small Interfering RNAs Targeted to the Type 1 Insulin-like Growth Factor Receptor (IGF1R) Is Influenced by Secondary Structure in the IGF1R Transcript," The Journal of Biological Chemistry 278(18): 15991-15997 (2003).

Wardlaw, et al., "Effect of cigarette smoke on CYP1A1, CYP1A2 and CYP2B1/2 of nasal mucosae in F344 rats," Carcinogenesis 19(4): 655-662 (1998).

Lin, et al., "Effects of Dexamethasone on Acute Lung Injury Rat Cells Signal Transduction Systems ERK and PI3-K," Medical Journal of Chinese People's Liberation Army 6(31): 592-594 (2006).

Guajardo, et al., "Altered gene expression profiles in nasal respiratory epithelium reflect stable versus acute childhood asthma", J. Allergy Clin Immunol 115(2): 243-251 (2005).

Voynow, et al., "Mucin Gene Expression (MUC1, MUC2, and MUC5/5AC) in Nasal Epithelial Cells of Cystic Fibrosis, Allergic Rhinitis, and Normal Individuals", Lung 176: 345-354 (1998).

Shah et al., "SIEGE: Smoking Induced Epithelial Gene Expression Database", Nucleic Acids Research, 33: D573-D579 (2005).

Enard et al., "Intra- and Interspecific Variation in Primate Gene Expression Patterns", Science 296: 340-343 (2002).

Cheung, et al., "Natural variation in human gene expression assessed in lymphoblastoid cells", Nature Genetics, 33: 422-425 (2003).

Wu, Thomas D., "Analysing gene expression data from DNA microarrays to identify candidate genes", Journal of Pathology, 195:53-65 (2001).

Newton, et al., "On Differential Variability of Expression Ratios: Improving Statistical Inference about Gene Expression Changes from Microarray Data", Journal of Computational Biology, 8: 37-52 (2001).

Fritz, et al., "Nasal mucosal gene expression in patients with allergic rhinitis with and without nasal polyps", Journal of Allergy Clin. Immunol, 112(6): 1057-1063 (2003).

Lam, et al., "A Phase I Study of myo-Inositol for Lung Cancer Chemoprevention", Cancer Epidemiology, Biomarkers & Prevention 15(8): 1526-1531 (2006).

Peluso, et al., "Comparison of DNA adduct levels in nasal mucosa, lymphocytes and bronchial mucosa of cigarette smokers and interaction with metabolic gene polymorphisms", Carcinogenesis 25(12): 2459-2465 (2004).

Marinov, et al., "Targeting mTOR signaling in lung cancer", Critical Reviews in Oncology/Hematology 63: 172-182 (2007).

(56)  References Cited

OTHER PUBLICATIONS

Singhal, et al., "Alterations in Cell Cycle Genes in Early Stage Lung Adenocarcinoma Identified by Expression Profiling", Cancer Biology & Therapy 2(3): 291-299 (2003).

Zhang, et al., "Similarities and Differences Between Smoking-Related Gene Expression in Nasal and Bronchial Epithelium," *Physiol. Genomics, 41*:1-8, (2010).

Danel, et al., "Quantitative assessment of the epithelial and inflammatory cell populations in large airways of normal and individuals with cystic fibrosis," American Journal of Respiratory and Critical Care Medicine 153(1): 362-368 (1996).

Merriam-Webster.com (htpp://www.merriam-webster.com/dictionary/questionnaire, downloaded Oct. 26, 2013).

Tarca, et al., "Analysis of microarray experiments of gene expression profiling," American Journal of Obstetrics and Gynecology 195(2): 373-388 (2006).

May, "How many species are there on earth?" Science 241(4872): 1441-1449 (1988).

Benner, et al. "Evolution, language and analogy in functional genomics," Trends in Genetics 17(7): 414-418 (2001).

Modrek, et al., "Genome-wide detection of alternative splicing in expressed sequences of human genes," Nucleic Acids Research 29(13): 2850-2859 (2001).

Woenckhaus, et al., "Smoking and cancer-related gene expression in bronchial epithelium and non-small-cell lung cancers," The Journal of Pathology 210(2): 192-204 (2006).

Details for HG-U133A:202831_AT (<https://www.affymetrix.com/analysis/netaffx/fullrecord.affx?pk=HG-U133A:202831_AT>, downloaded Dec. 10, 2012).

Details for HG-U133A:210519_S_AT (<https://www.affymetrix.com/analysis/netaffx/fullrecord.affx?pk=HG-U133A:210519_S_AT> downloaded Dec. 10, 2012).

HG-U133a-207469_S_AT (https:www/affymetrix.com/analysis/netaffx/fullrecord.affx?pk=HG-U133A:207469_S_AT, downloaded Dec. 10, 2012.

HG-U133A:823_AT (<https://www.affymetrix.com/analysis/netaffx/fullrecord.affx?pk=HG-U133A:823_AT>, downloaded Dec. 10, 2012.

Demoly, et al., "c-fos Proto-oncogene Expression in Bronchial Biopsies of Asthmatics," American Journal of Respiratory Cell and Molecular Biology 7:128-133 (1992).

Hennessy, et al., "Exploiting the PI3K/AKT Pathway for Cancer Drug Discovery," Nature, vol. 4: 988-1004 (2005).

Langford, et al., "Is the Property of Being Positively Correlated Transitive," The American Statistician 55(4): 322-325 (2001).

Saal, et al., "Poor Prognosis in Carcinoma is Associated with A Gene Expression Signature of Aberrant PTEN Tumor Suppressor Pathway Activity," PNAS 104(18): 7564-7569 (2007).

Sotos, et al., "The Transitivity Misconception of Pearson's Correlation Coefficient," Statistics Education Research Journal 8(2): 33-55 (2009).

Thisted, Ronald A. "What is a P-value", Departments of Statistics and Health Studies, The University of Chicago, May 25, 1988.

Tichelaar, et al., "Increased Staining for Phospho-Akt, p65/RELA and cIAP-2 in Pre-neoplastic Human Bronchial Biopsies," BMC Cancer 5(155): 1-13 (2005).

Tsao, et al, "Increased Phospho-AKT (Ser473) Expression in Bronchial Dysplasia: Implications for Lunch Cancer Prevention Studies," Cancer, Epidemiology, Biomarkers & Prevention 12:660-664 (2003).

West, et al, "Rapid Akt Activation by Nicotine and Tobacco Carcinogen Modulates the Phenotype of Normal Human Airway Epithelial Cells," The Journal of Clinical Investigation 111(1): 81-90 (2003).

Hoshikawa, et al., "Hypoxia induces difference genes in the lungs of rats compared with mice," Physiol Genomics 12: 209-219 (2003).

Cheng, et al., "Reduced expression levels of nucleotide excision repair genes in; lung cancer: a case-control analysis," Carcinogenesis 21(8): 1527-1530 (2000).

Fielding, et al., "Heterogeneous Nuclear Ribonucleoprotein A2/B1 Up-Regulation in Bronchial Lavage Specimens: A Clinical Marker of Early Lung Cancer Detection," Clinical Cancer Research 5:4048-4052 (1999).

Yu-Rong, et al., "Tumor associated antigen L6 and the invasion of human lung cancer cells." Clinical Cancer Research 9(7): 2807-16 (2003).

Dempsey, et al., "Lung disease and PKCs," Pharmacological Research 55(6): 545-59 (2007).

MacKay et al., "Targeting the protein kinase C family: are we there yet?" Nature Reviews Cancer 7(7): 554-62 (2007).

Gustafson, et al., "Airway PI3K Pathway Activation Is an Early and Reversible Even in Lung Cancer Development," www.Science TransmlationMedicine.org <http://www.ScienceTransmlationMedicine.org> 2(26) (2010).

Fukumoto, et al., "Overexpression of the Aldo-Keto Reductase Family Protein AKR1B10 is Highly Correlated with Smokers' Non-Small Cell Lung Carcinomas," Clinical Cancer Research 11:1776-1786 (2005).

Whitehead et al., "Variation in tissue-specific gene expression among natural populations," Genome Biology 6(2):R13.1-R13.14 (2005).

Brambilla, et al., "Advances in Brief p53 Mutant Immunophenotype and Deregulation of p53 Transcription Pathway (Bc12, Bax, and Waft) in Precursor Bronchial Lesions of Lung Cancer1", *Clinical Cancer Research*, 4: 1609-1618 (1998).

Demuth, et al., "The gene expression index c-myc x E2F-1/p21 is highly predictive of malignant phenotype in human bronchial epithelial cells", *American Journal of Respiratory Cell and Molecular Biology*, 19: 18-24 (1998).

Hirsch, et al., "Early Detection of Lung Cancer: Clinical Perspectives of Recent Advances in Biology and Radiology 1", *Clinical Cancer Research*, 7: 5-22 (2001).

Lacroix, et al., "Sensitive detection of rare cancer cells in sputum and peripheral blood samples of patients with lung cancer by preproGRP-specific RT-PCR", *International Journal of Cancer*, 92(1): 1-8 (2001).

Willey, et al., "Quantitative RT-PCR Measurement of Cytochromes p450 1A1, 1B1, and; 2B7, Microsomal Epoxide Hydrolase, and NADPH Oxidoreductase Expression in Lung Cells of Smokers and Nonsmokers," Am. J. Respir. Cell Mol. Biol., 1997, 17:114-124.

Mollerup, et al., "Sex Differences in Lung CYP1A1 Expression and DNA Adduct Levels among Lung Cancer Patients," Cancer Research, 1999, 59: 3317-3320 (1999).

Saito-Hisaminato, "Genome-Wide Profiling of Gene Expression in 29 Normal Human Tissues with a cNDA Microarray," DNA Research, 2002, 9:35-45.

Details for HG-U133A:217291_At (CEACAM5) (https://www.affymetrix.com/analysis/netaffx/fullrecord.affx?pk=HG-U133A:217291_AT,; downloaded Apr. 22, 2016).

St. Croix, et al., "Genes Expressed in Human Tumor Endothelium," *Science*, 289:1197-1202, (Aug. 18, 2000).

Moller, et al., "Altered ratio of endothelin ETA- and ETB receptor mRNA in bronchial biopsies from patients with asthma and chronic airway obstruction," Eur. Journal of Pharmacology, 365:R1-R3, (1999).

Wojnarowski et al., "Cytokine expression in bronchial biopsies of cystic fibrosis patients with and without acute exacerbation," Eur. Respir. J., 14:1136-1144, (1999).

Anbazhagan, et al., "Classification of Small Cell Lung Cancer and Pulmonary Carcinoid by Gene Expression Profiles," *Cancer Research, 59*:5119-5122, (Oct. 15, 1999).

Chen, et al., "Up-regulations of Tumor Interleukin-8 Expression by Infiltrating Macrophages: Its Correlation with Tumor Angiogenesis and Patient Survival in Non-Small Cell Lung Cancer," *Clinical Cancer Research*: pp. 729-737, (Feb. 1, 2003).

Grepmeier, et al., "Deletions at Chromosome 2q and 12p are Early Frequent Molecular Alterations in Bronchial Epithelium and NSCLC of Long-Term Smokers." *Int J Oncol., 27*(2):481-8, (2005).

Khan, et al., "Classification and Diagnostic Prediction of Cancers Using Gene Expression Profiling and Artificial Neural Networks," *Nature Medicine, 7*(6):673-679, (Jun. 2001).

(56)        References Cited

OTHER PUBLICATIONS

Yoneda, et al., "Development of High-Density DNA Microarray Membrane for Profiling Smoke-and Hydrogen Peroxide-Induced Genes in a Human Bronchial Epithelial Cell Line," *American Journal of Respiratory and Critical Care Medicine, 164*:S86-S89, (2001).

Notterman, et al., "Tumor Biology and Microarray Analysis of Solid Tumors: Colorectal Cancer as a Model System," *Microarrays and Cancer Research*, Warrington et al.(eds.), Eaton Publishing, Westborough, MA, pp. xi-xvi, (2002).

Strausberg, et al., "Reading the Molecular Signatures of Cancer," *Microarrays and Cancer Research*, Warrington et al. (eds.), Eaton Publishing, Westborough, MA, pp. 81-111, (2002).

Zochbauer-Muller, et al., "5' CpG Island Methylation of the FHIT Gene is Correlated with Loss of Gene Expression in Lung and Breast," *Cancer Research, 61*:3581-3585, (May 2, 2001).

Cooper, "Gene Expression Studies in Lung Cancer," *The Molecular Genetics of Lung Cancer, pp. 167-186, (2005).*

Deng, et al., "Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase," *Cancer Chemother. Pharmacol., 54*:301-307, (2004).

Schulz, et al., "Activation of Bronchial Epithelial Cells in Smokers Without Airway Obstruction and Patients with COPD," *Chest, 125*(5):1706-1713, (May 2004).

Su, et al., "Molecular Classification of Human Carcinomas by Use of Gene Expression Signatures," *Cancer Research, 61*:7388-7393, (Oct. 15, 2001).

Yang, et al., "Reduction of Dihydrodiol Dehydrogenase Expression in Resected Hepatocellular Carcinoma," *Oncol. Rep., 10*(2):271-276, Abstract pp. 1-2 (2003).

Kuriakose, et al., "Selection and Validation of Differentially Expressed Genes in Head and Neck Cancer," CMLS, 61:1372-1383, (2004).

Sugita, et al., "Combined Use of Oligonucleotide and Tissue Microarrays Identifies Cancer/Testis Antigens as Biomarkers in Lung Carcinoma," Cancer Research, 62:3971-3979, (Jul. 15, 2002).

Vartiainen, et al., "Validation of Self-Reported Smoking by Serum Cotinine Measurement in a Community-Based Study," *J. Epidemiol Community Health, 56*:167-170, (2002).

Beane-Ebel, "Single-Cell RNA Sequencing of the Bronchial Epithelium in Smokers With Lung Cancer," U.S. Army Medical Research and Material Command. Jul. 1, 2016 [retrieved on Sep. 19, 2017]. Retrieved from the Internet at http://www.dtic.mil/dtic/tr/fulltext/u2/a624219.pdf.

Coleman, "Of Mouse and Man—What is the Value of the Mouse in Predicting Gene Expression in Humans?" Drug Discovery Today, 8(6):233-235, (Mar. 2003).

Durham, et al., "The Relationship Between COPD and Lung Cancer," Lung Cancer, 90:121-127, (2015).

Kocarnik, et al., "Replication of Associations Between GWAS SNPs and Melanoma Risk in the Population Architecture Using Genomics and Epidemiology (PAGE) Study," Journal of Investigative Dermatology, 134:2049-2052, (Feb. 27, 2014).

Ooi, et al., "Molecular Profiling of Premalignant Lesions in Lung Squamous Cell Carcinomas Identifies Mechanisms Involved in Stepwise Carcinogenesis," Cancer Prevention Research, 7(5):487-495, (Mar. 11, 2014).

Anonymous: "Bronchogenic carcinoma is a malignant neoplasm of the lung arising from the epithelium of the bronchus or bronchiole", Apr. 22, 2003 (Apr. 22, 2003), retrieved from the internet: URL:http://www.meddean.luc.edu/lumen/meded/medicine/pulmonar/pathms/path19.htm [retrieved on Feb. 13, 2019].

Brenner, Sydney, et al. "Gene expression analysis by massively parallel signature sequencing (MPSS) on microbead arrays." Nature biotechnology 18.6 (2000): 630.

Gerrein, J., et al., "/Poster Discussion Session/ Sunday, May 18 / 2:00-4:30 PM / Room 30 A-B (Upper Level) San A107 The Lung's Silver Lining: Airway and Alveolar Epithelial Biology Leveraging Gene Expression in the Bronchial Airway to Develop a Nasal Biomarker for Early Detection of Lung Cancer," retrieved from the Internet: URL:https://www.atsjournals.org/doi/pdf/10.1164/ajrccm-conference.2014.189.1_MeetingAbstract.A2362 (2014).

Chen, et al., "Expression of dihydrodiol dehydrogenase in the resected stage I non-small cell lung cancer," Oncology Reports, vol. 9, No. 3, May 1, 2002, pp. 515-519.

Hsu, et al., "Overexpression of dihydrodiol dehydrogenase as a prognostic maker of non-small cell lung cancer," Cancer Research vol. 6, No. 6, Mar. 15, 2001, pp. 2727-2731.

Shibuya, Kiyoshi, et al. "Increased telomerase activity and elevated hTERT mRNA expression during multistage carcinogenesis of squamous cell carcinoma of the lung." Cancer 92.4 (2001): 849-855.

Tockman, Melvyn S., et al. "Considerations in bringing a cancer biomarker to clinical application." Cancer Research 52.9 Supplement (1992): 2711s-2718s.

Anonymous: "Bronchogenic carcinoma / definition of bronchogenic carcinoma by Medical dictionary," Feb. 13, 2019 (Feb. 13, 2019), retrieved from the internet: URL:https://medical-dictionary. thefreedictionary.com/bronchogenic+carcinoma [retrieved on Feb. 13, 2019].

Spira, et al., Translating Airway Gene Expression into Biomarkers for Tobacco Smoke Exposure and Lung Cancer Detection Smoking and the Airway "field of Injury" as a Paradigm. Retrieved from the internet: URL: https://www.epa.gov/sites/production/files/2014-07/documents/spiraavrum_epa_dec_2012.pdf.

Affymetrix Show Results SULF1 (http://www.affymetrix.com/analysis/netaffx/showresults.affx, downloaded Jul. 6, 2020).

Iacobuzio-Donahue, Christine A., et al. "Highly expressed genes in pancreatic ductal adenocarcinomas: a comprehensive characterization and comparison of the transcription profiles obtained from three major technologies." Cancer research 63.24 (2003): 8614-8622.

Powell, Charles A., et al. "Loss of heterozygosity in epithelial cells obtained by bronchial brushing: clinical utility in lung cancer." Clinical Cancer Research 5.8 (1999): 2025-2034.

Gorringe, Kylie L. "Loss of heterozygosity." eLS (2016): 1-8.

Jung, et al. (Korean Journal of Medicine, 2002, 62(1): 58-68).

British Thoracic Society Bronchoscopy Committee (Thorax, 2001) 56 (suppl): i1-i21.

Tjard Van Heek et al., (Cancer Biology & Therapy, 2004 3(7): 651-656).

International Search Report for PCT/US2017/032517, dated Oct. 2, 2017.

International Search Report for PCT/US2017/041267, dated Dec. 15, 2017.

European Search Report in Application EP 10 18 4732, dated Mar. 21, 2011.

European Search Report in Application EP 10 18 4813, dated Mar. 21, 2011.

European Search Report in Application EP 10 18 4888, dated Mar. 21, 2011.

European Search Report in Application EP 04 81 0818, dated Oct. 28, 2010.

European Search Report in Application EP 08 83 2403, dated Oct. 22, 2010.

European Search Report in Application EP 09 72 4548, Jun. 16, 2011.

European Search Report for European Application No. EP 10195816, dated Oct. 13, 2011.

European Search Report in Application EP 12 17 0635, dated Apr. 22, 2013.

Chinese Search Report in Application 2008801147951 dated Aug. 24, 2012.

Extended European Search Report from EP 16186152.1, dated May 31, 2017.

European Search Report for European Application No. EP 17185133. 0, dated Feb. 21, 2018.

Supplementary European Search Report for European Application No. EP 17 79 6983, Issued Feb. 3, 2020.

European Search Report EP10195822 dated Jun. 20, 2011.

European Search Report EP10195803 dated Jun. 20, 2011.

Non-Final Office Action for U.S. Appl. No. 12/234,588, dated Jun. 27, 2011.

(56)  References Cited

OTHER PUBLICATIONS

Non-Final Office Action for U.S. Appl. No. 10/579,376, dated Jul. 9, 2008.

Non-Final Office Action for U.S. Appl. No. 12/884,714, dated Sep. 23, 2011.

Final Office Action for U.S. Appl. No. 12/234,588, dated Nov. 4, 2011.

Non-Final Office Action for U.S. Appl. No. 12/414,555, dated Nov. 30, 2011.

Final Office Action for U.S. Appl. No. 12/414,555, dated Mar. 15, 2012.

Non-Final Office Action for U.S. Appl. No. 13/346,444, dated Dec. 12, 2012.

Non-Final Office Action for U.S. Appl. No. 12/234,588, dated Mar. 28, 2014.

Final Office Action for U.S. Appl. No. 13/346,444, dated Nov. 27, 2013.

Non-Final Office Action for U.S. Appl. No. 11/294,834, dated Jan. 29, 2014.

Non-Final Office Action for U.S. Appl. No. 14/584,960, dated Apr. 27, 2016.

Final Office Action for U.S. Appl. No. 13/524,749, dated Apr. 3, 2014.

Final Office Action for U.S. Appl. No. 13/323,655, dated Jul. 17, 2014.

Final Office Action for U.S. Appl. No. 11/294,834, date of mailing Aug. 22, 2016.

Non-Final Office Action for U.S. Appl. No. 11/294,834, mailed Dec. 15, 2015.

Non-Final Office Action for U.S. Appl. No. 11/294,834, dated Jun. 24, 2008.

Non-Final Office Action for U.S. Appl. No. 13/323,655, dated Apr. 9, 2013.

Non-Final Office Action for U.S. Appl. No. 13/524,749, dated Sep. 9, 2013.

Final Office Action for U.S. Appl. No. 11/294,834 dated Aug. 18, 2014.

Non-Final Office Action for U.S. Appl. No. 13/323,655 dated Nov. 7, 2013.

Non-Final Office Action for U.S. Appl. No. 11/294,834, dated Jul. 29, 2014.

Non-Final Office Action for U.S. Appl. No. 14/613,210, dated Dec. 6, 2016.

Final Office Action for U.S. Appl. No. 14/500,475, dated Feb. 28, 2017.

Final Office Action for U.S. Appl. No. 14/613,210, dated Apr. 3, 2017.

Non-Final Office Action for U.S. Appl. No. 15/439,791, dated Jun. 14, 2017.

Final Office Action for U.S. Appl. No. 14/500,475, dated Aug. 2, 2017.

Notice of Allowance for U.S. Appl. No. 14/613,210, dated Oct. 31, 2017.

Non-Final Office Action for U.S. Appl. No. 15/644,721, dated Dec. 27, 2017.

Final Office Action for U.S. Appl. No. 15/439,891, issued Feb. 14, 2018.

Non-Final Office Action for U.S. Appl. No. 14/500,475, dated Mar. 26, 2018.

Non-Final Office Action for U.S. Appl. No. 14/690,182, dated Apr. 20, 2018.

Non-Final Office Action for U.S. Appl. No. 15/336,469, dated Apr. 10, 2018.

Non-Final Office Action for U.S. Appl. No. 15/888,831, dated Mar. 27, 2018.

Final Office Action for U.S. Appl. No. 15/644,721, dated Jun. 20, 2018.

Final Office Action for U.S. Appl. No. 15/888,831, dated Jul. 24, 2018.

Final Office Action for U.S. Appl. No. 15/336,469, dated Oct. 9, 2018).

Final Office Action for U.S. Appl. No. 14/690,182, dated Oct. 9, 2018.

Non-Final Office Action for U.S. Appl. No. 15/439,891, dated Dec. 28, 2018.

Non-Final Office Action for U.S. Appl. No. 14/690,182, dated Mar. 22, 2019.

Non-Final Office Action for U.S. Appl. No. 15/888,831, dated Mar. 27, 2019.

Non-Final Office Action for U.S. Appl. No. 15/644,721, dated Mar. 7, 2019.

Final Office Action for U.S. Appl. No. 14/500,475, dated May 14, 2019.

Final Office Action for U.S. Appl. No. 15/439,891, dated Jun. 18, 2019.

Final Office Action for U.S. Appl. No. 15/888,831, dated Oct. 10, 2019.

Notice of Allowance for U.S. Appl. No. 14/500,475, dated Oct. 15, 2019.

Non-final Office Action for U.S. Appl. No. 15/336,469 issued Dec. 4, 2019.

Non-Final Office Action for U.S. Appl. No. 16/510,584 issued Jan. 16, 2020.

Notice of Allowance issued in U.S. Appl. No. 15/888,831, dated Feb. 20, 2020.

Final Office Action for U.S. Appl. No. 16/510,584, issued Apr. 23, 2020.

Final Office Action for U.S. Appl. No. 15/336,469, dated Jul. 10, 2020.

Notice of Allowance issued in U.S. Appl. No. 15/888,831, dated Jun. 1, 2020.

Non-Final Office Action issued in U.S. Appl. No. 16/810,827, dated Aug. 10, 2020.

Notice of Allowance issued in U.S. Appl. No. 15/644,721, dated Sep. 30, 2020.

Non-Final Office Action Issued in U.S. Appl. No. 16/510,584, dated Sep. 30, 2020.

Non-Final Office Action Issued in U.S. Appl. No. 16/300,947, dated Oct. 22, 2020.

Final Office Action Issued in U.S. Appl. No. 16/810,827, dated Nov. 23, 2020.

Jones, A.M., et al., "Value and accuracy of cytology in addition to histology in the diagnosis of lung cancer at flexible bronchoscopy," *Respiratory Medicine*, (2001) 95, 374-378.

Final Office Action Issued in U.S. Appl. No. 16/510,584, dated Feb. 11, 2021.

Guajardo, J.R., et al., "Altered gene expression profiles in nasal respiratory epithelium reflect stable versus acute childhood asthma," *Journal of Allergy and Clinical Immunology*, vol. 115, Issue 2, Feb. 2005, pp. 243-251.

Gebel, et al., "Gene expression profiling in respiratory tissues from rats exposed to mainstream cigarette smoke," *Carcinogenesis*, vol. 25 No. 2 pp. 169-178, 2004.

Sabo-Attwood, et al., "Gene expression profiles reveal increased mClca3 (Gob5) expression and mucin production in a murine model of asbestos-induced fibrogenesis," *Am J Pathol.*, Nov. 2005;167(5):1243-56.

Lee, et al., "Expression of mRNA of Trefoil Factor Peptides in Human Nasal Mucosa," *Acta Otolaryngol*, 2001; 121: 849-853.

Korn, S. H., et al. "Glucocorticoid receptor mRNA levels in bronchial epithelial cells of patients with COPD: influence of glucocorticoids." Respiratory medicine 92.9 (1998): 1102-1109.

Hindiyeh, Musa, et al. "Evaluation of a multiplex real-time reverse transcriptase PCR assay for detection and differentiation of influenza viruses A and B during the 2001-2002 influenza season in Israel." Journal of clinical microbiology 43.2 (2005): 589-595.

Li, Jin, et al. "The cystic fibrosis transmembrane conductance regulator as a biomarker in non-small cell lung cancer." International journal of oncology 46.5 (2015): 2107-2115.

Mak, Victor. Expression of CFTR mRNA in nasal epithelium and vas deferens. Diss. 1999.

(56) References Cited

OTHER PUBLICATIONS

Tokunaga, Katsuo, et al. "Enhanced expression of a glyceraldehyde-3-phosphate dehydrogenase gene in human lung cancers." Cancer Research 47.21 (1987): 5616-5619.

Weng, Ching-Fu, et al. "Association between the risk of lung cancer and influenza: A population-based nested case-control study." International Journal of Infectious Diseases 88 (2019): 8-13.

Wong, SC Cesar, et al. "Development of a quantitative assay for SARS coronavirus and correlation of GAPDH mRNA with SARS coronavirus in clinical specimens." Journal of clinical pathology 58.3 (2005): 276-280.

Zabner, Joseph, et al. "Comparison of DNA-lipid complexes and DNA alone for gene transfer to cystic fibrosis airway epithelia in vivo." The Journal of clinical investigation 100.6 (1997): 1529-1537.

Non-Final Office Action issued in U.S. Appl. No. 16/810,827, dated Apr. 22, 2021.

Final Office Action issued in U.S. Appl. No. 15/336,469, dated Jun. 25, 2021.

Non-Final Office Action issued in U.S. Appl. No. 16/751,145 dated Aug. 18, 2021.

Non-Final Office Action issued in U.S. Appl. No. 16/510,584 dated Aug. 25, 2021.

Non-Final Office Action issued in U.S. Appl. No. 16/810,827 issued Aug. 23, 2021.

Pirooznia, Mehdi, et al. "A comparative study of different machine learning methods on microarray gene expression data." BMC genomics 9.1 (2008): 1-13.

Bertone, Paul, and Mark Gerstein. "Integrative data mining: the new direction in bioinformatics." IEEE Engineering in Medicine and Biology Magazine 20.4 (2001): 33-40.

Details for HT_HG-U133A:212344_AT (Affymetrix Expression Probeset Details, downloaded Mar. 1, 2022).

Non-Final Office Action issued in U.S. Appl. No. 16/657,816 dated May 11, 2022.

Non-Final Office Action issued in U.S. Appl. No. 15/336,469, dated Mar. 8, 2022.

Lampe, et al., "Signatures of Environmental Exposures Using Peripheral Leukocyte Gene Expression: Tobacco Smoke," Cancer Epidemiology, Biomarkers & Prevention, (2004) 13 (3): 445-453.

Chan, E., "Integrating Transcriptomics and Proteomics," Drug Discovery & Development, published in G&P Magazine, vol. 6, No. 3, Apr. 2006, pp. 20-26.

Final Office Action for U.S. Appl. No. 16/579,798, dated Dec. 22, 2022.

Woenckhaus, et al., "Expression Profiling of Non-Small Cell Lung Cancers and Bronchi of Smokers and Non Smokers," Study Group: Molecular Pathology/Pathology—Research and Practice, 200:p. 255, (2004).

Non-Final office action issued in U.S. Appl. No. 16/579,798, dated Jul. 20, 2021.

Final Office Action Issued in U.S. Appl. No. 16/579,798, dated Mar. 2, 2022.

Dubinett, et al. Abstract "The UCLA—Boston University Lung Cancer Biomarker Development Laboratory," National Institutes of Health Grant No. CA152751 (Funding Start Date: Sep. 24, 2010).

Spira et al. Abstract "The Boston University-UCLA Lung Cancer Biomarker Development Lab," National Institutes of Health Grant No. CA214182 (Funding Start Date: Sep. 20, 2016).

Bankovic, et al, "Identification of genes associated with non-small-cell lung cancer promotion and progression", Lung Cancer, vol. 67, No. 2, (2010), pp. 151-159.

Picozzi, et al, "Genomic organization and transcription of the human retinol dehydrogenase 10 (RDH10) gene", Febs Letters, vol. 554, (2003), pp. 59-66.

Chatterjee, et al., "Mitochondrial Subversion in Cancer," Cancer Prev. Res., 4(5), May 2011.

Dasgupta, et al., "Following Mitochondrial Footprints through a Long Mucosal Path to Lung Cancer," PLoS ONE, vol. 4(8), Aug. 2009.

Non-Final Office Action for U.S. Appl. No. 17/182,044, dated Aug. 22, 2024.

Final Office Action for U.S. Appl. No. 17/182,044, dated Jun. 13, 2025.

Non-Final Office Action for U.S. Appl. No. 17/940,776, dated Aug. 12, 2025.

Thiberville, et al., "Evidence of Cumulative Gene Losses with Progression of Premalignant Epithelial Lesions to Carcinoma of the Bronchus," Cancer Research, 55, 5133-5139, 1995.

Non-Final Office Action for U.S. Appl. No. 17/182,044, dated Mar. 6, 2025.

* cited by examiner

*Sample Collection*

Nasal epithelium samples collected from 28 institutions as part of AEGIS clinical trials

*Gene Expression Profiling*

554 samples profiled using Affymetrix Gene 1.0 ST microarrays

31 samples removed because of indeterminate cancer diagnosis at 1-year follow up

*Quality Control*

Microarray quality control of 523 samples using the ArrayQualityMetrics R-package (9 total metrics)

18 samples removed because they were flagged as outliers by at least 3 microarray quality control metrics

*Normalization & Batch Correction*

505 nasal samples were considered suitable for data analysis. These samples were normalized using RMA and batch effects corrected for using ComBat

*Training Set*

AEGIS-1 nasal samples
(n=375)

*Validation Set*

AEGIS-2 nasal samples
(n=130)

*FIG. 4*

NASAL EPITHELIUM GENE EXPRESSION SIGNATURE AND CLASSIFIER FOR THE PREDICTION OF LUNG CANCER

RELATED APPLICATIONS

This application is a continuation application of U.S. application Ser. No. 16/300,947, filed Nov. 12, 2018, which is a U.S. National Application of PCT/US2017/032517 filed May 12, 2017, which claims benefit of U.S. Provisional Application 62/335,391 filed May 12, 2016. The entire teachings of the above applications are incorporated herein by reference.

GOVERNMENT SUPPORT

This invention was made with government support under Contract No. CA152751 and CA214182 awarded by the National Institutes of Health. The Government has certain rights in the invention.

BACKGROUND OF THE INVENTION

Lung cancer is the deadliest form of cancer in the United States and the world. An estimated 221,000 new lung cancer diagnoses are expected in the United States in 2015, and approximately 158,000 men and women are expected to fall victim to the disease during the same time period. The high mortality rate is due, in part, to a failure in 70% of patients to detect lung cancer when it is localized and surgical resection remains feasible.

In 2011, the National Lung Screening Trial (NLST) demonstrated that annual screening of high-risk smokers by low-dose chest CT (LDCT) could lead to the detection of earlier stage lung cancers and reduce mortality by 20%. The expectation is that, similar to other cancers for which there are established screening programs (e.g., breast, prostate and colon cancers), regular lung cancer screening could lead to lung cancer becoming considerably less deadly. As a result, Medicare is now paying for lung cancer screening in defined high risk cohorts. In the NLST trial, there was, however, a considerable false-positive rate associated with CT screening (greater than 95%), with the overwhelming majority of nodules ultimately determined to be benign.

Together, these findings have led to the development of guidelines under which additional diagnostic procedures should be performed in patients with screen-detected nodules, including those established by the Fleischner Society which recommends repeat imaging studies or invasive testing depending on the size of the lesion. Unfortunately, the diagnostic performance under these guidelines remains low and often results in a delay in the diagnosis of early stage lung cancer and unnecessary invasive procedures for those without disease.

With more than 9 million people in the United States meeting NLST screening eligibility criteria, there is a critical need for more accurate, non-invasive tools to prioritize patients for repeat imaging or invasive procedures following the detection of nodules by screening LDCT. Also needed are additional criteria for lung cancer screening eligibility. The current guidelines for determining screening eligibility are based on age and smoking history and present two fundamental challenges. First, even though these guidelines suggest the screening of almost 3% of the total United States population, they capture less than 30% of the cases of lung cancer that are diagnosed each year. Second, the prevalence of lung cancer among the screen-eligible cohort is only about 1%, indicating that the burden of screening could be greatly reduced if screening could be more accurately targeted. Taken together, these data suggest that there is a tremendous need and an opportunity to improve screening eligibility beyond age and smoking history.

SUMMARY OF THE INVENTION

Disclosed herein are assays and methods of diagnosing lung cancer and methods of identifying subjects at risk for developing lung cancer. The inventions disclosed herein provide non-invasive, or in certain embodiments minimally-invasive, methods for diagnosing lung cancer based in-whole or in-part on analysis of gene expression in nasal epithelial cells. Accordingly, provided herein are non-invasive and minimally invasive methods for the diagnosis, prognosis, monitoring and/or follow up of progression or success of treatment based upon the differential expression of certain genes in nasal epithelial cells (e.g., one or more of the 535 genes identified in Table 12 or Table 21).

In certain embodiments, disclosed herein are methods of diagnosing lung cancer in a subject, such methods comprising the steps of: (a) measuring a biological sample comprising nasal epithelial cells of the subject for expression of one or more genes (e.g., one, two, three, four, five, six, seven, eight, nine, ten, fifteen, twenty, twenty five, thirty, forty, fifty or more genes); and (b) comparing the expression of the one or more genes to a control sample of those genes taken from individuals without cancer; wherein the one or more genes are selected from the group consisting of genes in Tables 12, 13 or 21, and wherein differential expression of the subject's one or more genes relative to the control sample is indicative of the subject having lung cancer. In some aspects, non-differential expression of the subject's one or more genes relative to the control sample is indicative of the subject not having lung cancer.

Also disclosed herein are methods of diagnosing lung cancer in a subject, such methods comprising the steps of: (a) measuring a biological sample comprising nasal epithelial cells of the subject for expression of one or more genes (e.g., one, two, three, four, five, six, seven, eight, nine, ten, fifteen, twenty, twenty five, thirty, forty, fifty or more genes); and (b) comparing the expression of the one or more genes to a control sample of those genes from individuals with cancer; wherein the one or more genes are selected from the group consisting of genes in Tables 12 or 13, and wherein differential expression of the subject's one or more genes relative to the control sample is indicative of the subject not having lung cancer. In certain aspects, non-differential expression of the subject's one or more genes relative to the control sample is indicative of the subject having lung cancer.

In certain aspects, the inventions disclosed herein relate to methods of determining whether a subject has quit smoking comprising the steps of: (a) measuring a biological sample comprising nasal epithelial cells of the subject for expression of one or more genes selected from the group consisting of genes in Tables 5 or 6 (e.g., one, two, three, four, five, six, seven, eight, nine, ten, fifteen, twenty, twenty five, thirty, forty, fifty or more genes); and (b) comparing the expression of the one or more genes to a control sample of those genes from non-smokers; wherein altered expression of the subject's genes relative to the control sample is indicative of the subject having quit smoking. In certain aspects, non-altered expression of the subject's one or more genes relative to the control sample is indicative of the subject not having quit smoking.

In still other embodiments, also disclosed herein are methods of determining whether a subject has quit smoking, such methods comprising the steps of: (a) measuring a biological sample comprising nasal epithelial cells of the subject for expression of one or more genes selected from the group consisting of genes in Tables 5 or 6 (e.g., one, two, three, four, five, six, seven, eight, nine, ten, fifteen, twenty, twenty five, thirty, forty, fifty or more genes); and (b) comparing the expression of the one or more genes to a control sample of those genes obtained from smokers; wherein altered expression of the subject's genes relative to the control sample is indicative of the subject not having quit smoking. In some aspects, non-altered expression of the subject's one or more genes relative to the control sample is indicative of the subject having quit smoking.

In certain aspects, the present inventions also relate to methods of determining the likelihood that a subject has lung cancer, such methods comprising: (a) subjecting a biological sample comprising the subject's nasal epithelial cells to a gene expression analysis, wherein the gene expression analysis comprises comparing gene expression levels of one or more genes (e.g., one, two, three, four, five, six, seven, eight, nine, ten, fifteen, twenty, twenty five, thirty, forty, fifty or more genes) selected from the group of genes identified in Tables 12 or 13 to the expression levels of a control sample of those genes from individuals without cancer; and (b) determining the likelihood that the subject has lung cancer by determining differential expression of the subject's one or more genes relative to the group of genes in Tables 12 or 13, wherein differential expression of the subject's genes relative to the control sample is indicative of the subject having a high likelihood of lung cancer. In some embodiments, non-differential expression of the subject's one or more genes relative to the control sample is indicative of the subject having a low likelihood of lung cancer.

In certain embodiments, the one or more genes comprise one or more of the leading edge genes identified in Table 21. For example, any of the methods disclosed herein may comprise, consist of or consist essentially of determining the differential expression of at least one, two, three, four, five, six, seven, eight, nine, ten, fifteen, twenty, twenty five, thirty, forty, fifty or more of the leading edge genes identified in Table 21. In some aspects, the methods disclosed herein comprise determining the differential expression of all of the leading edge genes identified in Table 21.

In certain aspects, the inventions disclosed herein are directed to methods of determining the likelihood that a subject has lung cancer, such methods comprising: (a) subjecting a biological sample comprising the subject's nasal epithelial cells to a gene expression analysis, wherein the gene expression analysis comprises comparing gene expression levels of one or more genes (e.g., one, two, three, four, five, six, seven, eight, nine, ten, fifteen, twenty, twenty five, thirty, forty, fifty or more genes) selected from the group of genes in Tables 12 or 13 to the expression levels of a control sample of those genes from individuals with cancer; and (b) determining the likelihood that the subject has lung cancer by determining differential expression of the subject's one or more genes relative to the group of genes in Tables 12 or 13, wherein differential expression of the subject's genes relative to the control sample is indicative of the subject having a low likelihood of lung cancer. In some embodiments, non-differential expression of the subject's one or more genes relative to the control sample is indicative of the subject having a high likelihood of lung cancer.

In any of the embodiments disclosed herein, at least about two genes are measured (e.g., at least two, three, four, five, six, seven, eight, nine, ten, fifteen, twenty, twenty five, thirty, forty, fifty, sixty, seventy, eighty, ninety, one hundred or more genes are measure). In some embodiments, at least about five genes are measured. In some embodiments, at least about ten genes are measured. In some embodiments, at least about twenty genes are measured. In still other embodiments, at least about thirty genes are measured. In yet other embodiments, at least about forty genes are measured. In still other embodiments, at least about fifty genes are measured.

In some embodiments, the 535 genes listed in Table 12 or Table 21 are grouped into one or more of the four clusters of related genes identified. For example, in some aspects, the genes measured comprise one or more of those genes identified in cluster 1 of Table 12. In some aspects, the genes measured comprise one or more of those genes identified in cluster 2 of Table 12. In some aspects, the genes measured comprise one or more of those genes identified in cluster 3 of Table 12. In some aspects, the genes measured comprise those genes identified in cluster 4 of Table 12. In yet another embodiment, the genes measured comprise at least one gene (e.g., one, two, three, four, five, six, seven, eight, nine, ten, fifteen, twenty, twenty five, thirty, forty, fifty or more genes) from each of clusters 1, 2, 3 and 4 of Table 12.

In certain embodiments, the methods and assays disclosed herein are used in combination with one or more clinical risk factors (e.g., the subject's smoking status) for determining a subject's risk of having lung cancer or at risk of developing lung cancer. For example, such methods and assays may be combined with one or more clinical risk factors selected from the group consisting of advanced age, smoking status, the presence of a lung nodule greater than 3 cm on CT scan, the location of the lesion or nodule (e.g., centrally located, peripherally located or both) and the amount of time since the subject quit smoking. Combining any of the methods and assays disclosed herein with, for example, a subject's positive smoking status may be more indicative of the subject having lung cancer and thereby enhance the predictive value and/or sensitivity of the methods and assays disclosed herein. Similarly, in some embodiments, the combination of the methods and assays disclosed herein and a subject's age (e.g., advanced age) may also be indicative of the subject having, or of being at increased risk of having lung cancer. In still other embodiments, the methods and assays disclosed herein comprise performing or reviewing the results of one or more imaging studies (e.g., chest X-ray, assessing the subject for the presence of a lung nodule or lesion greater than 3 cm on the subject's CT scan, assessing lesion or nodule location), which if positive, may be further indicative of the subject having lung cancer. In some embodiments, the methods and assays disclosed herein may further comprise a step of assessing the subject's time since quitting smoking, which if greater than 15 years may be indicative of the subject having lung cancer.

In certain aspects of any of the methods, compositions or assays disclosed herein, the one or more genes assessed comprise, consist of, or consist essentially of one or more genes from Table 14. In some embodiments of any of the methods, compositions or assays disclosed herein, the one or more genes comprise, consist of, or consist essentially of one or more genes from Table 15. In some embodiments of any of the methods compositions or assays disclosed herein, the one or more genes further comprise, consist of, or consist essentially of one or more genes from Table 13. In some embodiments, the one or more genes comprise, consist of, or consist essentially of all of the genes from Table 14. In some embodiments, the one or more genes comprise, consist of, or consist essentially of one or more genes from Table 13. In certain aspects, the one or more genes further comprise one or more genes from Table 5. In some other embodiments, the one or more genes further comprise one or more genes from Table 6.

In certain embodiments of any of the methods disclosed herein, the one or more genes (e.g., one or more genes from Table 12 or Table 21) are associated with DNA damage. In certain embodiments of any of the methods disclosed herein, the one or more genes (e.g., one or more genes from Table 12 or Table 21) are associated with regulation of apoptosis. In still other embodiments of any of the methods disclosed herein, the one or more genes (e.g., one or more genes from Table 12 or Table 21) are associated with immune system activation (e.g., one or more genes is associated with the interferon-gamma signaling pathway or associated with antigen presentation).

In some embodiments, expression of the one or more genes from the biological sample (e.g., a biological sample comprising nasal epithelial cells) is determined using a quantitative reverse transcription polymerase chain reaction, a bead-based nucleic acid detection assay or a oligonucleotide array assay.

In certain aspects of any of the methods disclosed herein, the method further comprises applying a gene filter to the expression to exclude specimens potentially contaminated with inflammatory cells.

In some embodiments, the methods and assays disclosed herein are useful for identifying subjects having, or of being at increased risk of having lung cancer. In certain aspects, the lung cancer is selected from the group consisting of adenocarcinoma, squamous cell carcinoma, small cell cancer or non-small cell cancer.

As discussed above, in some aspects, the assays and methods disclosed herein rely in part on determining the differential expression of one or more genes in a subject's nasal epithelial cells (e.g., one or more of the genes set forth in Table 12 or Table 21). In some embodiments, the one or more genes comprise DNA. In some embodiments, the one or more genes comprise RNA. In some embodiments, the one or more genes comprise mRNA.

In some embodiments, the biological sample obtained from the subject comprises nasal epithelial cells. In some embodiments, the biological sample consists or consists essentially of nasal epithelial cells. In some embodiments, the biological sample does not comprise bronchial epithelial cells or bronchial epithelial tissue. In still other embodiments, the biological sample does not comprise cells or tissues from the bronchial airway.

In certain aspects of any of the inventions disclosed herein, if such method is indicative of the subject having lung cancer or of being at risk of developing lung cancer, the method further comprises treating the subject. Accordingly, in certain embodiments, any of the methods disclosed herein may further comprise a step of administering a cancer treatment to the subject (e.g., a treatment comprising one or more of chemotherapy, radiation therapy, immunotherapy, surgical intervention and combinations thereof). For example, in those embodiments where the methods and assays disclosed herein are indicative of a subject being at a higher risk of having or developing lung cancer, the subject may be subjected to a direct tissue sampling or biopsy of the nodule, under the presumption that the positive test indicates a higher likelihood of the nodule is a cancer. Conversely, in those instances where the methods and assays disclosed herein are indicative of a subject having a reduced risk of developing lung cancer, then the subject may be subjected to further imaging surveillance (e.g., a repeat computerized tomography scan to monitor whether the nodule grows or changes in appearance before doing a more invasive procedure), or a determination made to withhold a particular treatment (e.g., chemotherapy) on the basis of the subject's favorable or reduced risk of having or developing lung cancer.

Similarly, in certain aspects of any of the inventions disclosed herein, if such method is indicative of the subject having not quit smoking or of being a smoker, the method further comprises treating the subject. Accordingly, in certain embodiments, any of the methods disclosed herein may further comprise a step of administering a smoking-cessation treatment to the subject (e.g., a treatment comprising nicotine replacement therapy).

Also disclosed herein are minimally-invasive methods and assays useful for determining the likelihood that a subject does (or does not) have lung cancer, such methods and assays comprising a step of (a) detecting, by quantitative reverse transcription polymerase chain reaction, a bead-based nucleic acid detection assay or a oligonucleotide array assay, mRNA or cDNA expression levels in a sample comprising nasal epithelial cells from a subject; (b) determining mRNA or cDNA expression levels in the sample of nasal epithelial cells of two or more gene selected from the group consisting of the genes in Table 12, Table 13 or Table 21; and (c) based on the expression levels determined in step (b) (e.g., differentially expressed levels), determining a lung cancer risk-score that is indicative of the likelihood that the subject does not haves lung cancer. In certain aspects, the subject has undergone an indeterminate or non-diagnostic bronchoscopy procedure. In certain embodiments, the genes comprise at least 1 gene from Table 13 (e.g., about one, two, three, four, five, six, seven, eight, nine or ten genes from Table 13). In some embodiments, the genes comprise at least 10 genes from Table 13 (e.g., about ten, eleven, twelve, thirteen, fourteen, fifteen, sixteen, seventeen, eighteen, nineteen or twenty genes from Table 13). In still other embodiments, the genes comprise at least 20 genes from Table 13 (e.g., about twenty one, twenty two, twenty three, twenty four, twenty five, twenty six, twenty seven, twenty eight, twenty nine or thirty genes from Table 13). In still other aspects, the genes comprise all of the genes from Table 13.

In certain embodiments, the methods and assays disclosed herein further comprise a step of determining one or more of the subject's clinical risk factors affecting the subject's risk for having lung cancer (e.g., one or more clinical risk factors selected from the group consisting of advanced age, smoking status, the presence of a lung nodule greater than 3 cm on CT scan, lesion location and time since quitting smoking). In some embodiments, the subject's positive smoking status is indicative of the subject having lung cancer. In some aspects, the subject's advanced age is indicative of the subject having lung cancer. In some embodiments, the presence of a lung nodule greater than 3 cm on the subject's CT scan is indicative of the subject having lung cancer. In still other embodiments, the subject's time since quitting smoking greater than 15 years is indicative of the subject having lung cancer.

Also disclosed herein are compositions (e.g., diagnostic kits) and assays that comprise one or more nucleic acid probes, wherein each of the one or more nucleic acids probes specifically hybridizes with the expression products of five or more genes selected from the group of genes identified in any of Table 5, Table 6, Table 12, Table 13, Table 14, Table 15 or Table 21. In certain aspects, such one or more expression products comprise mRNA. In some aspects, such compositions measure expression of at least ten genes. In some aspects, such compositions measure expression of at least fifteen genes. In some aspects, such compositions measure expression of at least twenty genes. In some aspects, such compositions measure expression of at least thirty genes. In some embodiments, such compositions measure expression of at least forty genes. In still other embodiments, such compositions measure expression of at least fifty genes. In some embodiments, such compositions measure expression of at least one hundred genes.

In certain embodiments, the compositions (e.g., diagnostic kits) disclosed herein measure expression of those genes identified in cluster 1 of Table 12. In certain embodiments, the compositions disclosed herein measure expression of those genes identified in cluster 2 of Table 12. In yet other embodiments, the compositions disclosed herein measure expression of those genes identified in cluster 3 of Table 12. In still other embodiments, the compositions disclosed herein measure expression of those genes identified in cluster 4 of Table 12. In certain aspects, such compositions measure expression of one or more genes in Table 12 and comprise at least one gene from each of clusters 1-4.

In certain aspects of any of the methods, assays or compositions disclosed herein, the one or more genes are associated with DNA damage. In certain aspects of any of the methods, assays or compositions disclosed herein, the one or more genes are associated with the regulation of apoptosis. In certain embodiments of any of the methods, assays or compositions disclosed herein, the one or more genes are immune system activation (e.g., associated with the interferon-gamma signaling pathway and/or antigen presentation).

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows that the 535 genes with cancer-associated expression in nasal epithelium were split into up- and downregulated gene sets, and the present inventors examined their distribution within all genes ranked from most down-regulated (left) to most upregulated (right) in the bronchial epithelium of patients with cancer using gene set enrichment analysis. The present inventors found that the genes with increased expression in nasal epithelium were enriched among the genes that are most induced in the bronchial epithelium of patients with cancer (top; P<0.001 by a two-sided permutation-based Kolmogorov-Smirnov-like test) while the reverse was true for genes with decreased expression in nasal epithelium (bottom; P<0.001 by a two-sided permutation based Kolmogorov-Smirnov-like test). Genes included in the core enrichment are shown in the green box. FIG. 2B depicts heatmaps and hierarchical clustering of the core enrichment genes in nasal (left) and bronchial (right) samples. All statistical tests were two-sided.

FIG. 4 is a flowchart that illustrates data acquisition and processing workflow. Nasal epithelial samples from smokers with and without lung cancer were collected from 28 institutions across the U.S., Canada, and Europe as part of the AEGIS clinical trials. 557 samples were received by Boston University and run on Affymetrix Gene 1.0 ST microarrays. 31 samples were lost due to indeterminate cancer diagnosis at follow up. 18 samples were removed as part of the quality control process. The 526 remaining samples were RMA normalized and batch-corrected together, and then separated into a training set (AEGIS-1, n=375) and validation set (AEGIS-2, n=130).

DETAILED DESCRIPTION OF THE INVENTION

Figure 1:
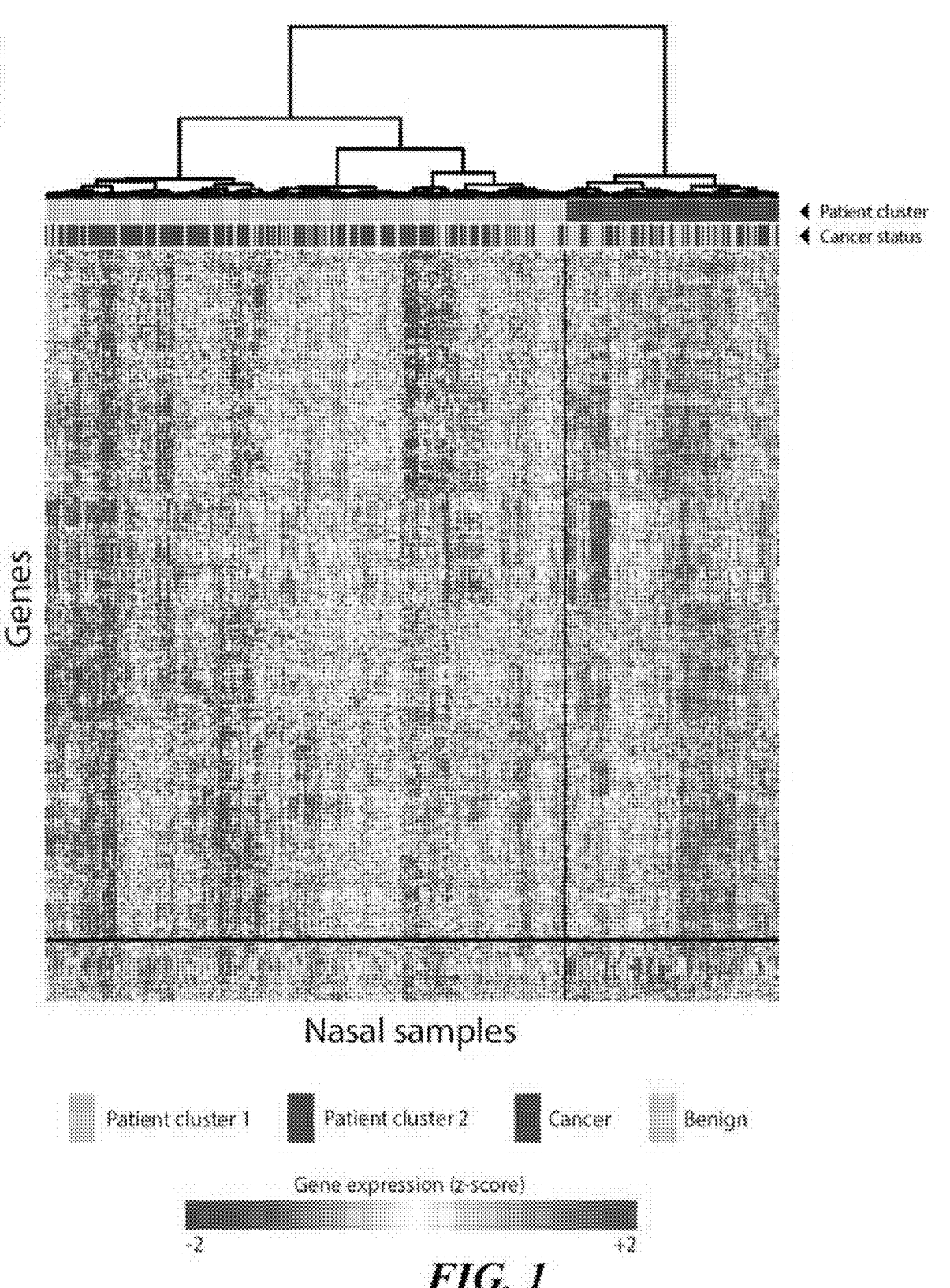
FIG. 1 depicts the characterization of 535 cancer-associated nasal epithelial genes in the training set. Five hundred thirty-five genes were differentially expressed by cancer status in the nasal training set (P<0.001) using a linear model that included cancer status, smoking status, pack-years, sex, age, and RIN as covariates. These genes were grouped into two co-expression clusters by unsupervised hierarchical clustering. Unsupervised hierarchical clustering of patients across these genes revealed two primary patient clusters.

Disclosed herein are novel, non-invasive or minimally invasive assays and related methods that are useful for diagnosing lung cancer or determining a subject's previous smoking status, such assays and methods comprising a step of determining the expression of one or more genes in nasal epithelial cells of a subject. For example, in certain aspects the methods disclosed herein comprise a step of comparing the expression of one or more of the 535 genes set forth in Table 12 or Table 21 in a subject's nasal epithelial cells to expression of the same genes in a nasal epithelial cell from a control subject. In certain aspects, any of the methods disclosed herein further comprise applying a gene filter to the expression to exclude specimens potentially contaminated with inflammatory cells.

The assays and methods disclosed herein provide the first ever claim of a nasal epithelium gene expression classifier composed of the specific genes described herein and that can be used to predict the presence or absence of lung cancer (e.g., adenocarcinoma, squamous cell carcinoma, small cell cancer or non-small cell cancer). Additionally, the assays and methods disclosed herein provide the first ever claim of a nasal epithelium gene expression classifier that can predict whether a subject is a current or former smoker. The assays and methods provided herein, whether used alone or in combination with other methods, provide useful information for health care providers to assist them in making early diagnostic and therapeutic decisions for a subject, thereby improving the likelihood that the subject's disease may be effectively treated. In some embodiments, methods and assays disclosed herein are employed in instances where other methods have failed to provide useful information regarding the lung cancer status of a subject.

Previous work from our group has demonstrated that gene expression in normal appearing bronchial and nasal epithelial cells is dramatically altered in current and former smokers (Zhang, et al.) and that several of these alterations persist for decades upon smoking cessation (Beane, et al.). The present inventors have extended these observations to show that gene expression in normal-appearing airway cells is also altered by smoking-related lung diseases such as COPD and lung cancer. For lung cancer, the present inventors measured gene expression in bronchial epithelial samples collected from a cohort of patients undergoing bronchoscopy for clinical suspicion of lung cancer and identified a panel of 80 genes that were indicative of the presence of lung cancer (Spira, et al., 2007) and which were independent of other clinical factors as a predictor of lung cancer (Beane, et al., 2008). More recently, a 232 gene signature was identified as differentially expressed in the bronchial epithelium of patients with lung cancer (Whitney, et al., 2015). This signature was ultimately used to develop a 23-gene bronchial genomic classifier (Whitney, et al., 2015; Silvestri, et al., 2015) that was prospectively validated in two independent cohorts consisting of over 600 patients.

The present inventions are based upon the surprising finding of a strong concordance between bronchial and nasal epithelium's response to cigarette smoke exposure, and our observation that lung disease alters gene expression in normal appearing nasal epithelium that is physically distant from the site of disease. The assays and methods disclosed herein are characterized by the accuracy with which they can discriminate lung cancer from non-lung cancer and their non-invasive or minimally-invasive nature. In some aspects, the assays and methods disclosed herein are based on detecting differential expression of one or more genes in nasal epithelial cells and such assays and methods are based on the discovery that such differential expression in nasal epithelial cells are useful for diagnosing cancer in the distant lung tissue. Accordingly, the inventions disclosed herein provide a substantially less invasive method for diagnosis, prognosis and follow-up of lung cancer using gene expression analysis of biological samples comprising nasal epithelial cells.

In contrast to conventional invasive methods, such as bronchoscopy, the assays and methods disclosed herein rely on expression of certain genes in a biological sample obtained from a subject. As the phrase is used herein, "biological sample" means any sample taken or derived from a subject comprising one or more nasal epithelial cells. As used herein, the phrase "obtaining a biological sample" refers to any process for directly or indirectly acquiring a biological sample from a subject. For example, a biological sample may be obtained (e.g., at a point-of-care facility, a physician's office, a hospital) by procuring a tissue or fluid sample from a subject. Alternatively, a biological sample may be obtained by receiving the sample (e.g., at a laboratory facility) from one or more persons who procured the sample directly from the subject.

Such biological samples comprising nasal epithelial cells may be obtained from a subject (e.g., a subject at risk for lung cancer) using a brush or a swab. The biological samples comprising nasal epithelial cells may be collected by any means known to one skilled in the art and, in certain embodiments, is obtained non-invasively. For example, in certain embodiments, a biological sample comprising nasal epithelial cells may be collected from a subject by nasal brushing. Similarly, nasal epithelial cells may be collected by brushing the inferior turbinate and/or the adjacent lateral nasal wall. For example, following local anesthesia with 2% lidocaine solution, a CYROBRUSH® (MedScand Medical, Malmö Sweden) or a similar device, is inserted into the nare of the subject, for example the right nare, and under the inferior turbinate using a nasal speculum for visualization. The brush is turned (e.g., turned 1, 2, 3, 4, 5 times or more) to collect the nasal epithelial cells, which may then be subjected to analysis in accordance with the assays and methods disclosed herein.

In certain embodiments, the biological sample does not include or comprise bronchial airway epithelial cells. For example, in certain embodiments, the biological sample does not include epithelial cells from the mainstem bronchus. In certain aspects, the biological sample does not include cells or tissue collected from bronchoscopy. In some embodiments, the biological sample does not include cells or tissue isolated from a pulmonary lesion.

In certain embodiments, the subject has undergone an indeterminate or non-diagnostic bronchoscopy. In some embodiments, the method comprises determining that the subject does not have lung cancer based on the expression levels of one or more (such as, e.g., 2 or more) of the 535 genes set forth in Table 12 or Table 21 in a subject's nasal epithelial cells. In particular embodiments, the method comprises determining that the subject does not have lung cancer based on the expression levels in a nasal epithelial cell sample from the subject of one or more (such as, e.g., 2, 3, 4, 5, 6, 7, 8, 9, 10, 11, 12, 13, 14, 15, 16, 17, 18, 19, 20, 21, 22, 23, 24, 25, 26, 26, 28, 29 or 30) genes listed in Table 13. In particular embodiments, the method comprises determining the subject does or does not have cancer by applying a classifier algorithm that is trained to differentiate cancer versus non-cancer based upon the expression of at least the 30 genes expressed in Table 13. In some such embodiments, the classifier is as shown in Table 17.

To isolate nucleic acids from the biological sample, the epithelial cells can be placed immediately into a solution that prevents nucleic acids from degradation. For example, if the nasal epithelial cells are collected using the CYTO-BRUSH, and one wishes to isolate RNA, the brush is placed immediately into an RNA stabilizer solution, such as RNALATER®, AMBION®, Inc. One can also isolate DNA. After brushing, the device can be placed in a buffer, such as phosphate buffered saline (PBS) for DNA isolation.

The nucleic acids (e.g., mRNA) are then subjected to gene expression analysis. Preferably, the nucleic acids are isolated and purified. However, if techniques such as microfluidic devices are used, cells may be placed into such device as whole cells without substantial purification. In one embodiment, nasal epithelial cell gene expression is analyzed using gene/transcript groups and methods of using the expression profile of these gene/transcript groups in diagnosis and prognosis of lung diseases. In some embodiments, differential expression of the one or more genes determined with reference to the one or more of the 535 genes set forth in Table 12 or Table 21.

As used herein, the term "differential expression" refers to any qualitative or quantitative differences in expression of the gene or differences in the expressed gene product (e.g., mRNA) in the nasal epithelial cells of the subject. A differentially expressed gene may qualitatively have its expression altered, including an activation or inactivation, in, for example, the presence of absence of cancer and, by comparing such expression in nasal epithelial cell to the expression in a control sample in accordance with the methods and assays disclosed herein, the presence or absence of lung cancer may be determined.

In some embodiments, subjecting the nucleic acids to gene expression analysis may comprise directly measuring RNA (e.g., mRNA expression levels). In some embodiments, subjecting the nucleic acids to gene expression analysis may comprise detecting cDNAs produced from RNA expressed in the test sample, wherein, optionally, the cDNA is amplified from a plurality of cDNA transcripts prior to the detecting step. In some embodiments, subjecting the nucleic acids to gene expression analysis comprises labeling one or more of the nucleic acids.

In certain embodiments, the methods and assays disclosed herein are characterized as being much less invasive relative to, for example, bronchoscopy. The methods provided herein not only significantly increase the sensitivity or diagnostic accuracy of lung cancer or smoking status, but also make the analysis much less invasive and thus much easier for the subjects and clinician to perform. In some embodiments, the likelihood that the subject has lung cancer is also determined based on the presence or absence of one or more clinical risk factors or diagnostic indicia of lung cancer, such as the results of imaging studies. When the assays and methods of the present invention are combined with, for example, one or more relevant clinical risk factors (e.g., a subject's smoking history), the diagnosis of lung cancer may be dramatically enhanced, enabling the detection of lung cancer at an earlier stage, and by providing far fewer false negatives and/or false positives. As used herein, the term "clinical risk factors" refers broadly to any diagnostic indicia (e.g., subjective or objective diagnostic criteria) that would be relevant for determining a subject's risk of having or developing lung cancer. Exemplary clinical risk factors that may be used in combination with the methods or assays disclosed herein include, for example, imaging studies (e.g., chest X-ray, CT scan, etc.), the subject's smoking status or smoking history and/or the subject's age. In certain aspects, when such clinical risk factors are combined with the methods and assays disclosed herein, the predictive power of such methods and assays may be further enhanced.

In some embodiments, the biological sample comprising the subject's nasal epithelial cells are analyzed for the expression of certain genes or gene transcripts, either individually or in groups or subsets. In one embodiment, the inventions disclosed herein provide a group of genes (e.g., one or more of the genes listed in Table 12, Table 13 or Table 21) that may be analyzed to determine the presence or absence of lung cancer (e.g., adenocarcinoma, squamous cell carcinoma, small cell cancer and/or non-small cell cancer) from a biological sample comprising the subject's nasal epithelial cells. In one embodiment, the inventions disclosed herein provide a group of genes (e.g., Tables 5 or 6) that may be analyzed to determine a subject's smoking status from a biological sample comprising the subject's nasal epithelial cells. For example, the biological sample may be analyzed to determine the expression of one or more genes listed in any of Table 5, Table 6, Table 12, Table 13, Table 14, Table 15 and/or Table 21, to thereby determine whether the subject has or is at risk of developing lung cancer. In certain embodiments, the nasal epithelial cells are analyzed using at least one and no more than 535 of the genes listed in Table 12 or Table 21. For example, about 1, 2, 3, 4, 5, 6, 7, 8, 9, 10, 10-15, 15-20, 20-30, 30-40, 40-50, 50-60, 60-70, 70-80, 80-90, 90-100, or at least 10, at least 20, at least 30, at least 40 at least 50, at least 60, at least 70, at least 80, at least 90, at least 100, at least 110, at least 120, at least 130, at least 140, at least 150, at least 160, at least or at maximum of 170, at least or at maximum of 180, at least or at maximum of 190, at least or at maximum of 200, 210, 220, 230, 240, 250, 260, 270, 280, 290, 300, 310, 320, 330, 340, 350, 360, 375, 380, 390, 400, 410, 420, 425, 450, 475, 500, 525 or at least 530 or at maximum of the 535 genes as listed on Table 12 or Table 21.

One example of the gene transcript groups useful in the diagnostic/prognostic assays and methods of the invention are set forth in Table 5, Table 6, Table 12, Table 13 or Table 21. The present inventors have determined that taking any group that has at least about 5, 10, 15, 20, 25, 30, 40, 50, 60, 70, 80, 90, 100 or more of the Table 12 or Table 21 genes provides a much greater lung cancer diagnostic capability than chance alone. Similarly, the present inventors have determined that taking any group that has at least about 5, 10, 15, 20, 25, 30, 40, 50, 60 or more of the Tables 5 or 6 genes provides a much greater capability to determine a subject's smoking status than chance alone. Preferably one would analyze the nasal epithelial cells using more than about 20 of these genes, for example about 20-100 and any combination between, for example, 21, 22, 23, 24, 25, 26, 27, 28, 29, 30, and so on. In some instances, the present inventors have determined that one can enhance the sensitivity or diagnostic accuracy of the methods and assays disclosed herein by adding additional genes to any of these specific groups. For example, in certain aspects, the accuracy of such methods may approach about 70%, about 75%, about 80%, about 82.5%, about 85%, about 87.5%, about 88%, about 90%, about 92.5%, about 95%, about 97.5%, about 98%, about 99% or more by evaluating the differential expression of more genes from the set (e.g., the set of genes set forth in Tables 5, 6, 12, 13 or 21).

In some embodiments, the diagnosis of lung cancer is made by comparing the expression of the genes or groups of genes set forth in, for example Table 12 or Table 21, by the subject's nasal epithelial cells to a control subject or a control group (e.g., a positive control with a confirmed diagnosis of lung cancer). Similarly, in certain aspects, the determination of a subject's smoking status is made by comparing the expression of the genes or groups of genes from the subject's nasal epithelial cells to a control subject or a control group (e.g., a non-smoker negative control). In certain embodiments, an appropriate control is an expression level (or range of expression levels) of a particular gene that is indicative of a known lung cancer status. An appropriate reference can be determined experimentally by a practitioner of the methods disclosed herein or may be a pre-existing expression value or range of values. When an appropriate control is indicative of lung cancer, a lack of a detectable difference (e.g., lack of a statistically significant difference) between an expression level determined from a subject in need of characterization or diagnosis of lung cancer and the appropriate control may be indicative of lung cancer in the subject. When an appropriate control is indicative of lung cancer, a difference between an expression level determined from a subject in need of characterization or diagnosis of lung cancer and the appropriate reference may be indicative of the subject being free of lung cancer.

Alternatively, an appropriate control may be an expression level (or range of expression levels) of one or more genes that is indicative of a subject being free of lung cancer. For example, an appropriate control may be representative of the expression level of a particular set of genes in a reference (control) biological sample obtained from a subject who is known to be free of lung cancer. When an appropriate control is indicative of a subject being free of lung cancer, a difference between an expression level determined from a subject in need of diagnosis of lung cancer and the appropriate reference may be indicative of lung cancer in the subject. Alternatively, when an appropriate reference is indicative of the subject being free of lung cancer, a lack of a detectable difference (e.g., lack of a statistically significant difference) between an expression level determined from a subject in need of diagnosis of lung cancer and the appropriate reference level may be indicative of the subject being free of lung cancer.

The control groups can be or comprise one or more subjects with a positive lung cancer diagnosis, a negative lung cancer diagnosis, non-smokers, smokers and/or former smokers. Preferably, the genes or their expression products in the nasal epithelial cell sample of the subject are compared relative to a similar group, except that the members of the control groups may not have lung cancer. For example, such a comparison may be performed in the nasal epithelial cell sample from a smoker relative to a control group of smokers who do not have lung cancer. Such a comparison may also be performed, e.g., in the nasal epithelial cell sample from a non-smoker relative to a control group of non-smokers who do not have lung cancer. Similarly, such a comparison may be performed in the nasal epithelial cell sample from a former smoker or a suspected smoker relative to a control group of smokers who do not have lung cancer. The transcripts or expression products are then compared against the control to determine whether increased expression or decreased expression can be observed, which depends upon the particular gene or groups of genes being analyzed, as set forth, for example, in Table 12 or Table 21. In certain embodiments, at least 50% of the gene or groups of genes subjected to expression analysis must provide the described pattern. Greater reliability is obtained as the percent approaches 100%. Thus, in one embodiment, at least about 55%, 60%, 65%, 70%, 75%, 80%, 85%, 90%, 95%, 98%, 99% of the one or more genes subjected to expression analysis demonstrate an altered expression pattern that is indicative of the presence or absence of lung cancer, as set forth in, for example, Table 12 or Table 21. Similarly, in one embodiment, at least about 55%, 60%, 65%, 70%, 75%, 80%, 85%, 90%, 95%, 98%, 99% of the one or more genes subjected to expression analysis demonstrate an altered expression pattern that is indicative of the subject's smoking status, as set forth in, for example, Table 5 or Table 6.

Any combination of the genes and/or transcripts of Table 12 or Table 21 can be used in connection with the assays and methods disclosed herein. In one embodiment, any combination of at least 5-10, 10-20, 20-30, 30-40, 40-50, 50-60, 60-70, 70-80, 80, 80-90, 90-100, 100-120, 120-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500, 500-

510, 510-520, 520-530, and up to about 535 genes selected from the group consisting of genes or transcripts as shown in the Table 12 or Table 21.

The analysis of the gene expression of one or more genes may be performed using any gene expression methods known to one skilled in the art. Such methods include, but are not limited to expression analysis using nucleic acid chips (e.g. Affymetrix chips) and quantitative RT-PCR based methods using, for example real-time detection of the transcripts. Analysis of transcript levels according to the present invention can be made using total or messenger RNA or proteins encoded by the genes identified in the diagnostic gene groups of the present invention as a starting material. In certain embodiments the analysis is or comprises an immunohistochemical analysis with an antibody directed against proteins comprising at least about 10-20, 20-30, preferably at least 36, at least 36-50, 50, about 50-60, 60-70, 70-80, 80-90, 96, 100-180, 180-200, 200-250, 250-300, 300-350, 350-400, 400-450, 450-500, 500-535 proteins encoded by the genes and/or transcripts as shown in Table 12 or Table 21.

In one embodiment, the analysis is performed analyzing the amount of proteins encoded by one or more of the genes listed in Table 12 or Table 21 and present in the sample. In one embodiment the analysis is performed using DNA by analyzing the gene expression regulatory regions of the airway transcriptome genes using nucleic acid polymorphisms, such as single nucleic acid polymorphisms or SNPs, wherein polymorphisms known to be associated with increased or decreased expression are used to indicate increased or decreased gene expression in the individual. In one embodiment, the present invention uses a minimally invasive sample procurement method for obtaining nasal epithelial cell RNA (e.g., mRNA) that can be analyzed by expression profiling, for example, by array-based gene expression profiling. These methods can be used to determine if nasal epithelial cell gene expression profiles are affected by cancer. The methods disclosed herein can also be used to identify patterns of gene expression that are diagnostic of lung disorders/diseases, for example, cancer, and to identify subjects at risk for developing lung cancer. All or a subset of the genes identified according to the methods described herein can be used to design an array, for example, a microarray, specifically intended for the diagnosis or prediction of lung disorders or susceptibility to lung disorders. The efficacy of such custom-designed arrays can be further tested, for example, in a large clinical trial of smokers.

In some embodiments, the gene expression levels are determined by RT-PCR, DNA microarray hybridization, RNASeq, or a combination thereof. In some embodiments, one or more of the gene expression products is labeled. For example, a mRNA (or a cDNA made from such an mRNA) from a nasal epithelial cell sample may be labeled.

The methods of analyzing expression and/or determining an expression profile of the one or more genes include, for example, Northern-blot hybridization, ribonuclease protection assay, and reverse transcriptase polymerase chain reaction (RT-PCR) based methods. In certain aspects, the different RT-PCR based techniques are a suitable quantification method for diagnostic purposes of the present invention, because they are very sensitive and thus require only a small sample size which is desirable for a diagnostic test. A number of quantitative RT-PCR based methods have been described and are useful in measuring the amount of transcripts according to the present invention. These methods include RNA quantification using PCR and complementary DNA (cDNA) arrays (Shalon, et al., Genome Research 6(7):639-45, 1996; Bernard, et al., Nucleic Acids Research 24(8): 1435-42, 1996), real competitive PCR using a MALDI-TOF Mass spectrometry based approach (Ding, et al., PNAS, 100: 3059-64, 2003), solid-phase mini-sequencing technique, which is based upon a primer extension reaction (U.S. Pat. No. 6,013,431, Suomalainen, et al., Mol. Biotechnol. June; 15(2): 123-31, 2000), ion-pair high-performance liquid chromatography (Doris, et al., J. Chromatogr. A May 8; 806(1):47-60, 1998), and 5' nuclease assay or real-time RT-PCR (Holland, et al., Proc Natl Acad Sci USA 88: 7276-7280, 1991).

Additional approaches to assess gene expression of the one or more genes are known in the art and may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, serial analysis of gene expression (SAGE), enzyme linked immunoabsorbance assays, mass-spectrometry, immunohistochemistry, blotting, sequencing, RNA sequencing, DNA sequencing (e.g., sequencing of cDNA obtained from RNA); Next-Gen sequencing, nanopore sequencing, pyrosequencing, or Nanostring sequencing. For example, gene expression product levels may be determined according to the methods described in Kim, et. al. (Lancet Respir Med. 2015 June; 3(6):473-82, incorporated herein in its entirety, including all supplements). As used herein, the terms "assaying" or "detecting" or "determining" are used interchangeably in reference to determining gene expression product levels, and in each case, it is contemplated that the above-mentioned methods of determining gene expression product levels are suitable for detecting or assaying gene expression product levels. Gene expression product levels may be normalized to an internal standard such as total mRNA or the expression level of a particular gene including but not limited to glyceraldehyde 3 phosphate dehydrogenase, or tubulin.

In various embodiments, a sample comprises cells harvested from a tissue, e.g., in some embodiments the sample comprises cells harvested from a nasal epithelial cell sample. In certain embodiments, the cells may be harvested from a sample using standard techniques known in the art or disclosed herein. For example, in one embodiment, cells are harvested by centrifuging a cell sample and re-suspending the pelleted cells. The cells may be re-suspended in a buffered solution such as phosphate-buffered saline (PBS). After centrifuging the cell suspension to obtain a cell pellet, the cells may be lysed to extract nucleic acid, e.g., messenger RNA. All samples obtained from a subject, including those subjected to any sort of further processing, are considered to be obtained from the subject.

The sample, in one embodiment, is further processed before detection of the gene expression products is performed as described herein. For example, mRNA in a cell or tissue sample may be separated from other components of the sample. The sample may be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the gene expression product. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in their entirety for all purposes, transcription amplification (Kwoh et al., Proc. Natl. Acad. Sci. USA, 86:1173 (1989), incorporated by reference in its entirety for all purposes), self-sustained sequence replication (Guatelli et al., Proc. Nat. Acad. Sci. USA, 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in their entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA gene expression product sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a gene expression product of interest is detected at the nucleic acid level via detection of non-natural cDNA molecules.

The gene expression products described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full length gene expression product polynucleotide disclosed herein. A fragment of a gene expression product polynucleotide will generally encode at least 15, 25, 30, 50, 100, 150, 200, or 250 contiguous amino acids, or up to the total number of amino acids present in a full-length gene expression product protein of the invention.

In certain embodiments, a gene expression profile may be obtained by whole transcriptome shotgun sequencing ("WTSS" or "RNAseq"; see, e.g., Ryan et. al. *BioTechniques* 45: 81-94), which makes the use of high-throughput sequencing technologies to sequence cDNA in order to about information about a sample's RNA content. In general terms, cDNA is made from RNA, the cDNA is amplified, and the amplification products are sequenced.

After amplification, in some embodiments, the cDNA may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (*Nature* 2005 437: 376-80); Ronaghi et al (*Analytical Biochemistry* 1996 242: 84-9); Shendure (*Science* 2005 309: 1728); Imelfort et. al. (*Brief Bioinform.* 2009 10:609-18); Fox et. al. (*Methods Mol Biol.* 2009; 553:79-108); Appleby et. al. (*Methods Mol Biol.* 2009; 513: 19-39) and Morozova (Genomics. 2008 92:255-64), which are a; incorporated by reference for the general descriptions of the methods and the particular steps of the methods, including all starting products, reagents, and final products for each of the steps. As would be apparent, forward and reverse sequencing primer sites that compatible with a selected next generation sequencing platform may be added to the ends of the fragments during the amplification step.

In other embodiments, the products may be sequenced using nanopore sequencing (e.g. as described in Soni et. al. *Clin Chem* 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

In some embodiments, the gene expression product of the subject methods is a protein, and the amount of protein in a particular biological sample may be analyzed using a classifier derived from protein data obtained from cohorts of samples. The amount of protein may be determined by one or more of the following: enzyme-linked immunosorbent assay (ELISA), mass spectrometry, blotting, or immunohistochemistry.

In some embodiments, gene expression product markers and alternative splicing markers may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook Molecular Cloning a Laboratory Manual 2001 and Baldi, P., and Hatfield, W. G., DNA Microarrays and Gene Expression 2002.

Microarray analysis generally begins with extracting and purifying nucleic acid from a biological sample, (e.g. a biopsy or fine needle aspirate) using methods known to the art. For expression and alternative splicing analysis it may be advantageous to extract and/or purify RNA from DNA. It may further be advantageous to extract and/or purify niRNA from other forms of RNA such as tRNA and rRNA.

Purified nucleic acid may further be labeled with a fluorescent label, radionuclide, or chemical label such as biotin, digoxigenin, or digoxin for example by reverse transcription, polymerase chain reaction (PCR), ligation, chemical reaction or other techniques. The labeling may be direct or indirect which may further require a coupling stage. The coupling stage can occur before hybridization, for example, using aminoallyl-UTP and NHS amino-reactive dyes (like cyanine dyes) or after, for example, using biotin and labelled streptavidin. In one example, modified nucleotides (e.g. at a 1 aaUTP: 4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

The labeled samples may then be mixed with a hybridization solution which may contain sodium dodecyl sulfate (SDS), SSC, dextran sulfate, a blocking agent (such as COT1 DNA, salmon sperm DNA, calf thymus DNA, PolyA or PolyT), Denhardt's solution, formamine, or a combination thereof.

A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single DNA strands and then hybridized to the target DNA.

To detect hybridization of the probe to its target sequence, the probe is tagged (or labeled) with a molecular marker; commonly used markers are 32P or Digoxigenin, which is nonradioactive antibody-based marker. DNA sequences or RNA transcripts that have moderate to high sequence complementarity (e.g. at least 70%, 80%, 90%, 95%, 96%, 97%, 98%, 99%, or more complementarity) to the probe are then detected by visualizing the hybridized probe via autoradiography or other imaging techniques. Detection of sequences with moderate or high complementarity depends on how stringent the hybridization conditions were applied; high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized.

A mix comprising target nucleic acid to be hybridized to probes on an array may be denatured by heat or chemical means and added to a port in a microarray. The holes may then be sealed and the microarray hybridized, for example, in a hybridization oven, where the microarray is mixed by rotation, or in a mixer. After an overnight hybridization, non-specific binding may be washed off (e.g. with SDS and SSC). The microarray may then be dried and scanned in a machine comprising a laser that excites the dye and a detector that measures emission by the dye. The image may be overlaid with a template grid and the intensities of the features (e.g. a feature comprising several pixels) may be quantified.

Various kits may be used for the amplification of nucleic acid and probe generation of the subject methods. Examples of kit that may be used in the present invention include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol may be used for qPCR, sample archiving, fragmentation, and labeling. The amplified cDNA may be fragmented and labeled in less than two hours for GeneChip™ 3' expression array analysis using NuGEN's FL-Ovation™ cDNA Biotin Module V2. For analysis using Affymetrix GeneChip™ Exon and Gene ST arrays, the amplified cDNA may be used with the WT-Ovation Exon Module, then fragmented and labeled using the FL-Ovation™ cDNA Biotin Module V2. For analysis on Agilent arrays, the amplified cDNA may be fragmented and labeled using NuGEN's FL-Ovation™ cDNA Fluorescent Module.

In some embodiments, Ambion WT-expression kit may be used. Ambion WT-expression kit allows amplification of total RNA directly without a separate ribosomal RNA (rRNA) depletion step. With the Ambion™ WT Expression Kit, samples as small as 50 ng of total RNA may be analyzed on Affymetrix™ GeneChip™ Human, Mouse, and Rat Exon and Gene 1.0 ST Arrays. In addition to the lower input RNA requirement and high concordance between the Affymetrix™ method and TaqMan™ real-time PCR data, the Ambion™ WT Expression Kit provides a significant increase in sensitivity. For example, a greater number of probe sets detected above background may be obtained at the exon level with the Ambion™ WT Expression Kit as a result of an increased signal-to-noise ratio. Ambion™ expression kit may be used in combination with additional Affymetrix labeling kit. In some embodiments, AmpTec Trinucleotide Nano mRNA Amplification kit (6299-A15) may be used in the subject methods. The ExpressArt™ TRinucleotide mRNA amplification Nano kit is suitable for a wide range, from 1 ng to 700 ng of input total RNA. According to the amount of input total RNA and the required yields of aRNA, it may be used for 1-round (input >300 ng total RNA) or 2-rounds (minimal input amount 1 ng total RNA), with aRNA yields in the range of >10 μg. AmpTec's proprietary TRinucleotide priming technology results in preferential amplification of mRNAs (independent of the universal eukaryotic 3'-poly(A)-sequence), combined with selection against rRNAs. More information on AmpTec Trinucleotide Nao mRNA Amplification kit may be obtained at amp-tec.com/products.htm. This kit may be used in combination with cDNA conversion kit and Affymetrix labeling kit.

The raw data may then be normalized, for example, by subtracting the background intensity and then dividing the intensities making either the total intensity of the features on each channel equal or the intensities of a reference gene and then the t-value for all the intensities may be calculated. More sophisticated methods, include z-ratio, loess and lowess regression and RMA (robust multichip analysis), such as for Affymetrix chips.

In some embodiments, the above described methods may be used for determining transcript expression levels for training (e.g., using a classifier training module) a classifier to differentiate whether a subject is a smoker or non-smoker. In some embodiments, the above described methods may be used for determining transcript expression levels for training (e.g., using a classifier training module) a classifier to differentiate whether a subject has cancer or no cancer, e.g., based upon such expression levels in a sample comprising cells harvested from a nasal epithelial cell sample.

The presently described gene expression profile can also be used to screen for subjects who are susceptible to or otherwise at risk for developing lung cancer. For example, a current smoker of advanced age (e.g., 70 years old) may be at an increased risk for developing lung cancer and may represent an ideal candidate for the assays and methods disclosed herein. Moreover, the early detection of lung cancer in such a subject may improve the subject's overall survival. Accordingly, in certain aspects, the assays and methods disclosed herein are performed or otherwise comprise an analysis of the subject's clinical risk factors for developing cancer. For example, one or more clinical risk factors selected from the group consisting of advanced age (e.g., age greater than about 40 years, 50 years, 55 years, 60 years, 65 years, 70 years, 75 years, 80 years, 85 years, 90 years or more), smoking status, the presence of a lung nodule greater than 3 cm on CT scan, the lesion or nodule location (e.g., centrally located, peripherally located or both) and the time since the subject quit smoking. In certain embodiments, the assays and methods disclosed herein further comprise a step of considering the presence of any such clinical risk factors to inform the determination of whether the subject has lung cancer or is at risk of developing lung cancer.

As used herein, a "subject" means a human or animal. Usually the animal is a vertebrate such as a primate, rodent, domestic animal or game animal. In certain embodiments, the subject is a mammal (e.g., a primate or a human). In particular embodiments, the subject is a human. The subject may be an infant, a toddler, a child, a young adult, an adult or a geriatric. The subject may be a smoker, a former smoker or a non-smoker. The subject may have a personal or family history of cancer. The subject may have a cancer-free personal or family history. The subject may exhibit one or more symptoms of lung cancer or other lung disorder (e.g., emphysema, COPD). For example, the subject may have a new or persistent cough, worsening of an existing chronic cough, blood in the sputum, persistent bronchitis or repeated respiratory infections, chest pain, unexplained weight loss and/or fatigue, or breathing difficulties such as shortness of breath or wheezing. The subject may have a lesion, which may be observable by computer-aided tomography or chest X-ray. The subject may be an individual who has undergone a bronchoscopy or who has been identified as a candidate for bronchoscopy (e.g., because of the presence of a detectable lesion or suspicious imaging result). The subject may be an individual who has undergone an indeterminate or non-diagnostic bronchoscopy. The subject may be an individual who has undergone an indeterminate or non-diagnostic bronchoscopy and who has been recommended to proceed with an invasive lung procedure (e.g., transthoracic needle aspiration, mediastinoscopy, lobectomy, or thoracotomy) based upon the indeterminate or non-diagnostic bronchoscopy. The terms, "patient" and "subject" are used interchangeably herein. In some embodiments, the subject is at risk for developing lung cancer. In some embodiments, the subject has lung cancer and the assays and methods disclosed herein may be used to monitor the progression of the subject's disease or to monitor the efficacy of one or more treatment regimens.

In certain aspects, the methods and assays disclosed herein are useful for determining a treatment course for a subject. For example, such methods and assays may involve determining the expression levels of one or more genes (e.g., one or more of the genes set forth in Table 12 or Table 21, or one or more or all of the genes set forth in Table 13) in a biological sample obtained from the subject, and determining a treatment course for the subject based on the expression profile of such one or more genes. In some embodiments, the treatment course is determined based on a lung cancer risk-score derived from the expression levels of the one or more genes analyzed. The subject may be identified as a candidate for a lung cancer therapy based on an expression profile that indicates the subject has a relatively high likelihood of having lung cancer. The subject may be identified as a candidate for an invasive lung procedure (e.g., transthoracic needle aspiration, mediastinoscopy, lobectomy, or thoracotomy) based on an expression profile that indicates the subject has a relatively high likelihood of having lung cancer (e.g., greater than 60%, greater than 70%, greater than 80%, greater than 90%). In certain aspects, a relatively high likelihood of having lung cancer means greater than about a 65% chance of having lung cancer. In certain aspects, a relatively high likelihood of having lung cancer means greater than about a 70% chance of having lung cancer. In certain aspects, a relatively high likelihood of having lung cancer means greater than about a 75% chance of having lung cancer. In certain aspects, a relatively high likelihood of having lung cancer means greater than about an 80-85% chance of having lung cancer. The subject may be identified as not being a candidate for a lung cancer therapy or an invasive lung procedure based on an expression profile that indicates the subject has a relatively low likelihood (e.g., less than 50%, less than 40%, less than 30%, less than 20%) of having lung cancer. In certain aspects, a relatively low likelihood of having lung cancer means less than about a 35% chance of having lung cancer. In certain aspects, a relatively low likelihood of having lung cancer means less than about a 30% chance of having lung cancer. In certain aspects, a relatively low likelihood of having lung cancer means less than about a 25% chance of having lung cancer. In certain aspects, a relatively low likelihood of having lung cancer means less than about a 35% chance of having lung cancer. In certain aspects, a relatively low likelihood of having lung cancer means less than about a 20-25% chance of having lung cancer. Accordingly, in certain aspects of the present inventions, if the methods disclosed herein are indicative of the subject having lung cancer or of being at risk of developing lung cancer, such methods may comprise a further step of treating the subject (e.g., administering to the subject a treatment comprising one or more of chemotherapy, radiation therapy, immunotherapy, surgical intervention and combinations thereof).

In certain aspects, if the methods and assays disclosed herein are indicative of a subject being at a higher risk of having or developing lung cancer, the subject may be subjected to more invasive monitoring, such as a direct tissue sampling or biopsy of the nodule, under the presumption that the positive test indicates a higher likelihood of the nodule is a cancer. Alternatively, on the basis of the methods and assays disclosed herein being indicative of a subject's higher risk of having or developing lung cancer, in certain embodiments an appropriate therapeutic regimen (e.g., chemotherapy or radiation therapy) may be administered to the subject. Conversely, in those instances where the methods and assays disclosed herein are indicative of a subject having a reduced risk of developing lung cancer, then in certain aspects the subject may be subjected to further confirmatory testing, such as further imaging surveillance (e.g., a repeat CT scan to monitor whether the nodule grows or changes in appearance before doing a more invasive procedure), or a determination made to withhold a particular treatment (e.g., chemotherapy or radiation therapy) on the basis of the subject's favorable or reduced risk of having or developing lung cancer. In some embodiments, the assays and methods disclosed herein may be used to confirm the results or findings from a more invasive procedure, such as direct tissue sampling or biopsy. For example, in certain aspects the assays and methods disclosed herein may be used to confirm or monitor the benign status of a previously biopsied nodule or lesion.

In some embodiments, the methods and assays disclosed herein are useful for determining a treatment course for a subject that has undergone an indeterminate or non-diagnostic bronchoscopy does not have lung cancer, wherein the method comprises determining the expression levels of one or more genes (e.g., one or more of the genes set forth in Table 12 or Table 21, or one or more or all of the genes set forth in Table 13) in a sample of nasal epithelial cells obtained from the subject, and determining whether the subject that has undergone an indeterminate or non-diagnostic bronchoscopy does or does not have lung cancer or is not at risk of developing lung cancer. In some such embodiments, the method comprises determining a lung cancer risk-score derived from the expression levels of the one or more genes analyzed. In particular embodiments, the subject that has undergone an indeterminate or non-diagnostic bronchoscopy would have typically been identified as being a candidate for an invasive lung procedure (e.g., transthoracic needle aspiration, mediastinoscopy, lobectomy, or thoracotomy) based upon such indeterminate of non-diagnostic bronchoscopy result, but the subject is instead identified as being a candidate for a non-invasive procedure (e.g., monitoring by CT scan) because the subjects expression levels of the one or more genes (e.g., one or more of the genes set forth in Table 12 or Table 21, or one or more or all of the genes set forth in Table 13) in the sample of nasal epithelial cells obtained from the subject indicates that the subject has a low risk of having lung cancer (e.g., in some embodiments the instant method indicates that the subject has a greater than 60% chance of not having cancer, or a greater than 70%, 80%, or greater than 90% chance of not having cancer). In some embodiments, the subject may be identified as a candidate for an invasive lung cancer therapy based on an expression profile that indicates the subject has a relatively high likelihood of having lung cancer (e.g., in some embodiments the instant method indicates that the subject has a greater than 60% chance of having cancer, or a greater than 70%, 80%, or greater than 90% chance of having cancer). Accordingly, in certain aspects of the present inventions, if the methods disclosed herein are indicative of the subject having lung cancer or of being at risk of developing lung cancer, such methods may comprise a further step of treating the subject (e.g., administering to the subject a treatment comprising one or more of chemotherapy, radiation therapy, immunotherapy, surgical intervention and combinations thereof).

In some cases, an expression profile is obtained and the subject is not indicated as being in the high risk or the low risk categories. In some embodiments, a health care provider may elect to monitor the subject and repeat the assays or methods at one or more later points in time, or undertake further diagnostics procedures to rule out lung cancer, or make a determination that cancer is present, soon after the subject's lung cancer risk determination was made. Also contemplated herein is the inclusion of one or more of the genes and/or transcripts presented in, for example, Table 5, Table 6, Table 12, Table 13, Table 14, Table 15 or Table 21, into a composition or a system for detecting lung cancer in a subject. For example, any one or more genes and or gene transcripts from Table 12, Table 13 or Table 21 may be added as a lung cancer marker for a gene expression analysis. In some aspects, the present inventions relate to compositions that may be used to determine the expression profile of one or more genes from a subject's biological sample comprising nasal epithelial cells. For example, compositions are provided that consist essentially of nucleic acid probes that specifically hybridize with one or more genes set forth in Table 12, Table 13 or Table 21. These compositions may also include probes that specifically hybridize with one or more control genes and may further comprise appropriate buffers, salts or detection reagents. In certain embodiments, such probes may be fixed directly or indirectly to a solid support (e.g., a glass, plastic or silicon chip) or a bead (e.g., a magnetic bead).

The compositions described herein may be assembled into diagnostic or research kits to facilitate their use in one or more diagnostic or research applications. In some embodiments, such kits and diagnostic compositions are provided that comprise one or more probes capable of specifically hybridizing to up to 5, up to 10, up to 25, up to 50, up to 100, up to 200, up to 300, up to 400, up to 500 or up to 535 genes set forth in Table 12, Table 13 or Table 21 or their expression products (e.g., mRNA). In some embodiments, each of the nucleic acid probes specifically hybridizes with one or more genes selected from those genes set forth in Table 12, Table 13 or Table 21, or with a nucleic acid having a sequence complementary to such genes. In some aspects, each of at least 2, at least 3, at least 4, at least 5, at least 6, at least 7, at least 8, at least 9, at least 10, or at least 20 of the probes specifically hybridizes with one or more genes selected from group of set forth in Table 12, Table 13 or Table 21, or with a nucleic acid having a sequence complementary to such genes.

A kit may include one or more containers housing one or more of the components provided in this disclosure and instructions for use. Specifically, such kits may include one or more compositions described herein, along with instructions describing the intended application and the proper use and/or disposition of these compositions. Kits may contain the components in appropriate concentrations or quantities for running various experiments.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Previous work from our lab has shown that bronchial and nasal epithelium exhibit a common physiological response to tobacco smoke exposure (Zhang, et al., Phys. Gen. 2011). Given this relationship and the demonstrated utility of bronchial gene expression as a diagnostic marker of lung cancer, the present inventors sought to test the hypothesis that the cancer-associated expression profiles observed in the bronchial airways might also be detectable in nasal epithelium. Detecting the cancer-associated airway field of injury via nasal epithelium would offer a faster, non-invasive and cheaper alternative to sampling bronchial epithelium, and thereby expand the clinical settings where airway gene expression would have utility in evaluating patients for lung cancer.

In the following studies, the present inventors identified genes with cancer-associated expression profiles in nasal epithelium using samples obtained from current and former smokers undergoing bronchoscopy for clinical suspicion of lung cancer as part of the Airway Epithelium Gene Expression in the Diagnosis of Lung Cancer (AEGIS) clinical trials. The inventors demonstrated that the cancer-associated field of injury observed in bronchial epithelium extended to the nose and that nasal epithelial gene expression adds information about lung cancer that is distinct from clinical risk factors. These findings suggest that nasal gene expression may be useful in determining the cancer status of indeterminate pulmonary nodules.

Example 1—Lung Cancer-Associated Gene Expression in Nasal Epithelium

To identify genes whose expression is associated with lung cancer status in nasal epithelium and to compare the relationship between nasal and bronchial cancer-associated gene expression, the present inventors used existing microarray data from 299 bronchial epithelium samples from patients in the AEGIS clinical trials (Whitney, et al., BMC Med Gen 2015) and generated novel microarray data from 554 nasal epithelium samples obtained from patients in the same trials. All samples were collected from consenting patients who were undergoing bronchoscopy for clinical suspicion on lung cancer. 424 nasal samples were collected from patients enrolled in the AEGIS-1 trial and 130 were from patients in the AEGIS-2 trial (FIG. 4). Thirty one patients from the AEGIS-1 cohort had an indeterminate cancer diagnosis or were lost to follow up and were removed from the study. The present inventors additionally removed 18 microarray samples from the AEGIS-1 dataset that did not meet minimum quality standards (Table 11). No samples were removed from the AEGIS-2 dataset. The remaining 375 samples from the AEGIS-1 cohort were used as a training set in which all data analyses and model building were performed, while the 130 samples from the AEGIS-2 cohort were used solely to validate the predictive models described herein (Table 1, below). The distribution of cancer stages was slightly skewed toward later-stage cancers in the validation set (Table 7). Lung cancer patients tended to have larger nodules than patients with benign diagnoses in both the training and validation sets (P<0.001 for both comparisons) (Table 8) while patient age was statistically significantly higher among cancer patients in the training set (P<0.001). The gene expression data from these samples has been deposited in the NCBI Gene Expression Omnibus under accession number GSE80796. The nasal samples were selected from a larger pool of banked tissue samples and were well balanced for clinical covariates between cancer and benign classes (see, Table 1, below). The cases and controls whose samples were used in the training set varied by both age (p=0.0002) and mass size (p=1.4e-12), while in the test set they varied only by mass size (p=3.8e-08).

Figures 2A, 2B:
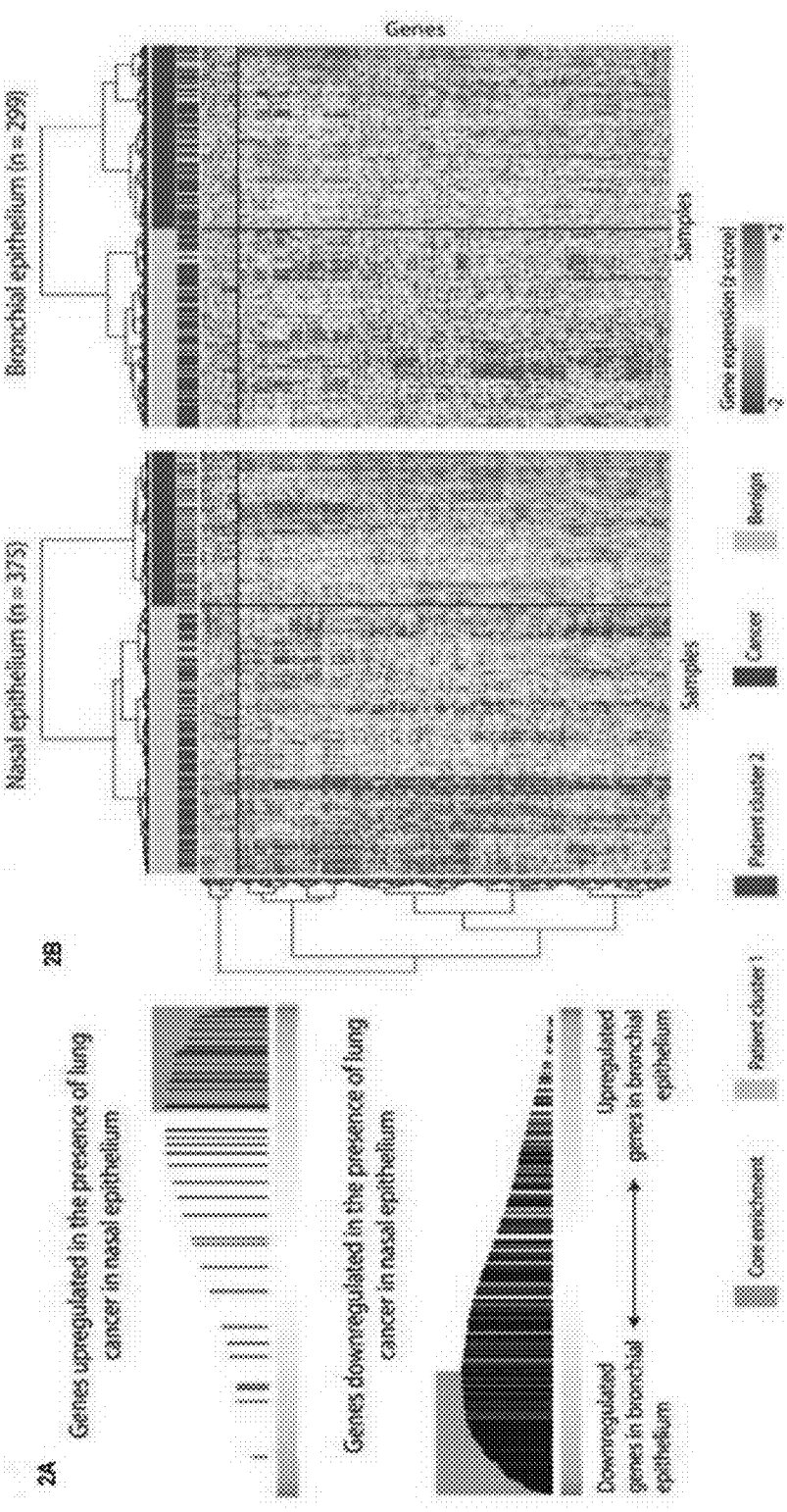
FIGS. 2A-2B demonstrate the concordance between cancer-associated gene expression in bronchial and nasal epithelium.

Differential expression analysis via linear modeling revealed 535 genes that were significantly associated with cancer status in our training set (p<0.001), as illustrated in FIG. 1 (see, Table 21, below). Of these, 43 genes were upregulated in cancer patients compared to controls, while 492 were down-regulated, but there was heterogeneity in the expression of these genes within the cases and controls. Unsupervised hierarchical clustering separated the samples into two primary clusters, as depicted in FIG. 1. The distribution of cases and controls was significantly skewed between the two patient clusters (p=0.0002; FIG. 1 and FIGS. 2A-2B), with Patient Cluster 1 enriched for patients with lung cancer and Patient Cluster 2 enriched for controls (Table 12).

Several distinct patterns of gene co-expression were also observed within these 535 genes and consensus clustering identified four distinct co-expression clusters (Table 12). The smallest of the four clusters contained 43 genes that were up-regulated in samples from patients with cancer relative to controls. The other three clusters were down-regulated in patients with cancer relative to controls (FIG. 1). Genes that were downregulated in patients with lung cancer were enriched for genes associated with DNA damage, regulation of apoptosis, and processes involved in immune system activation including the interferon-gamma signaling pathway and antigen presentation (see, Table 2 below). Among genes that were upregulated in lung cancer patients, the present inventors found enrichment for genes involved in endocytosis and ion transport (see, Table 2 below). A complete list of the 535 genes and their respective cluster memberships is provided in Table 12, below.

To summarize the behavior of each cluster, the average expression of all genes in a cluster was computed for each sample. Each of the four cancer cluster means was strongly associated with cancer status (p<0.001), as shown in Table 2, below. The present inventors assessed the gene functions enriched in each of these four clusters using the Reactome and GO databases accessed through the web-based program EnrichR (Chen, et al., 2013 BMC Bioinfo). A complete list of statistically significantly enriched pathways and GO categories (FDR<0.05) is shown in Tables 13, 22 and 23, below. Clusters 1, 2, and 3 were enriched for genes involved in the regulation of apoptosis, immune system signaling, and xenobiotic detoxification, respectively. Cluster 4 was enriched for genes involved in ion transport.

Figure 5:
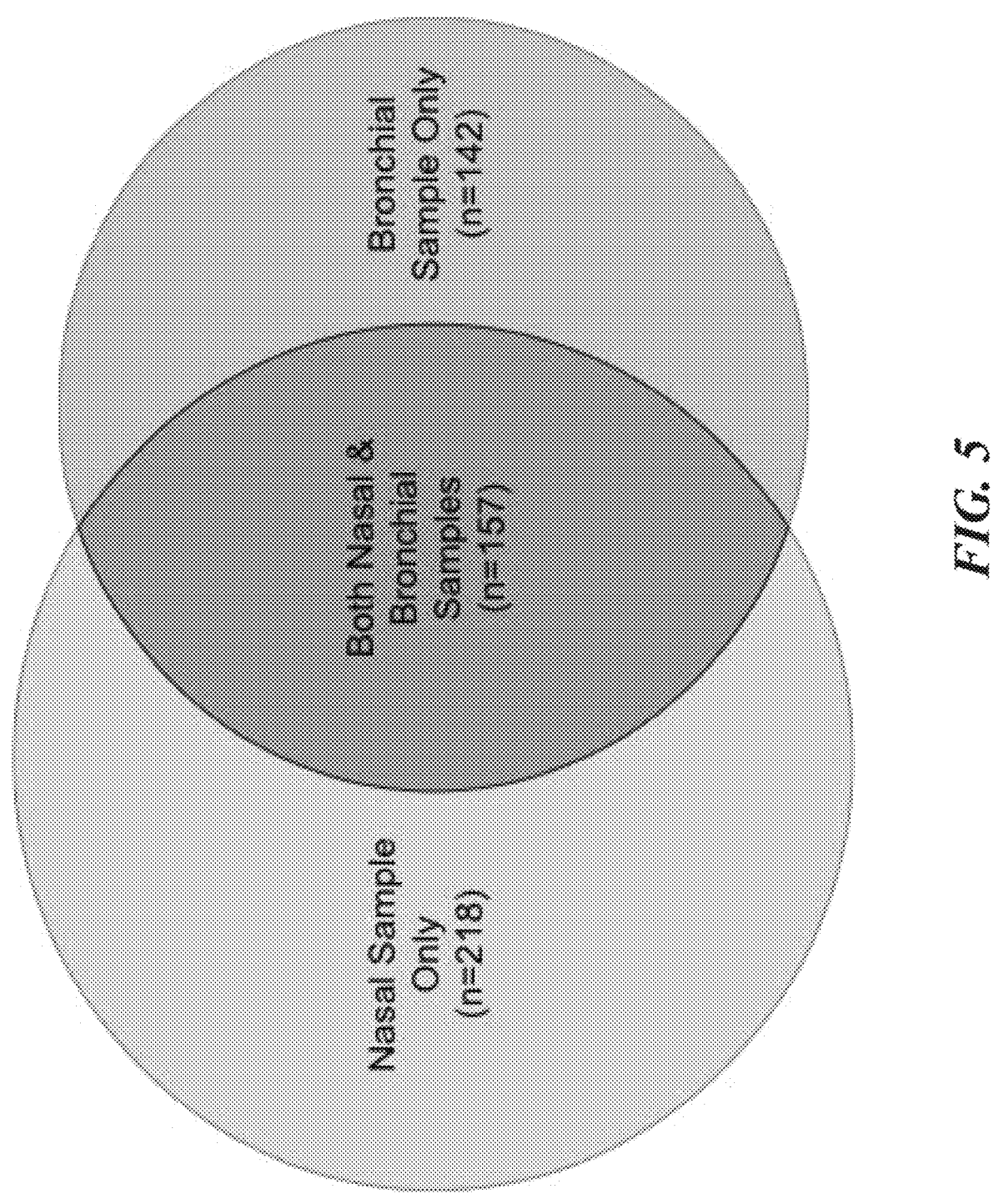
FIG. 5 depicts the distribution of matched AEGIS-1 nasal and bronchial epithelial samples. Of the 375 patients in the nasal training set, 157 had a matched bronchial epithelium sample profiles as part of the study by Whitney et. al. The remaining 218 patients only had a nasal sample profiled as part of this study. The clinical model was derived using the union set of these samples (n=517).
Figure 6:
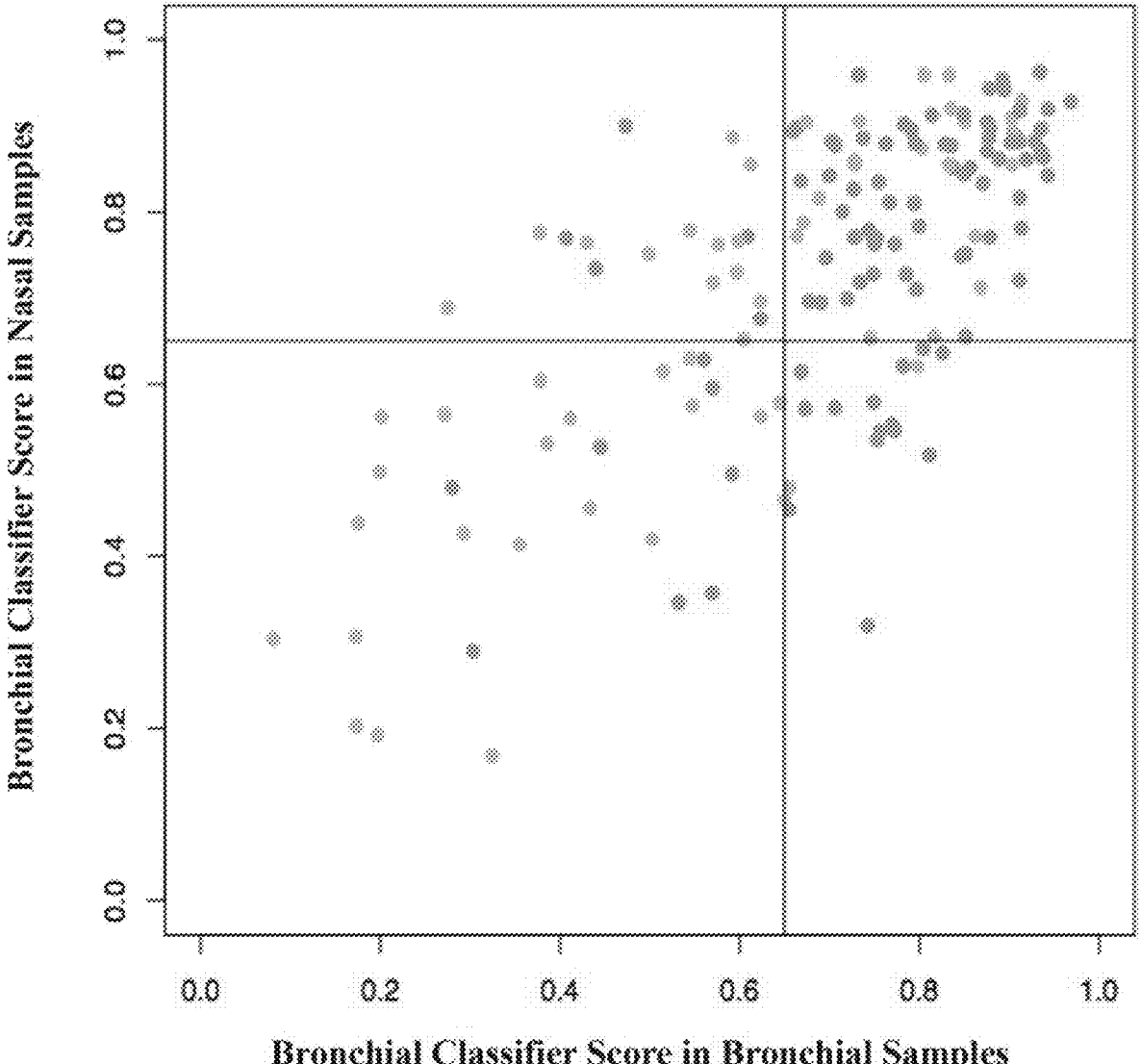
FIG. 6 illustrates the correlation of bronchial genomic classifier in matched nasal and bronchial epithelium samples. Bronchial genomic classifier scores in matched nasal (y-axis) and bronchial (x-axis) samples (n=157). The scores from both tissues were statistically significantly correlated (R=70, p<0.001 by a two-sided Pearson's product-moment correlation test). The vertical and horizontal lines indicate the cut-point for binary classification reported by Whitney et al. Cancer samples are shown in green and benign samples are shown in grey.

Example 2—Similarities in Cancer-Associated Gene Expression Changes Between Nasal and Bronchial Epithelium Given the strong concordance in smoking-related gene expression between nasal and bronchial epithelium, the present inventors next sought to determine if a shared pattern of cancer-related gene expression might exist between the nose and bronchus by leveraging microarray data from 299 bronchial epithelium samples obtained from AEGIS-1 patients (Whitney, et al., *BMC Medical Genomics*). One hundred and fifty-seven of the 299 bronchial samples came from the same patients as those in our nasal training set (Table 9 and FIG. 5). This analysis revealed significant enrichment (p<0.001) of both nasal gene sets in the bronchial ranked list, suggesting that the gene expression differences associated with the presence of lung cancer in nasal epithelium were also significantly concordantly altered in the bronchial epithelium (FIG. 2A). The expression profiles in both nasal and bronchial epithelium of the genes with the most concordant differential expression profiles between the two tissues and that contribute most strongly to this enrichment by GSEA (the "leading edge" genes) are shown in FIG. 2B and are listed in Table 21. Unsupervised hierarchical clustering of the leading edge genes organized the samples into two primary groups in each tissue. Importantly, the proportion of cancer patients in Patient Cluster 1 was significantly higher than the proportion found in Patient Cluster 2 in the bronchial (p=0.0358) samples, further demonstrating that the genes with cancer-associated expression in the nasal epithelium are part of a shared field of lung-cancer associated injury that encompasses both the nose and bronchus.

Figure 3:
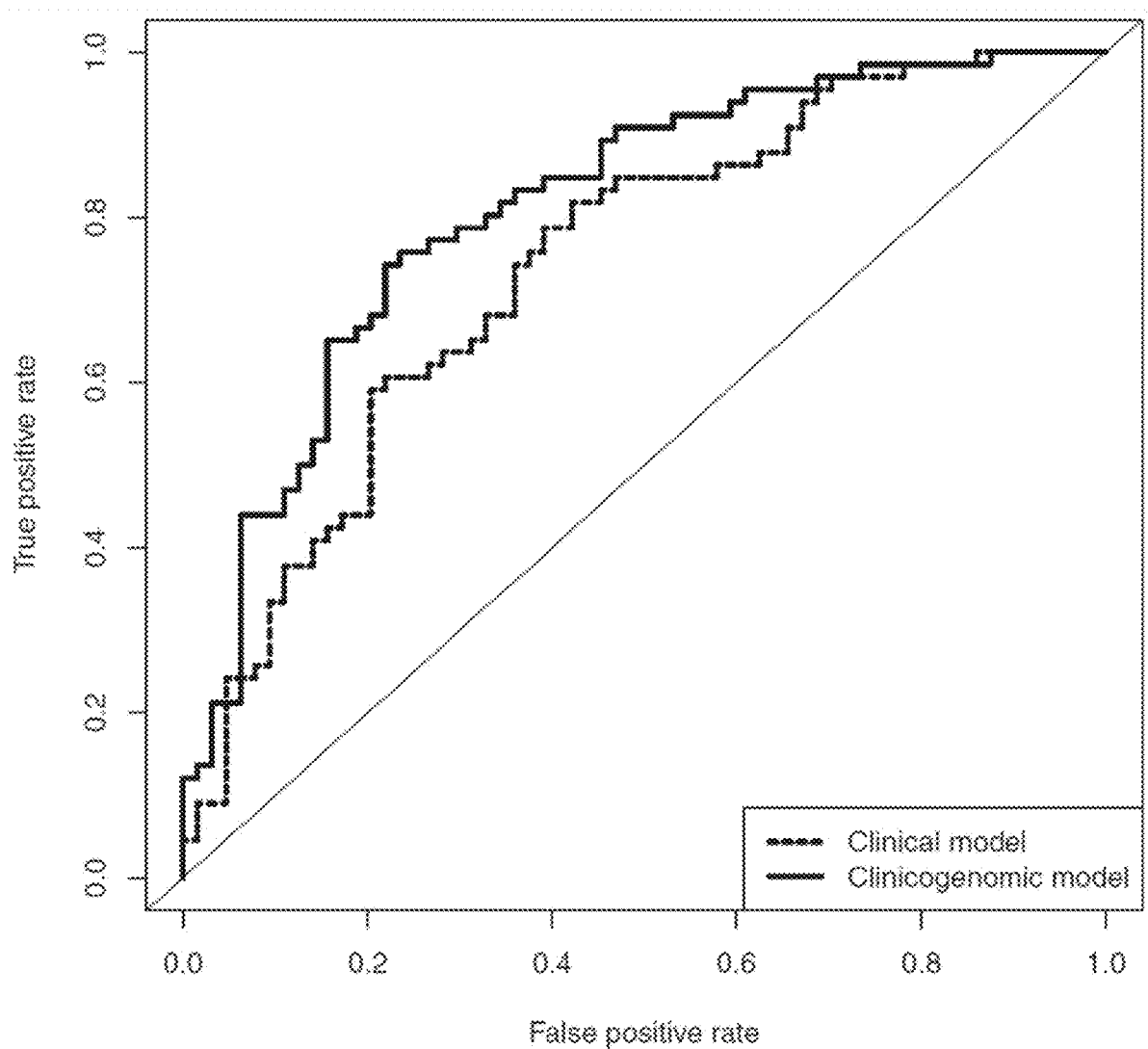
FIG. 3 shows clinicogenomic and clinical classifier performance in the validation set. Shown are the receiver operating characteristic (ROC) curves for the clinicogenomic (solid line) and clinical (dashed line) classifiers in the independent AEGIS-2 validation set. The area under the curve (AUC) was 0.81 (95% confidence interval [CI]=0.74 to 0.89) for the clinicogenomic classifier and 0.74 (95% CI=0.66 to 0.83) for the clinical classifier. The difference between ROC curves was statistically significantly different (P=0.01 by a two-sided Delong's test for correlated ROC curves).

To further corroborate the hypothesis of a shared field of lung-cancer associated injury, the present inventors also examined the nasal expression patterns of genes previously found to be associated with lung cancer in bronchial epithelium (Whitney, et al., *BMC Med Genomics* 2015). Whitney, et al. previously reported a gene-expression signature of 232 genes grouped in 11 distinct co-expression clusters from bronchial epithelial samples that were strongly associated with the presence of lung cancer. Using the mean expression values of the genes in each of these clusters as a summary of the expression of each cluster in each patient, the present inventors found that eight of these clusters were significantly associated with the presence or absence of lung cancer (p<0.05) in the training set (Table 3, below). Among the clusters most associated with cancer were genes involved in cell cycle, response to retinoic acid, and the innate immune response (Table 3). Based on the concordant expression of cancer-associated genes in bronchial and nasal epithelium, the present inventors computed the bronchial lung cancer classifier risk score (Whitney, et al., BMC Med Gen 2015) for each of the samples in our nasal training set. The risk scores computed on matched bronchial and nasal samples were highly correlated (R=0.70, p<0.001, n=157) and the classifier had a sensitivity of 81% and AUC of 0.65 (p=8.1e-13, n=375) in the entire training set (FIG. 3). Taken together, these results suggest that some of the lung-cancer associated gene expression differences are similar in nasal and bronchial epithelium.

Example 3

To determine if nasal gene expression could serve as a predictor of lung cancer status, the present inventors selected the thirty most statistically significantly differentially expressed genes (P<0.001) from among the 535 genes with cancer-associated nasal gene expression for use in a weighted-voting biomarker (Table 13). The biomarker panel size of 30 genes was chosen as the smallest number of genes that achieved maximal performance in cross-validation. This biomarker had an AUC of 0.69 (n=375, 95% CI=0.63 to 0.75, P<0.001) in cross validation in the training set. Twenty-two of the 30 genes were also statistically significantly correlated between matched bronchial and nasal samples (mean R=0.29, range=0.16-0.49, P<0.05). In order to evaluate the potential for the nasal gene expression biomarker to add to clinical risk factors for lung cancer detection, the present inventors developed a clinical risk factor model and tested whether incorporating the gene-expression biomarker enhanced its performance. The computation of the clinical factor model biomarker score was derived from the following model, $$x=(-4.65244938)+(-0.24676442*SMK)+(-1.16932025*TSQ1)+(0.12091159*TSQ2)+(0.07136355*AGE)+(1.22446427*BMS1)+(2.65403176*BMS2),$$

where, SMK=1 if former smoker and 0 if current smoker, TSQ1=1 if time since quit smoking is >=15 years, and 0 otherwise, TSQ2=1 if time since quit smoking is unknown, and 0 otherwise, AGE=the patient's numeric age in years, BMS1=1 if patient's mass size is <3 cm, and 0 otherwise, and BMS2=1 if patient's mass size is >=3 cm, and 0 otherwise; then $$\text{Clinical Factor Model Biomarker Score} = \frac{e^x}{1 + e^x},$$

where a patient is predicted cancer positive if the clinical factor model biomarker score is greater than 0.5823596, and cancer negative otherwise.

Gould previously identified smoking status, time since quit, age, and mass size as important clinical risk factors of lung cancer for patients with solitary pulmonary nodules (Gould, et al., *Chest* 2007). However, self-reported smoking status and time since quit which have been shown to be inconsistent with serum cotinine levels, especially in newly diagnosed lung cancer patients (Lewis, et al., *Biomarkers* 2003; Morales, et al., CCC 2013) and the inventors therefore used an approach similar to that described by Whitney, et al., to identify gene expression profiles that could serve as their surrogates. Two logistic regression models, including 5 and 2 genes, respectively, were derived in the training set to predict smoking status and time since quit (<15y, ≥15y) (Tables 14 and 15), where the equations associated with Tables 14 and 15 are respectively shown below, $$x = -24.1410 + (\text{Expression\_of\_Probeset\_8051583} * 0.2521) +$$
$$(\text{Expression\_of\_Probeset\_7990391} * 0.0544) +$$
$$(\text{Expression\_of\_Probeset\_7942693} * 2.5181) +$$
$$(\text{Expression\_of\_Probeset\_8080578} * 1.7191) +$$
$$(\text{Expression\_of\_Probeset\_8033257} * -0.4727)$$

and $$\text{Genomic Smoking Status Score} = \frac{e^x}{1 + e^x}; \text{ and}$$

$$x = -1.8161 + (\text{Expression\_of\_Probeset\_7990391} * 0.5726) +$$
$$(\text{Expression\_of\_Probeset\_8051583} * -0.4519)$$

and, $$\text{Genomic Time Since Quit Score} = \frac{e^x}{1 + e^x}.$$

These classifiers had AUC values of 0.89 (p<2.2e-16, n=375) and 0.75 (p=0.0001, n=319) in the training set, respectively. Consistent with what has been reported for bronchial epithelial gene expression, the present inventors could not identify a gene expression predictor of patient age (Whitney, et al., *BMC Med Gen* 2015); nor were the present inventors able to identify a robust gene expression correlate of mass size. Collectively, the gene expression correlates for smoking status and time since quit as well as numerical age and categorized mass size (<3 cm, ≥3 cm, infiltrates) were used to model lung cancer using logistic regression in the training set (Table 16) and derived from the following model, where $$x=-5.14689+(\text{Genomic\_Smoking\_Status\_Score}*1.82244)+(\text{Genomic\_Time\_Since\_Quit\_Score}*2.31235)+(\text{AGE}*0.04947)+(\text{BMS1}*1.27246)+(\text{BMS2}*2.59898),$$

where, AGE=the patient's numeric age in years, BMS1=1 if patient's mass size is <3 cm, and 0 otherwise, BMS2=1 if patient's mass size is >=3 cm, and 0 otherwise, and $$\text{Clinical Risk Factors with Genomic Correlates Model Score} = \frac{e^x}{1+e^x},$$

where a patient is predicted cancer positive if clinical risk factors with genomic correlates model score is greater than 0.4969356, and cancer negative otherwise.

These risk factors were further combined with the cancer-associated gene expression classifier into a single logistic regression clinicogenomic classifier, the parameters of which were also derived in the training set (Table 17) and from the following model, where, $x$=−4.1504024+(Genomic_Smoking_Status_Score*0.7534516)+(Genomic_Time_Since_Quit_Score*0.3276714)+(Genomic_Cancer_Classifier_Score*0.6629011)+(AGE*0.0452670)+(BMS1*1.3423457)+(BMS2*2.6932782), where, AGE=the patient's numeric age in years, BMS1=1 if patient's mass size is <3 cm, and 0 otherwise, BMS2=1 if patient's mass size is >=3 cm, and 0 otherwise, and $$\text{Clincogenomic with Genomic Correlates Model Score} = \frac{e^x}{1+e^x},$$

where a patient is predicted cancer positive if clinicogenomic with genomic correlates model score is greater than 0.4590236, and cancer negative otherwise.

The performance of the clinical and clinicogenomic models was evaluated using an independent set of nasal samples (n=130) from the AEGIS-2 clinical trial that were not used in the development of either classifier. The clinicogenomic model yielded an AUC of 0.80 in the validation set which was significantly higher than the AUC of 0.76 achieved by the clinical risk factor model alone (p=0.05). Operating points for binary classification in both models were chosen to achieve 50% specificity in the training set. The addition of cancer-associated gene expression to the clinical risk-factor model resulted in a significant increase in sensitivity from 0.85 to 0.94 (p=0.04) and increase in negative predictive value from 0.73 to 0.87 (Table 18). Importantly, the clinicogenomic model showed improvements in sensitivity from 63% to 88% over the clinical model in subjects with lesion size <3 cm and showed stable or improved performance in patients with lesions >3 cm or ill-defined infiltrates (Table 18). Consistently higher sensitivity was also observed with the clinicogenomic model in patients with central and/or peripheral nodules compared to the clinical model (Table 19). Furthermore, the addition of cancer-associated gene expression to clinical risk factors improved prediction sensitivity across all stages and cell types of disease (Table 20). Collectively, these data suggest that nasal gene expression captures molecular information about the likelihood of lung cancer that is independent of clinical factors and therefore has the potential to improve lung cancer detection.

Example 4

In an alternative approach, the present inventors built clinical and clinicogenomic models that used reported clinical values instead of a mixture of reported clinical values and gene-expression predicted clinical values as in Example 3. In choosing which clinical risk factors to include, the present inventors again relied on a study in which Gould et al. identified smoking status, time since quit, age, and mass size as important clinical risk factors of lung cancer for patients with solitary pulmonary nodules (Gould, et al., *Chest* 2007). Patient age, smoking status (current, former), time since quit (≤15 years, >15 years, unknown), and categorized mass size (<3 cm, ≥3 cm, infiltrates) were used to create a clinical risk factor model for lung cancer using logistic regression. The training set for this model consisted of the nasal training set used to derive the gene expression classifier as well as clinical data from an additional 142 patients from the AEGIS-1 cohort for a total training set of 517 patients for the clinical model (see, FIG. 5). A clinicogenomic logistic regression model that incorporated the clinical factors and the nasal gene expression classifier score was derived in the 375 training set samples with nasal gene expression. The genomic cancer classifier score used to calculate the clinicogenomic biomarker score was derived from the following model, Gene_1_score=−0.076842874545387*(Expression_of_probeset_8091385−10.223361024585)

Gene_2_score=−0.066812409800121*(Expression_of_probeset_8115147−10.4979919874352)

Gene_3_score=−0.0508738437722716*(Expression_of_probeset_8034420−7.74862668913246)

Gene_4_score=−0.0853002904314322*(Expression_of_probeset_8075720−6.02260696919916)

Gene_5_score=−0.0663441276969046*(Expression_of_probeset_7940775−8.60283524794079)

Gene_6_score=−0.100361459561592*(Expression_of_probeset_8125463−5.76219176807997)

Gene_7_score=−0.0731786032726885*(Expression_of_probeset_7912638−5.80836005908298)

Gene_8_score=−0.0588577574308188*(Expression_of_probeset_7978123−7.81869896068138)

Gene_9_score=−0.0291537526685959*(Expression_of_probeset_7937217−7.99754044283416)

Gene_10_score=−0.059579001469581*(Expression_of_probeset_8002133−6.76231617487145)

Gene_11_score=−0.0539204890593068*(Expression_of_probeset_8084895−9.25452952745888)

Gene_12_score=−0.0435216311590311*(Expression_of_probeset_8180166−9.66750825451152)

Gene_13_score=−0.102616463622019*(Expression_of_probeset_8179331−5.87582547195644)

Gene_14_score=−0.256702735040285*(Expression_of_probeset_8146092−6.84033653454892)

Gene_15_score=−0.0471515312903042*(Expression_of_probeset_7898115−6.1806473478809)

Gene_16_score=−0.0978767707892084*(Expression_of_probeset_8117476−6.42634821287224)

Gene_17_score=−0.112823826752702*(Expression_of_probeset_8180078−7.19373066084955)

Gene_18_score=−0.0489348626366957*(Expression_ of_probeset_8092978−10.4325518383754)

Gene_19_score=−0.042561683753686*(Expression_ of_probeset_7925876−7.26663202627375)

Gene_20_score=−0.040517314218441*(Expression_ of_probeset_7940160−8.41904220936401)

Gene_21_score=−0.0255314067182751*(Expression_ of_probeset_8076998−9.90620981343659)

Gene_22_score=−0.0298478887838912*(Expression_ of_probeset_8179041−11.3092804247355)

Gene_23_score=−0.152455958242676*(Expression_ of_probeset_8145317−4.99539634280867)

Gene_24_score=−0.0733338563077433*(Expression_ of_probeset_8180049−6.54533529834041)

Gene_25_score=−0.0563089183829938*(Expression_ of_probeset_7993195−6.13360660846907)

Gene_26_score=−0.0595673359556534*(Expression_ of_probeset_7929882−5.9425809217138)

Gene_27_score=−0.0292004329271551*(Expression_ of_probeset_8179049−10.6201119280024)

Gene_28_score=−0.0421648259067651*(Expression_ of_probeset_7947815−7.74324780382519)

Gene_29_score=−0.0815827122613575*(Expression_ of_probeset_8096070−7.28569239691227)

Gene_30_score=−0.0326333009894926*(Expression_ of_probeset_8063000− 10.9610191238719), where, Genomic Cancer Classifier Score=$Gene_{1score}$+ $Gene_{2score}$+$Gene_{3score}$+$Gene_{4score}$+$Gene_{5score}$+ $Gene_{6score}$+$Gene_{7score}$+$Gene_{8score}$+$Gene_{9score}$+ $Gene_{10score}$+$Gene_{11score}$+$Gene_{12score}$+$Gene_{13score}$+ $Gene_{14score}$+$Gene_{15score}$+$Gene_{16score}$+$Gene_{17score}$+ $Gene_{18score}$+$Gene_{19score}$+$Gene_{20score}$+$Gene_{21score}$+ $Gene_{22score}$+$Gene_{23score}$+$Gene_{24score}$+$Gene_{25score}$+ $Gene_{26score}$+$Gene_{27score}$+$Gene_{28score}$+$Gene_{29score}$+ $Gene_{30score}$ and the clinicogenomic biomarker score was derived using the following equation, $x$=(−3.56652108)+(−0.01621785*SMK)+(− 0.24792934*TSQ1)+(0.52981359*TSQ2)+ (0.04180910*AGE)+(1.29057600*BMS1)+ (2.70293937*BMS2)+ (0.68513004*Genomic_cancer_classifier_score), where SMK=1 if former smoker and 0 if current smoker, TSQ1=1 if time since quit smoking is >=15 years, and 0 otherwise, TSQ2=1 if time since quit smoking is unknown, and 0 otherwise, AGE=the patient's numeric age in years, BMS1=1 if patient's mass size is <3 cm, and 0 otherwise BMS2=1 if patient's mass size is >=3 cm, and 0 otherwise; then $$\text{Clincogenomic Model Biomarker Score} = \frac{e^x}{1+e^x},$$

where a patient is predicted cancer positive if the clinicogenomic model biomarker score is greater than 0.4673243, and cancer negative otherwise.

The performance of the clinical and clinicogenomic models was evaluated using an independent set of nasal samples (n=130) from the AEGIS-2 clinical trial that were not used in the development of the classifier. The clinicogenomic model yielded an AUC of 0.81 (95% CI=0.74 to 0.89) in the validation set, which was statistically significantly higher than the AUC of 0.74 (95% CI=0.66 to 0.83) achieved by the clinical risk-factor model alone (P=0.01) (FIG. 3). Operating points for binary classification were chosen to maximize training set sensitivity with specificity of 50% or greater for both models. The addition of cancer-associated gene expression to the clinical risk factor model increased sensitivity from 0.79 (95% CI=0.67 to 0.88) to 0.91 (95% CI=0.81 to 0.97, P=0.03) and negative predictive value from 0.73 (95% CI=0.58 to 0.84) to 0.85 (95% CI=0.69 to 0.94, P=0.03) (Table 4). The negative likelihood ratio of the clinicogenomic classifier was consistent between training (0.18; 95% CI=0.12 to 0.28) and validation (0.18; 95% CI=0.08 to 0.39) sets. Additionally, in subjects with either lesion size less than 3 cm or peripheral lesions, the clinicogenomic model had a negative predictive value of 0.85 (95% CI=0.65 to 0.96) or 0.93 (95% CI=0.66 to 1.00), respectively (Table 10).

Discussion

In the foregoing studies, the present inventors explored whether the airway field of injury in lung cancer extends to nasal epithelium and determined that there are gene expression alterations in the nasal epithelium of patients with lung cancer compared to those with benign diagnoses. It was observed that the lung cancer-associated gene expression patterns previously identified in the bronchial epithelium are highly concordant with those observed in nasal epithelium. Finally, the present inventors showed that the addition of nasal gene expression to clinical risk factors of disease improves diagnostic sensitivity and negative predictive value of a clinical factor model. These findings strengthen the "field of injury" hypothesis in which lung disease is able to influence the gene expression phenotype of normal-appearing cells throughout the airway; and perhaps more excitingly, suggest the potential for biomarkers based on nasal epithelial gene expression that could be used for lung cancer detection.

While previous studies have validated the existence of bronchial airway gene expression alterations in patients with lung cancer and demonstrated their clinical utility in lung cancer detection (Silvestri, et al. NEJM 2015), little is known about the physiological processes responsible for this "field of injury." One hypothesis for the presence of lung cancer-associated alterations in nasal and bronchial gene expression is that the subset of smokers who develop lung cancer exhibit a distinct genomic response to tobacco smoke exposure throughout all airway epithelial cells, consistent with the "etiological field effect" described by Lochhead, et al. for colon and other cancer types (Lochhead, et al., *Mod Pathol.* 2015). This paradigm suggests that the airway gene-expression signature is a risk marker for lung cancer as opposed to a direct consequence of the presence of lung cancer based on local or systemic factors produced by the tumor or its microenvironment (i.e., the "conventional field effect" defined by Lochhead, et al., *Mod Pathol.* 2015). Consistent with the etiological field effect hypothesis, the present inventors observed a concordant downregulation of genes associated with immune system activation in patients with lung cancer in both bronchial and nasal epithelium, which might suggest that an impaired immune response sets the stage for tumorigenesis in the lung microenvironment. Alternatively, despite the distance to the tumor, these cancer-associated gene expression differences may be a direct result of factors secreted by the tumor or its microenvironment, or some other consequence of the presence of the tumor consistent with the "conventional field effect" described above.

Mechanistically, it is intriguing that a number of genes with important roles in cancer-related processes are among the differentially expressed genes. Of the genes that were downregulated in patients with lung cancer, CASP10 and CD177 were among the most correlated genes between bronchial and nasal epithelium and are associated with the induction of apoptosis and activation of the immune response, respectively. The present inventors also identified a number of genes involved in the p53 pathway that were downregulated in patients with lung cancer, including BAK1, ST14, CD82, and MUC4. BAK1 is associated with the induction of apoptosis (Rosell, et al., *The Lancet* 2013; Gu, et al., *Tumor Biol.* 2014) and has been previously shown to be downregulated in the tumors of patients with non-small cell lung cancer (NSCLC) (Singhal, et al., *Lung Cancer.* 2008; 60(3):313-324.). ST14 has been described as a tumor suppressor in breast cancer and its overexpression associated with the inhibition of tumor cell migration and cell invasion (Wang, et al., *J Biol Chem.* 2009). The downregulation of CD82, which is a metastasis suppressor in prostate cancer (Dong, et al. *Science* 1995), has been shown to be correlated with poor survival in patients with lung adenocarcinoma (Adachi, et al., *Cancer Res.* 1996). MUC4, whose down-regulation has been associated with increased tumor stage and poorer overall survival, has also been shown to play an oncogenic role in multiple cancers and is a tumor suppressor in NSCLC, acting as a modifier of p53 expression (Majhi, et al., *J Thorac Oncol Off Publ Int Assoc Study Lung Cancer.* 2013).

From a clinical perspective, the present inventors found that the addition of lung cancer-associated gene expression to established clinical risk factors improved the sensitivity and negative predictive value for detecting lung cancer; these are the key performance metrics for driving potential clinical utility in this setting (e.g., allowing physicians to avoid unnecessary invasive procedures in those with benign disease). This provides the first proof of concept for the use of nasal gene expression for lung cancer detection. The present inventors elected to establish the presence of a nasal field of lung cancer-associated injury using samples from the AEGIS trial given the unique availability of matched bronchial samples, despite the fact that these patients were undergoing bronchoscopy for suspected lung cancer. The demonstration of the added value of nasal gene expression for lung cancer detection in this setting sets the stage for the development of nasal gene expression biomarkers for lung cancer in other clinical settings where bronchoscopy is not frequently used because of lesion or nodule size or location, risk of complications, or cost. In particular, it will now be of interest to develop nasal biomarkers for patients with small peripheral nodules found incidentally or via screening as our current bronchoscopy-based cohort is enriched for patients with centrally located lesions. In the clinical setting of patients with small peripheral nodules, it is envisioned that a nasal biomarker for lung cancer with a low negative likelihood ratio (on par with the NLR observed by the present inventors for the nasal biomarker in the AEGIS samples) could be used to identify nodule patients who are at low risk of malignancy and can be managed by CT surveillance.

Our demonstration of a nasal field of injury for lung cancer extends our previous work which demonstrated a smoking-induced field of injury that is highly concordant between bronchial and nasal epithelium (Zhang, et al., Phys. Gen. 2011). In this study, the present inventors present multiple lines of evidence that the lung cancer-associated field of injury detectable in bronchial airway epithelium (Whitney, et al., BMC Med Gen 2015) is similarly altered in nasal epithelium. The present inventors also demonstrated both that the genes whose expression is altered in patients with cancer are highly concordant in bronchial and nasal epithelium and that they are involved in similar biological processes including the innate immune response, response to retinoic acid, cell cycle, and xenobiotic detoxification. Furthermore, the present inventors also show that a lung cancer gene expression biomarker developed for use with bronchial gene expression data was able to distinguish patients with and without cancer when used with nasal instead of bronchial data.

Despite the similarity between bronchial and nasal cancer-associated gene expression, there were also differences identified. The present inventors found some lung-cancer associated genes and pathways that are either nasal- or bronchial-specific (e.g. the decreased expression of genes involved in apoptosis in nasal epithelium from patients with lung cancer). The present inventors also found that we were able to achieve better biomarker performance in independent nasal data when we developed and trained the biomarker using nasal data. The presence of some differences between bronchial and nasal epithelial cancer-associated gene expression was consistent with our previous findings with regard to smoking—where most genes are similarly altered in bronchial and nasal epithelium and a minority were airway-location specific (Zhang, et al., Phys. Gen. 2011). Given the concordance of gene expression in the context of both lung cancer and cigarette smoke exposure, one could envision expanding the airway field of injury concept for the monitoring and treatment of other diseases such as chronic obstructive pulmonary disease (COPD).

The importance and potential impact of the foregoing studies derive from several key strengths. First, the patients came from a large number of academic and community hospitals and reflect a variety of practice settings and different geographical locales; thus the diversity of alternative benign diagnoses is represented. Second, the training and validation sets came from two separate clinical trials, which minimized the potential for the model to depend on locally confounding variables. Third, the samples were prospectively collected and cancer status was unknown at the time of collection. Fourth, the present inventors have shown that nasal gene expression identifies a source of lung cancer risk that is independent of major clinical risk factors. Rather than serving as an alternative to bronchoscopy, the present inventors envision that a nasal biomarker for lung cancer could be used more broadly to distinguish the subset of patients who might benefit from bronchoscopy or other invasive procedures from those whose imaging abnormalities can be managed by repeat imaging.

While the sensitivity of our nasal clinicogenomic classifier was high (88%) in patients with nodules less than 3 cm in our validation set, the number of patients in that subgroup was small (n=54) and further studies are needed to both validate this performance as well as determine if similar levels of performance are attained in the broader clinical setting where this test would ultimately be used.

Second, while we found that nasal gene expression is an independent predictor of lung cancer compared to clinical factors alone, the performance of our nasal classifier was not dramatically different from a clinical factor biomarker. The present inventors hypothesized that this finding stems in large part from the cohort characteristics (the high pre-test probability of cancer making clinical factors such as nodule size very predictive of lung cancer) and that in a lower cancer prevalence setting, such as indeterminate pulmonary nodules, the relative contribution of the clinical factors might be substantially less.

The importance and impact of the foregoing studies are further emphasized by a number of key strengths. First, the samples used in the studies came from a variety of academic and community hospitals and reflect a variety of practice settings and different geographical locales. Second, the training and validation sets used came from two separate clinical trials which minimized the potential for spurious trends in the data to influence the model and result in overfitting. Third, since it is unlikely that genomic profiles would be used independently from clinical risk factors in the evaluation of indeterminate pulmonary nodules, we incorporated known clinical risk factors of lung cancer or their genomic correlates directly into our classifier. Fourth, the samples were prospectively collected and cancer status was unknown at the time of collection. Finally, we showed the potential utility of sampling nasal epithelium as a faster, cheaper, and non-invasive alternative to sampling bronchial epithelium which can be easily be obtained to evaluate patients with suspect lung cancer.

Together, the findings demonstrate the existence of a cancer-associated airway field of injury that can be non-invasively sampled using nasal epithelium and that nasal gene expression harbors unique information about the presence of cancer that is independent of standard clinical risk factors. These findings, in particular the high NPV of nasal clinicogenomic biomarker, suggest that nasal epithelial gene expression can potentially be used in lung cancer detection and may be especially useful in the management of indeterminate pulmonary nodules.

Materials and Methods

Study Design & Population

Patients were enrolled at 28 medical centers in the US, Canada and Europe as part of two prospective observational studies within the Airway Epithelium Gene Expression in the Diagnosis of Lung Cancer (AEGIS) clinical trials (registered as NCT01309087 and NCT00746759). Inclusion and exclusion criteria have been previously described (Silvestri, et al. NEJM 2015). All patients were current or former cigarette smokers (defined as having smoked at least 100 cigarettes in their lifetime) undergoing bronchoscopy as part of their diagnostic workup for clinical suspicion of lung cancer and all samples were collected prospectively prior to diagnosis. The diagnosis of cancer/no cancer in this cohort has been previously described (Silvestri, et al. NEJM 2015). From among the 1067 nasal samples collected in AEGIS-1 and AEGIS-2, we selected 554 samples for initial inclusion in this study based on RNA yield and sample quality.

Nasal Epithelial Cell Collection & RNA Processing

Nasal epithelial cells were collected by brushing the lateral aspect of the inferior turbinate with a single sterile cytology brush. Brushings were immediately placed into an RNA preservative (Qiagen RNAProtect, Cat. 76526). Nasal epithelial cells were processed to isolate RNA using Qiagen miRNeasy Mini Kits (Cat. 217004) as per the manufacturer's protocol. RNA concentration and purity were quantified using a NanoDrop ND-1000 spectrophotometer (Thermo Scientific) and RNA integrity (RIN) was assessed using the 2100 Bioanalyzer (Agilent Technologies). All samples were subsequently stored at −80° C. until processing on microarrays.

Microarray Processing

All procedures were performed as described in the GeneChip® Whole Transcript Sense Target Labeling Assay Manual (Affymetrix, Santa Clara, CA) and Ambion® WT Expression Kit Protocol (Life Technologies). In vitro transcription and cDNA fragmentation quality controls were carried out by running an mRNA Nano assay in the Agilent 2100 Bioanalyzer. The labeled fragmented DNA was hybridized to Affymetrix Gene 1.0 ST microarrays. The hybridized samples were washed and stained using Affymetrix fluidics. Microarrays were immediately scanned using Affymetrix GeneArray Scanner 3000 7G Plus (Affymetrix, Santa Clara, CA). The technical quality of the data from each sample was assessed using multiple quality metrics as described herein. Any sample that failed to achieve minimally acceptable thresholds for >3 quality metrics were excluded from further analysis. CEL files from all patient samples passing quality control were normalized using the Robust Multichip Average (RMA) algorithm (Irizzari, et al., Biostatistics 2003) and the Chip Definition File for the Affymetrix Gene 1.0 ST array provided by Affymetrix. Nasal and bronchial samples were normalized separately. ComBat (Johnson, et al., Biostats 2007) was used within each dataset to correct for microarray-processing batch effects. No covariates were included in the ComB at model.

Characterization of Cancer Associated Genes in Nasal Epithelium

Genes associated with cancer status in nasal epithelium were identified using empirical Bayes linear models (Smyth, SAGMB 2004) that corrected for smoking status, pack years, gender, age, and RIN. The most differentially expressed genes (p<0.001, n=535) were clustered using consensus hierarchical clustering (Monti et al., Machine Learning 2003, Wilkerson, et al. Bioinformatics 2010) with Pearson distance and Ward linkage. The sample dendrogram was cut to yield two groups of samples. The difference in the proportion of cancer samples to benign samples in each group was tested using a Pearson's Chi-squared test for count data. The optimal number of gene clusters was determined using the delta-area under the Cumulative Distribution Function curve as described by Monti et al. The mean of each cluster was computed and its association with cancer status was assessed using a Welch t-test. The functional enrichment of the genes in each cluster was determined using the web-based tool EnrichR (Chen, et al. 2013 BMC Bioinfo). A manual review of the literature was used to summarize the significant enrichments within each cluster into an overall cluster theme.

Pre-Ranked Gene Set Enrichment Analysis & Analysis of Core Enrichment

Gene Set Enrichment Analysis (GSEA) (Subramanian, et al. PNAS 2005) was used to determine if the genes with cancer-associated expression in nasal epithelium were concordantly enriched among the genes with cancer-associated expression in the bronchial epithelium. Briefly, the most differentially expressed genes were segregated into up-regulated and down-regulated gene sets. In bronchial epithelium samples, each gene's association with binary cancer status (1/0) was assessed using a Welch t-test. Moderated (empirical Bayes) t-statistics were computed for each gene and genes were subsequently ranked by t-statistic in the bronchial data in descending order. The pre-ranked function within the GSEA software package was then used to determine the enrichment of the two nasal gene sets among the top and bottom ranked genes in bronchial samples. Normalized enrichment scores, p-values, and FDR values were calculated using the GSEA software tool (Subramanian, et al. PNAS 2005). Genes on the leading edge of each enrichment plot (core enrichment) were identified based on the GSEA enrichment report. These genes were clustered in nasal samples using unsupervised hierarchical clustering with Ward linkage. Similar to the approach delineated above, the sample dendrogram was cut to yield two groups of samples and Pearson's Chi-squared test for count data was used to test the difference in the proportion of cancer samples to benign samples in each group.

Projection of Bronchial Clusters into Nasal Training Set

Eleven gene clusters previously identified as being associated with cancer in the bronchial epithelium (Whitney, et al. BMC Med Gen 2015) were projected into our nasal training set by taking the mean of the cluster genes per sample. The number of genes per cluster ranged from 1 to 47. The correlation of cluster means between matched bronchial and nasal samples was computed using Pearson's method. The association of each cluster mean with the presence or absence of cancer was computed using a Welch t-test.

Evaluation of the Bronchial Genomic Classifier

The bronchial genomic lung cancer classifier was implemented as previously described (Whitney, et al. BMC Med Gen 2015). The present inventors computed the classifier score for each of the bronchial and nasal samples from the AEGIS-1 clinical trial. After applying a mean-shift to the nasal data as previously described (Whitney, et al. BMC Med Gen 2015) and detailed below, the classifier score was computed for each nasal sample in the AEGIS-1 trial (n=375). The correlation of the classifier score between matched bronchial and nasal samples from the AEGIS-1 trial (n=157) was computed using Pearson's product-moment coefficient.

Derivation of Cancer Gene Expression Classifier

The 535 genes whose expression was associated with cancer status made up the initial pool of candidate genes for the lung cancer classifier. Weighted voting was chosen as the classification algorithm because of its proven utility in similar classification problems (Spira, et al. Nat Med 2007). The optimal number of genes for the classifier was determined using 100 random 80/20 splits of the training set. The number of genes that maximized the average AUC across the 100 iterations was used. The genes included in the final model were selected for, and the classifier trained, using the entire training set. Details regarding the cross-validation and gene selection processes are further described below.

Derivation of Genomic Correlates

Gene expression surrogates for smoking status (current/former) and time since quit (<15y, ≥15y) were derived as follows. Specifically, empirical Bayes t-tests were used to identify genes that were significantly associated with each variable. The top 10 most up-regulated and top 10 most down-regulated genes by t-statistic were initially selected, followed by a down-selection of genes using forward selection and the lasso in cross-validation. Methodological details regarding this procedure are outlined herein. The set of genes that maximized the average cross-validation AUC while minimizing the total number of genes in the model were included in the genomic correlate. Finally, a logistic regression model was trained to predict the variable using the selected genes.

Derivation of Clinical Risk Factor and Clinicogenomic Classifier

A clinical risk factor classifier was derived using logistic regression in the training set. This model included the genomic smoking status and time since quit classifier scores as well as age and mass size (<3 cm, ≥3 cm, infiltrates). A clinicogenomic classifier was derived in the training set using cross-validation. A penalized logistic regression model with cancer status as the dependent variable was derived using the penalized R package. Unpenalized independent variables in the model included the smoking status and time since quit genomic correlate prediction scores, patient age, and mass size. The cancer gene expression classifier prediction score was included as the only penalized independent variable in the model.

Statistical Analysis

Statistical differences in clinical covariates between patients with and without lung cancer were calculated using Fisher's exact test (categorical variables) or Welch t-test (continuous variables). Differential expression analyses were performed using linear modeling (limma R package) or Welch t-tests unless otherwise specified. For the differential expression analysis, a two-sided P value of less than 0.001 was considered evidence of statistically significant differential expression. Correlation coefficients were calculated using Pearson's product-moment coefficient. Accuracy of each model was assessed using standard measures including ROC curve AUC, sensitivity, specificity, negative predictive value (NPV), and positive predictive value (PPV). Differences between receiver operating characteristic (ROC) curve AUC were assessed using DeLong's test (DeLong, et al. Biometrics 1988) for correlated ROC curves. Operating points for binary classification were chosen as the threshold that maximized sensitivity while maintaining 50% specificity in the training set. Differences in sensitivity and specificity between models were assessed using McNemar's chi-squared test for count data (Agresti, Cat. Data Analysis 1990). Statistical differences in NPV between models were assessed using the generalized score statistic (Leisenring W, et al., *Biometrics* 2000) for paired analyses or a proportions test for unpaired analyses. All confidence intervals (CIs) were reported as two-sided binomial 95% confidence intervals. All statistical tests were two-sided, and a P value of less than 0.05 was considered statistically significant.

Cohort Selection

All samples used in this study were obtained from patients with suspect lung cancer enrolled in the AEGIS-1 and AEGIS-2 clinical trials. By nature of the inclusion criteria, these clinical trials were enriched for patients that were ultimately diagnosed with lung cancer. As a result, the present investigators were limited by the number of samples we could select that had a benign diagnosis at 1 year follow up. The inventors selected all benign samples with sufficient RNA yield after isolation and then selected cancer samples to match the clinical covariates of the benign group. As a result, the cancer and benign classes are very well balanced for the recorded clinical covariates (Table 1).

Microarray Quality Control

All analytical methods were carried out using the R statistical computing environment. The quality of each microarray CEL file was assessed using the ArrayQualityMetrics R package (Kauffmann, et al. Bioinformatics 2009). Nine metrics were computed per CEL file (6 prior to RMA normalization, and 3 post-RMA normalization and batch correction). See Table 11 for a description of each quality metric and associated thresholds used to evaluate CEL files.

Samples failing at least three quality metrics were removed from all subsequent analyses.

Low-Level Expression Filter

For differential expression analyses in nasal samples, only probesets that were expressed in at least 5% of samples were included to reduce noise and data dimensionality. Background-level expression was determined by examining the expression level of Y-chromosome genes DDX3Y, KDM5D, RPS4Y1, and USP9Y represented by probesets 8176375, 8176578, 8176624, 8177232 in female samples from the training set. Probesets whose expression level did not exceed 1.5 positive standard deviations of the mean expression of the four Y-linked genes in at least 5% of samples were not considered in the analyses.

Nasal Gene Expression Shift for the Evaluation of the Bronchial Genomic Classifier To account for the difference in gene expression intensity between bronchial and nasal tissues, the present inventors performed a gene-wise mean-shift which was estimated using nasal samples that had a matched bronchial sample in the training set in which the bronchial classifier was developed (n=157) (Whitney, et al. BMC Med Gen 2015). Specifically, the mean expression of each gene in nasal samples (n=157) was subtracted from its corresponding mean expression in bronchial samples. The difference was then added to that gene's expression level in all nasal samples. The bronchial genomic classifier was then evaluated on the mean-shifted nasal data.

Cross-Validation and Optimization of the Lung Cancer Gene Expression Classifier

The training set was randomly divided with 80% of samples belonging to an internal training set and the remaining 20% of samples belonging to an internal test set. Within each split of the data, the association of each gene's expression with cancer status was assessed using Student's t-test. The genes were ranked by absolute t-statistic and a varying number of the top-ranked genes were selected for inclusion in the weighted voting classifier. Classifiers composed of 5 to 100 genes were considered. The performance of each internally trained classifier was quantified using the AUC in the internal test set. This cross-validation procedure was repeated for 100 iterations. The AUC values across the 100 splits of the data were used to rank the models. The classifier size that maximized average cross-validation AUC while minimizing standard deviation and minimizing the number of genes in the classifier was selected as optimal. The genes included in this model were selected for using the entire training set. The final weighted voting classifier was trained using the entire training set and locked prior to evaluation in the validation set.

Derivation of Smoking and Time Since Quit Classifiers 4779 genes were significantly associated with smoking status (p<0.001). Among the top 20 most differentially expressed, 5 were selected for inclusion in a logistic regression model to optimize prediction of smoking status based on cross-validation (Table 14). Specifically, the present inventors used the lasso as a feature selection algorithm to reduce the number of genes in our final model. Using the nasal training set and top 20 genes as a starting point, we fit logistic regression models with binary smoking status (current/former) as the dependent variable and the 20 genes as independent variables using the lasso. The present inventors varied the values of the shrinkage parameter lambda to calculate the misclassification error rate in 10-fold cross-validation using the cv.glmnet function in the glmnet R package (Friedman, et al. JSS 2008). With increasing values of lambda, more genes are allowed to remain in the model.

The present inventors iterated over each value of lambda and recorded which genes were included in the models as lambda increased. Using these sets of genes, we fit ordinary logistic regression models in 10-fold cross-validation and computed the average test set AUC for each subset of genes. The subset that obtained the highest average AUC while minimizing the number of genes in the model was considered optimal and those genes were included in the final logistic regression model which was trained using the entire training set. This model was able to distinguish between current and former smokers with an AUC of 0.89 in the training set (p<2.2e-16, n=375).

An identical process was employed for the derivation of the time-since-quit classifier. Specifically, 235 genes were significantly associated with whether a patient had quit smoking less than or greater than 15 years prior to sample collection (p<0.001) in a subset of the training set with valid time since quit clinical annotation (n=319). Among the top 20 most differentially expressed genes, 2 were chosen for inclusion in the final logistic regression model with time since quit as the dependent variable and the two genes as independent variables. This model was trained to optimize the prediction of time since quit (<15y, ≥15y) based on the cross-validation method described above (Table 15). This model had an AUC of 0.75 in the training set (p=0.0001, n=319).

TABLE 1

| Clinical and demographic characteristics of patients who contributed nasal epithelial samples | | | |
|---|---|---|---|
| Characteristic | AEGIS-1 training set (n = 375) | AEGIS-2 validation set (n = 130) | P |
| Cancer Status, No.* | | | .006 |
| Lung Cancer | 243 | 66 | |
| Benign Disease | 132 | 64 | |
| Smoking Status, No.* | | | .75 |
| Current | 140 | 46 | |
| Former | 235 | 84 | |
| Sex, No.* | | | .75 |
| Male | 237 | 80 | |
| Female | 138 | 50 | |
| Cumulative smoke exposure (SD, No.), pack-y† | 39.0 (26.9, 371) | 34.8 (30.7, 130) | .17 |
| Time since quit (SD, No.), y† | 7.6 (12.9, 309) | 9.4 (13.4, 120) | .21 |
| Age (SD), y† | 59.5 (10.4) | 61.7 (11.5) | .06 |
| Lesion size, No.*,‡ | | | .89 |
| >3 cm | 171 | 59 | |
| ≤3 cm | 142 | 54 | |
| Infiltrate | 44 | 17 | |
| Unknown | 18 | 0 | |
| Lesion location, No.*,§ | | | .16 |
| Central | 134 | 55 | |
| Peripheral | 114 | 31 | |
| Central and peripheral | 100 | 44 | |
| Unknown | 27 | 0 | |
| Lung cancer histological type, No.*,‖ | | | .45 |
| Small cell | 40 | 8 | |
| Non-small cell | 200 | 58 | |
| Adenocarcinoma | 90 | 29 | |
| Squamous | 72 | 17 | |
| Large cell | 9 | 4 | |
| Not specified | 29 | 8 | |
| Unknown | 3 | 0 | |
| Diagnosis of benign condition, No.* | 105 | 34 | .13 |

TABLE 1-continued

Clinical and demographic characteristics of patients who contributed nasal epithelial samples

| Characteristic | AEGIS-1 training set (n = 375) | AEGIS-2 validation set (n = 130) | P |
|---|---|---|---|
| Infection | 36 | 7 | |
| Sarcoidosis | 21 | 12 | |
| Other | 48 | 15 | |

*P value calculated using two-sided Fisher's Exact test.
†P value calculated using two-sided Student's t test.
‡P value calculated comparing >3 cm vs ≤3 cm vs infiltrates.
§P value calculated comparing central vs peripheral vs central and peripheral.
‖P value calculated comparing non-small cell vs small cell.

TABLE 2

Functional characterization of genes with cancer-associated expression in nasal epithelium

| Genes | False discovery rate |
|---|---|
| Downregulated genes (n = 492) | |
| DNA damage | |
| Signal transduction involved in mitotic DNA integrity checkpoint (GO:1902400) | <0.001 |
| Ubiquitin-dependent degradation of Cyclin D1 (reactome) | <0.001 |
| Regulation of apoptosis (reactome) | <0.001 |
| G1/S DNA damage checkpoints (reactome) | <0.001 |
| Immune system activation | |
| Antigen presentation and processing of exogenous antigen (GO:0019884) | <0.001 |
| Interferon-gamma signaling (reactome) | <0.001 |
| Upregulated genes (n = 43) | |
| Ion transport | |
| Response to magnesium ion (GO:0032026) | 0.01 |
| Regulation of endocytosis (GO:0030100) | 0.01 |
| Positive regulation of release of calcium ion into cytosol (GO:0010524) | 0.02 |

TABLE 3

Projection of previously reported bronchial cancer gene clusters from Whitney, et al., into nasal training set

| Cluster | Function | No. of probesets | Direction in cancer | P* |
|---|---|---|---|---|
| 1† | Innate immune | 25 | Down | <.001 |
| 2† | Mitotic cell cycle | 47 | Down | .05 |
| 3 | Inflamation | 45 | Down | .83 |
| 4† | Resp. retinoic acid/cell cycle | 34 | Up | .004 |
| 5 | NA | 10 | Up | .36 |
| 6 | NA | 21 | Down | .02 |
| 7† | Submucosal gland markers | 20 | Up | .01 |
| 8 | n/a | 15 | Up | .003 |
| 9† | Xenobiotic detoxification | 7 | Down | .15 |
| 10† | Cartilaginous markers | 4 | Down | .05 |
| 11 | NA | 1 | Down | .03 |

*P value of two-sided t test measuring the difference in mean average expression of all genes in a cluster between cancer and benign nasal sample in the AEGIS-1 cohort.
†In bronchial genomic classifier described by Whitney et al. 2015

TABLE 4

Classifier performance in the validation set (n = 130).

| Biomarker performance metric | Clinical model | Clinicogenomic model | P |
|---|---|---|---|
| Area under the curve (95% CI)* | 0.74 (0.66 to 0.83) | 0.81 (0.74 to 0.89) | .01 |
| Sensitivity (85% CI)† | 0.79 (0.67 to 0.38) | 0.91 (0.81 to 0.97) | .03 |
| Specificity (95% CI)† | 0.58 (0.45 to 0.90) | 0.32 (0.39 to 0.64) | .42 |
| Negative predictive value (95% CI)‡ | 0.78 (0.58 to 0.84) | 0.85 (0.89 to 0.94) | .03 |
| Positive predictive value (95% CI)‡ | 0.66 (0.54 to 0.76) | 0.66 (0.55 to 0.76) | .97 |
| Accuracy (95% CI)§ | 0.68 (0.60 to 0.76) | 0.72 (0.63 to 0.79) | .68 |

*P value comparing models calculated using Delong's two-sided test. CI = confidence interval.
†P value comparing models calculated using McNemar's two-sided chi-square test.
‡P value comparing models calculated using two-sided generalized score statistic.
§P value comparing models calculated using two-sided Fisher Exact test.

TABLE 5

Top smoking-associated genes in nasal epithelium

| Probeset | Gene Name | P-Value | T-statistic | Probeset | Gene Name | P-Value | T-statistic |
|---|---|---|---|---|---|---|---|
| 8051583 | CYP1B1 | 9.44E−33 | 13.14626076 | 7920025 | NA | 6.17E−14 | 7.799299308 |
| 7990391 | CYP1A1 | 1.01E−31 | 12.88384277 | 7931417 | JAXMIP3 | 6.58E−14 | 7.789872847 |
| 7942693 | B3GNT6 | 3.24E−31 | 12.75410581 | 8135378 | PRKAR2B | 9.37E−14 | 7.734766749 |
| 8041540 | NA | 6.32E−24 | 10.81589499 | 8067185 | BMP7 | 1.10E−13 | 7.714188929 |
| 8092765 | MB2102 | 2.12E−33 | 10.66933402 | 7997738 | NA | 2.15E−13 | 7.614758084 |
| 8102800 | SLC7A11 | 9.53E−22 | 10.20398693 | 8059832 | NA | 2.66E−13 | 7.58290221 |
| 8080578 | CACNA2D3 | 6.89E−20 | 9.66548377 | 8029832 | CYP2A13 | 3.45E−13 | −7.544020294 |
| 8041536 | CYF1B1-AS1 | 7.01E−20 | 9.66326743 | 8075375 | SEC14L3 | 3.83E−13 | −7.526616582 |
| 8049349 | NA | 2.68E−19 | 9.491193205 | 7920178 | CRNN | 5.55E−13 | 7.47246828 |
| 8040283 | NA | 5.19E−19 | 9.405496334 | 8068413 | CBR3 | 6.16E−13 | 7.456682671 |
| 7913385 | RAP1GAP | 3.38E−48 | 9.160233486 | 6061780 | BPIFB2 | 6.35E−13 | 7.452269947 |
| 8088106 | TKT | 7.69E−18 | 9.051261889 | 7940634 | SCGB1A1 | 8.78E−13 | −7.403044462 |
| 8070579 | TTP1 | 8.34E−18 | 9.040457566 | 8011354 | TRPV3 | 9.11E−13 | 7.397434445 |
| 8134452 | BHLHA15 | 1.32E−17 | 8.978834747 | 8165538 | ENTPD8 | 1.10E−12 | 7.368905918 |
| 8149811 | NKX3-1 | 1.74E−17 | 8.942194811 | 8066493 | SLPI | 1.17E−12 | −7.358999404 |
| 7958019 | DRAM1 | 2.72E−17 | −8.882399906 | 8152042 | RNF19A | 1.28E−12 | −7.345510956 |
| 8011009 | NA | 4.40E−17 | 8.817561654 | 7996423 | FBXL8 | 1.42E−12 | 7.329306846 |
| 8103244 | RNF175 | 4.52E−17 | 8.813842102 | 8001032 | NA | 1.47E−12 | 7.324396485 |
| 8053200 | DQX1 | 4.85E−17 | 8.804194387 | 8070567 | TFF3 | 1.53E−12 | 7.318136631 |
| 7969640 | CLDN10 | 8.05E−17 | 8.735574427 | 7963313 | GALNT6 | 1.90E−12 | 7.285014072 |
| 8033257 | C3 | 1.00E−16 | 8.706025605 | 8048595 | GMPPA | 1.95E−12 | 7.281023948 |
| 8072626 | TIMP3 | 1.31E−16 | 8.669404178 | 7941214 | POLA2 | 2.21E−12 | −7.26184698 |

TABLE 5-continued

| Top smoking-associated genes in nasal epithelium | | | | | | | |
|---|---|---|---|---|---|---|---|
| Probeset | Gene Name | P-Value | T-statistic | Probeset | Gene Name | P-Value | T-statistic |
| 8165406 | NPDC1 | 1.77E−16 | 8.628299892 | 8123931 | ADTRP | 4.60E−12 | −7.148014135 |
| 7984862 | CYP1A2 | 2.47E−16 | 8.582059649 | 8061847 | BPIFA2 | 4.94E−12 | 7.136919575 |
| 7092463 | SLC9A3R2 | 2.67E−16 | 8.571682017 | 8125843 | SPDEF | 4.99E−12 | 7.13526023 |
| 7991516 | ADAMTS17 | 3.49E−16 | 8.534733027 | 8020653 | CABYR | 5.93E−12 | 7.106207007 |
| 8078403 | CMTM7 | 3.62E−16 | −8.529849006 | 8173106 | ITIH6 | 6.40E−12 | 7.096462699 |
| 8084630 | LOC44887 | 4.71E−16 | 8.493365253 | 7920146 | RPTN | 6.41E−12 | 7.096242593 |
| 7901272 | CYP4X1 | 5.53E−16 | −8.47115011 | 8022434 | NA | 7.45E−12 | 7.072503652 |
| 8013384 | NA | 6.23E−16 | 8.454612492 | 8143441 | KIAA1147 | 8.53E−12 | 7.051156474 |
| 7909946 | FAM1778 | 8.14E−16 | 8.417323126 | 7986446 | ALDH1A3 | 8.75E−12 | 7.047302473 |
| 8143749 | ZNF467 | 9.48E−16 | 8.396125375 | 7922200 | SELP | 1.06E−11 | −7.017305467 |
| 7937463 | TALDO1 | 1.35E−15 | 8.346624568 | 7920185 | LCE3D | 1.08E−11 | 7.014432665 |
| 8131074 | PDE7A | 2.16E−15 | −8.280542988 | 8095626 | NA | 1.27E−11 | 6.988403197 |
| 8100254 | SFRP2 | 2.84E−15 | 8.24214866 | 7990379 | EDC3 | 1.53E−11 | 6.958349465 |
| 8027381 | NA | 3.06E−15 | 8.731364256 | 8069553 | NRIP1 | 1.72E−11 | −6.940070269 |
| 8154295 | IL33 | 3.33E−15 | −8.219438241 | 7934896 | NA | 1.73E−12 | 6.939591135 |
| 7967544 | SCARB1 | 4.86E−15 | 8.165894689 | 8070584 | NA | 1.91E−12 | −6.923569828 |
| 8066117 | SAMMD1 | 6.77E−15 | −8.1188439 | 7942007 | LRP5 | 2.05E−11 | 6.911816552 |
| 7986838 | OCA2 | 7.98E−15 | 8.095297454 | 8128818 | WASF1 | 2.05E−11 | 6.911761175 |
| 7990138 | GRAMD2 | 9.29E−15 | −8.073622222 | 8064375 | SRXN1 | 2.31E−12 | 6.900342564 |
| 7970194 | MCF2L | 1.49E−14 | 8.005925946 | 8096617 | BANK1 | 2.39E−12 | −6.887824563 |
| 8115261 | CCDC69 | 1.56E−14 | −7.999239927 | 8019326 | PYCR1 | 2.43E−12 | 6.885218758 |
| 7979638 | GPX2 | 2.30E−14 | 7.943143325 | 7944667 | SORL1 | 2.71E−11 | 6.867419863 |
| 8069764 | NA | 2.57E−14 | 7.979904631 | 8098204 | CPE | 3.11E−12 | 6.845187685 |
| 8171433 | PIR | 3.15E−14 | 7.697651983 | 7937696 | KRTAP5-AS1 | 3.14E−11 | 6.843763116 |
| 7937749 | TNNT3 | 3.20E−14 | 7.89526945 | 8006836 | LRRC37A11P | 3.23E−11 | 6.839185743 |
| 8008789 | TMEM92 | 3.57E−14 | 7.879450091 | 8037071 | RABAC1 | 3.32E−13 | 6.834937234 |
| 8075635 | TIMP3 | 4.36E−14 | 7.850198962 | 8049799 | ANO7 | 3.45E−11 | 6.328397833 |
| 7945169 | TMEM458 | 6.06E−14 | 7.802052905 | 8040103 | ID2 | 3.46E−11 | −6.828281035 |
| 8029754 | FOXA3 | 3.55E−11 | 6.824011046 | 8009334 | CACNG4 | 3.03E−10 | 6.471254201 |
| 7996448 | NOL3 | 3.80E−11 | 6.812881537 | 8014768 | NA | 3.38E−10 | −6.452806445 |
| 8078330 | RBMS3 | 3.99E−11 | −6.804918146 | 8168081 | NA | 3.43E−10 | −6.450273709 |
| 8018264 | HID1 | 4.S8E−11 | 6.782713122 | 8104180 | AHRR | 3.57E−10 | 6.443432623 |
| 7933423 | NA | 4.72E−11 | 6.778039944 | 8038735 | KLK11 | 3.73E−10 | 6.436186186 |
| 8038747 | KLK12 | 4.84E−11 | 6.773913581 | 8083569 | TIPARP | 3.81E−10 | 6.432662897 |
| 7945680 | NA | 5.41E−11 | 6.755605977 | 7995976 | CPNE2 | 3.98E−10 | −6.425069554 |
| 7912552 | NA | 5.97E−11 | 6.739644374 | 8099476 | PROM1 | 4.26E−10 | −6.413943176 |
| 7923792 | SLC45A3 | 6.20E−11 | 6.733665835 | 7955119 | C12orf54 | 4.31E−10 | 6.411926841 |
| 8109049 | SPINK2 | 6.26E−11 | 6.731918916 | 8129937 | CITED2 | 4.34E−10 | 6.4107318 |
| 8018982 | CANT1 | 6.28E−11 | 6.731555767 | 8160521 | MOB3B | 4.39E−10 | −6.408533966 |
| 8023855 | CYB5A | 6.29E−11 | −6.731178772 | 8052269 | CCDC88A | 4.44E−10 | −6.406838489 |
| 8161044 | TPM2 | 6.86E−11 | −6.71710533 | 8068401 | CBR1 | 4.53E−10 | 6.403458275 |
| 8173083 | PCDH19 | 7.02E−11 | 6.713205189 | 8088560 | ADAMTS9 | 4.69E−10 | 6.39751647 |
| 7996430 | HSF4 | 7.18E−11 | 6.709527598 | 8173941 | TSPAN6 | 4.77E−10 | −6.394768754 |
| 8139909 | NA | 7.28E−11 | 6.707286953 | 8116651 | NA | 5.06E−10 | 6.384771502 |
| 7991283 | RHCG | 7.63E−12 | 6.699651343 | 8100701 | TMPRSS11B | 5.27E−10 | 6.37768863 |
| 7965873 | IGF1 | 7.65E−11 | 6.699237529 | 7905486 | CRCT1 | 5.29E−10 | 6.377217041 |
| 7926900 | MAP3K8 | 7.80E−11 | 6.696117595 | 7913667 | GALE | 5.44E−10 | 6.372346454 |
| 8003889 | NA | 7.85E−11 | 6.695014937 | 7895178 | NA | 5.48E−10 | 6.37122193 |
| 7960771 | CD163L1 | 9.40E−11 | 6.665441225 | 7935180 | PDLIM1 | 6.10E−10 | −6.352793486 |
| 8004271 | ACADVL | 1.01E−10 | 6.65320783 | 8079060 | VIPR1 | 7.88E−10 | 6.309154241 |
| 7962895 | FKBPX11 | 1.08E−10 | 6.642382655 | 8135933 | FAM71F2 | 8.52E−10 | 6.295722961 |
| 8132539 | DBNL | 1.11E−10 | 6.638028488 | 7961891 | BHLHE41 | 8.58E−10 | −6.294551046 |
| 8115584 | CCNJL | 1.21E−10 | 6.623778994 | 8096744 | CYP2U1 | 8.78E−10 | −6.290661637 |
| 8090420 | TPRA1 | 1.22E−10 | 6.622795154 | 8071107 | SLC25A18 | 9.07E−10 | 6.285035409 |
| 8124305 | NA | 1.23E−10 | 6.621294194 | 8155824 | TMC1 | 9.47E−10 | 6.27767347 |
| 8163063 | CTNNAL1 | 1.29E−10 | −6.613782611 | 8135601 | MET | 9.66E−10 | −6.274282012 |
| 8007112 | KRTAP4-7 | 1.41E−10 | 6.598801375 | 7991186 | NTRK3 | 1.02E−09 | 6.264066436 |
| 7952426 | VSIG2 | 1.43E−10 | 6.596120908 | 8117207 | ALDH5A1 | 1.12E−09 | −6.248138359 |
| 7957167 | TMEM19 | 1.49E−10 | −6.58984449 | 8138381 | AGR2 | 1.16E−09 | 6.24229081 |
| 8046790 | NA | 1.49E−10 | 6.589278946 | 7933933 | NA | 1.17E−09 | 6.240903303 |
| 7947110 | E2F8 | 1.57E−10 | −6.580665481 | 8073992 | PANX2 | 1.17E−09 | 6.240805704 |
| 8143247 | KIAA1549 | 1.60E−10 | 6.577764751 | 8044548 | IL36A | 1.24E−09 | 6.230878097 |
| 7943715 | ZC3H12C | 1.60E−10 | −6.577429765 | 7894476 | NA | 1.24E−09 | 6.230710063 |
| 8116653 | NA | 1.69E−10 | 6.568249673 | 8101637 | HSD17B13 | 1.34E−09 | −6.21801835 |
| 8180303 | SAA2 | 1.90E−10 | −6.549464434 | 8059111 | NA | 1.34E−09 | 6.217924345 |
| 8105523 | KIF2A | 2.08E−10 | −6.533921134 | 8034521 | HOOK2 | 1.36E−09 | 6.215767634 |
| 8033043 | FUT6 | 2.08E−10 | 6.532571092 | 8084891 | FAM43A | 1.37E−09 | 6.213873367 |
| 8140668 | SEMA3A | 2.20E−10 | −6.524747412 | 8126905 | CRISP3 | 1.39E−09 | 6.211941375 |
| 7983290 | NA | 2.22E−10 | 6.523319874 | 8081880 | ADPRH | 1.40E−09 | −6.210420773 |
| 8097030 | NA | 2.30E−10 | 6.517656031 | 8153002 | NDRG1 | 1.51E−09 | 6.197083836 |
| 7920155 | NA | 2.64E−10 | 6.494186742 | 8002303 | NQO1 | 1.51E−09 | 6.196974743 |
| 8165183 | SEC16A | 2.66E−10 | 6.432943101 | 7932765 | MPP7 | 1.53E−09 | −6.194925885 |
| 8170662 | NA | 2.82E−10 | 6.483430835 | 7992071 | MSLN | 1.56E−09 | 6.191635457 |
| 7961514 | MGP | 2.91E−10 | −6.478221997 | 7958200 | EID3 | 1.01E−09 | 6.186294105 |
| 7949383 | SYVN1 | 2.96E−10 | 6.474998698 | 8102468 | PRSS12 | 1.82E−09 | −6.164183374 |
| 7991453 | FAM174B | 2.98E−10 | 6.474227362 | 8044700 | DPP10 | 1.87E−09 | 6.159971437 |

TABLE 5-continued

Top smoking-associated genes in nasal epithelium

| Probeset | Gene Name | P-Value | T-statistic | Probeset | Gene Name | P-Value | T-statistic |
|---|---|---|---|---|---|---|---|
| 8059244 | CHPF | 3.00E-10 | 6.472743896 | 7901287 | CYP4Z1 | 1.93E-09 | -6.154421494 |
| 8152148 | UBR5 | 3.02E-10 | -6.47174233 | 8039090 | NA | 1.96E-09 | 6.151730830 |

TABLE 6

Top 200 time since quit-associated genes in nasal epithelium

| Probeset ID | Gene Name | P-Value | T-statistic | Probeset ID | Gene Name | P-Value | T-statistic |
|---|---|---|---|---|---|---|---|
| 8001583 | CYP1B1 | 1.15E-08 | -5.864698521 | 7946983 | SAA2 | 6.25E-05 | 4.058633159 |
| 7990138 | GRAMD2 | 2.32E-07 | 5.28908934 | 7984862 | CYP1A2 | 6.29E-05 | -4.057111887 |
| 7942693 | B3GNT6 | 3.53E-07 | -5.205136289 | 8119599 | PTCRA | 6.29E-05 | -4.057001867 |
| 8070579 | TFF1 | 4.34E-07 | -5.163177999 | 8097126 | PP12613 | 6.35E-05 | -4.05483528 |
| 7986838 | OCA2 | 6.23E-07 | -5.089401186 | 8104930 | SLC1A3 | 6.48E-05 | 4.049947014 |
| 8027381 | NA | 7.25E-07 | -5.058295771 | 8069764 | NA | 6.61E-05 | -4.045055536 |
| 8041540 | NA | 1.44E-06 | -4.915174076 | 8102800 | SLC7A11 | 6.68E-05 | -4.042121587 |
| 8001082 | NA | 1.44E-06 | 4.914726373 | 8072626 | TIMP3 | 6.73E-05 | 4.040625022 |
| 8078405 | CMTM7 | 1.50E-06 | 4.906436093 | 7997738 | NA | 6.76E-05 | -4.039368991 |
| 7990391 | CYP1A1 | 1.57E-06 | -4.89642192 | 8152092 | NA | 7.09E-05 | -4.02747718 |
| 8101828 | TSPAN5 | 2.48E-06 | -4.799287296 | 8060325 | DEFB132 | 7.35E-05 | -4.018764666 |
| 7901272 | CYP4X1 | 2.61E-06 | 4.787944198 | 8114898 | NA | 7.36E-05 | 4.018238782 |
| 8041536 | CYP181-AS1 | 2.78E-06 | -4.776872722 | 7907849 | IHX4 | 7.42E-05 | -4.016271342 |
| 8153002 | NDRG1 | 4.35E-06 | -4.676755458 | 8146921 | RDH10 | 7.46E-05 | -4.015106746 |
| 8014768 | NA | 6.35E-06 | 4.593299291 | 7961891 | BHLHE41 | 7.5SE-05 | 4.011832721 |
| 8023855 | CY85A | 7.21E-06 | 4.564723732 | 7995976 | CPNF2 | 7.62E-05 | 4.009555365 |
| 7940654 | SCG81A1 | 8.74E-06 | 4.521528076 | 8037071 | PA8AC1 | 7.78E-05 | -4.004631261 |
| 7909946 | FAM177B | 1.03E-05 | -4.484092157 | 8081375 | NXPB | 7.80E-05 | 4.004011589 |
| 8092765 | MB21D2 | 1.15E-05 | -4.45873449 | 8075635 | TIMP3 | 7.82E-05 | -4.003248222 |
| 8000117 | CRYM | 1.32E-05 | 4.428289/91 | 8162216 | SNC3 | 7.88E-05 | 4.001385938 |
| 8103244 | RNP175 | 1.36E-05 | -4.420878287 | 7909545 | T8AF5 | 7.92E-05 | 3.999998473 |
| 8007112 | KRTAP4-7 | 1.41E-05 | -4.41285066 | 8151074 | PDE57A | 8.74E-05 | 3.975623905 |
| 7941214 | POLA2 | 1.57E-05 | 4.38716782 | 7922174 | P5 | 8.81E-05 | 3.973635577 |
| 7920025 | NA | 1.65E-05 | -4.376220281 | 8088369 | NA | 9.38E-05 | -3.957921618 |
| 8009334 | CACNG4 | 1.97E-05 | -4.335205613 | 7928770 | CDHR1 | 9.96E-05 | -3.942750268 |
| 7961514 | MGP | 2.02E-05 | 4.329246764 | 7929373 | LGI1 | 0.000103668 | 3.932619259 |
| 3011009 | NA | 2.20E-05 | 4.309581331 | 7952436 | ESAM | 0.000106499 | 3.925816763 |
| 7958010 | DRAM1 | 2.36E-05 | 4.292941953 | 8067858 | NA | 0.000107269 | -3.923996515 |
| 8033257 | C3 | 2.46E-05 | 4.283082.198 | 7897210 | DFPB | 0.000112878 | -3.911094694 |
| 7918517 | WDR77 | 2.48E-05 | 4.281132252 | 8126905 | CRISP3 | 0.000113792 | -3.909052026 |
| 8046283 | NA | 2.65E-05 | -4.265297993 | 7904414 | NA | 0.00012457 | -3.886043558 |
| 8053200 | DQXl | 2.74E-05 | -4.257941513 | 7934896 | NA | 0.000131895 | -3.871471815 |
| 8095626 | NA | 2.83E-05 | 4.250377327 | 7965403 | LUM | 0.000132326 | 3.870638334 |
| 8180303 | SAA2 | 2.92E-05 | 4.242811469 | 7940914 | FKBP2 | 0.000132651 | 3.870011418 |
| 8028973 | CYP2A13 | 2.99E-05 | 4.236737342 | 8365932 | NA | 0.000141002 | 3.854379166 |
| 8143749 | ZNF467 | 3.09E-05 | -4.228935172 | 8117547 | PRSS16 | 0.00014542 | -3.846460061 |
| 8020878 | NA | 3.34E-05 | -4.210647807 | 8067185 | BMP7 | 0.000147035 | -3.843622904 |
| 7997500 | NA | 3.40E-05 | 4.206034939 | 7895628 | NA | 0.000148842 | -3.840481877 |
| 8128818 | WASF1 | 3.43E-05 | -4.204333192 | 8046790 | NA | 0.000149095 | -3.840044195 |
| 8115261 | CCDC69 | 3.45E-05 | 4.202475526 | 8062444 | BPI | 0.000156662 | 3.827293289 |
| 8081214 | GPR15 | 3.51E-05 | -4.19870281 | 7944431 | NA | 0.000161854 | 3.818877135 |
| 8078136 | NA | 4.35E-05 | 4.14711833 | 8066493 | SLPI | 0.000161907 | 3.81879309 |
| 8049349 | NA | 4.41E-05 | 4.143953075 | 7946977 | NA | 0.000163001 | 3.817051356 |
| 8071541 | NA | 4.49E-05 | -4.139669844 | 8130645 | PARK2 | 0.000166155 | 3.81209577 |
| 8037467 | ZNF229 | 5.00E-05 | -4.113296508 | 7983252 | NA | 0.00016955 | -3.806859517 |
| 8070584 | NA | 5.43E-05 | 4.092987565 | 8070567 | TFFF3 | 0.000172564 | -3.802293333 |
| 8162059 | SLC28A3 | 5.49E-05 | 4.090494754 | 7894196 | NA | 0.000176703 | -3.796142803 |
| 8011354 | TRPV3 | 5.71E-05 | 4.080883688 | 8075375 | SEC14L3 | 0.000180154 | 3.791119372 |
| 8131768 | PXIB | 5.78E-05 | 4.077769048 | 8036969 | CYP2A6 | 0.000195574 | 3.769726836 |
| 7896169 | NA | 5.80E-05 | 4.077200723 | 7970194 | MCF2L | 0.000202681 | -3.760397569 |
| 8174831 | CT47B1 | 0.000211917 | -3.748724945 | 8123951 | ADTRP | 0.000451665 | 3.545820491 |
| 8121437 | NA | 0.000232177 | -3.724718008 | 8128247 | BACH2 | 0.00046363 | -3.538643231 |
| 8058765 | FM1 | 0.00023511 | 3.721406760 | 7966878 | NA | 0.000463765 | 3.538562745 |
| 7916903 | USH1C | 0.000237444 | 3.718800401 | 7906988 | LOC440700 | 0.000475937 | -3.531439634 |
| 7920178 | CRNN | 0.000241145 | -3.714715447 | 8170662 | NA | 0.000479846 | -3.529188018 |
| 8119107 | NA | 0.000243721 | -3.711907406 | 7938758 | SAA1 | 0000481853 | 3.528038906 |
| 8036989 | NA | 0.000249824 | 3.705365209 | 7895743 | NA | 0.00048205 | 3.527926213 |
| 8165638 | ENTPD8 | 0.000258238 | -3.69658766 | 7901287 | CYP4Z1 | 0.000488219 | 3.524422872 |
| 8109049 | SPINK7 | 0.000261177 | -3.693584448 | 8010057 | NA | 0.000498899 | -3.513453969 |
| 7960099 | P2RX2 | 0.000261481 | -3.69327571 | 7927560 | FAM21A | 0.000499926 | 3.517886391 |
| 8072328 | SECL412 | 0.000264023 | 3.690706957 | 8120715 | NA | 0.000502377 | 3.516536417 |
| 8161368 | LOC100132167 | 0.000269317 | 3.685431484 | 8167601 | USP27X | 0.000527994 | 3.502782171 |
| 7985871 | MIR9-3 | 0.000270171 | -3.684590383 | 8115327 | SPARC | 0.000528943 | 3.502284668 |
| 8004394 | SPEM1 | 0.000278264 | -3.676733864 | 8139828 | LOC441239 | 0.000533099 | -3.500116162 |
| 7982070 | SNORD115-32 | 0.000283003 | 3.672233183 | 7926170 | DHTKD1 | 0.000535909 | 3.49865877 |
| 8082574 | TRH | 0.000286174 | -3.669261344 | 8062557 | PPP1R16B | 0.000541925 | 3.495562545 |

TABLE 6-continued

Top 200 time since quit-associated genes in nasal epithelium

| Probeset ID | Gene Name | P-Value | T-statistic | Probeset ID | Gene Name | P-Value | T-statistic |
|---|---|---|---|---|---|---|---|
| 7991186 | NTRK3 | 0.00029042 | −3.665329482 | 8078330 | RBMS3 | 0.000543871 | 3.494567757 |
| 7900540 | RIMKLA | 0.000292574 | −3.663355926 | 7983447 | SLC28A2 | 0.000543925 | 3.494540275 |
| 8080578 | CACNA2D3 | 0.000294622 | −3.661491289 | 7983290 | NA | 0.00546906 | −3.493023391 |
| 8172573 | SYP | 0.000299006 | 3.657541531 | 8116439 | SCG83A1 | 0.000550383 | 3.491263407 |
| 7922200 | SELP | 0.000301062 | 3.655708817 | 7966779 | NOS1 | 0.000553633 | −3.48962808 |
| 8088468 | NPCDR1 | 0.000304757 | 3.652442615 | 8019988 | NA | 0.000570334 | 3.481362864 |
| 7988327 | PATL2 | 0.000307476 | 3.65006304 | 8055314 | LYPD1 | 0.000575959 | 3.478630058 |
| 8075820 | CACNG2 | 0.000323566 | −3.636374828 | 8088371 | DNASE1L3 | 0.00057999 | −3.476686921 |
| 7934215 | SPOCK2 | 0.000824783 | 3.635365593 | 8044700 | DPP10 | 0.000580791 | −3.476302542 |
| 8017476 | CSH2 | 0.000326981 | 3.633551814 | 8075600 | BPIFC | 0 000581413 | 3.476004282 |
| 8173414 | SLC7A3 | 0.000330053 | −3.631036902 | 8106556 | CMYA5 | 0.000582713 | 3.475381458 |
| 8103736 | SCRG1 | 0.000331212 | −3.630093458 | 8019316 | PYCR1 | 0.000589793 | 3.472014063 |
| 8175393 | RHGEf6 | 0.000331608 | 3.62977143 | 8029754 | FOXA3 | 0.000594623 | 3.469738353 |
| 7969640 | CLDN10 | 0.000336817 | −3.625574076 | 8154295 | IL33 | 0.000595872 | 3.4691522S2 |
| 7892769 | NA | 0.000337111 | 3.625339236 | 8171917 | FTHL17 | 0.000596904 | −3.468669173 |
| 7920185 | LCE3D | 0.000348019 | 3.6167S0963 | 8095422 | STATH | 0.000598118 | 3.468101959 |
| 7931417 | JAKMIP3 | 0.000354695 | −3.61618979 | 7982052 | NA | 0.000600475 | 3.467003893 |
| 8139909 | NA | 0.000359521 | −3.607965147 | 7979658 | GPX2 | 0.000606126 | −3.464387193 |
| 7894088 | NA | 0.000364096 | −3.604543506 | 8017867 | FAM20A | 0.000613706 | 3.460912633 |
| 7914921 | NA | 0.000366732 | −3.602590392 | 8138381 | ACR2 | 0.000614997 | −3.460324637 |
| 7945680 | NA | 0.000372746 | −3.598373012 | 8081880 | ADPRH | 0.000622628 | 3.456873835 |
| 8078619 | ITGA9 | 0.000372991 | 3.598005497 | 8155824 | TMC1 | 0.000630659 | −3.453284349 |
| 8043682 | LOC653924 | 0.000374957 | −3.596580619 | 8172658 | NA | 0.000631342 | −3.452981264 |
| 8117207 | ALDH5A1 | 0.00038227 | 3.593339234 | 8062971 | NA | 0.000636581 | 3.45066517 |
| 8096617 | BANK1 | 0.000386498 | 3.588352716 | 8052269 | CCDC88A | 0.000642416 | 3.44810603 |
| 7937696 | KKTAP5-AS1 | 0.000393861 | 3.583223045 | 7953943 | GABARAPL1 | 0.000652833 | −3.443591394 |
| 8098704 | CPE | 0.000395509 | −3.582086909 | 8104180 | AHRR | 0.000655203 | −3.442574075 |
| 8076894 | MLC1 | 0.0003991 | −3.579627779 | 7934145 | LRRC20 | 0.000659983 | −3.440531661 |
| 8095870 | CCNG2 | 0.000405683 | −3.575172113 | 8032249 | ADAMTSL5 | 0.000664642 | −3.438554616 |
| 8166447 | PTCHD1 | 0.000417361 | −3.567433053 | 7938683 | OR7E14P | 0.00067819 | 3.432877519 |
| 8118995 | LHFPL5 | 0.000427736 | −3.560725901 | 7981787 | NA | 0.000687427 | −3.429067246 |
| 8097030 | NA | 0.000437767 | −3.554384169 | 8044813 | TMEM37 | 0.000703886 | 3.422395032 |
| 8072344 | NA | 0.000441594 | 3.552000856 | 8022434 | NA | 0.000732313 | −3.411207279 |
| 8155516 | LOC100132167 | 0.000450392 | 3.546594339 | 8121009 | C6orf163 | 0.000751363 | 3.403934422 |

TABLE 7

Stage data on patients diagnosed with primary lung cancer.

| Lung Cancer Stage | AEGIS-1 Training Set (n = 243) | AEGIS-2 Validation Set (n = 66) |
|---|---|---|
| Non-small cell lung cancer*, No. | 200 | 58 |
| 1a, 1b | 44 | 6 |
| 2a, 2b | 13 | 4 |
| 3a, 3b | 44 | 19 |
| 4 | 66 | 25 |
| Uncertain | 33 | 4 |
| Small cell lung cancer†, No. | 40 | 8 |
| Extensive | 18 | 8 |
| Limited | 16 | 0 |
| Uncertain | 6 | 0 |
| Unknown, No. | 3 | 0 |

*p = 0.04 by two-sided Fisher's Exact test calculated for AEGIS-1 non-small cell lung cancer stage vs AEGIS-2 non-small cell lung cancer stage
†p = 0.02 by two-sided Fisher's Exact test calculated for AEGIS-1 small cell lung cancer stage vs AEGIS-2 small cell lung cancer stage

TABLE 8

Training and validation set demographics distributed based on cancer status.

| | AEGIS-1 Training Set | | | AEGIS-2 Validation Set | | |
|---|---|---|---|---|---|---|
| Characteristic | Cancer | Benign | P* | Cancer | Benign | P* |
| Total No. | 243 | 132 | | 66 | 64 | |
| Smoking Status, No.* | | | 0.91 | | | 1.00 |

TABLE 8-continued

Training and validation set demographics distributed based on cancer status.

| | AEGIS-1 Training Set | | | AEGIS-2 Validation Set | | |
|---|---|---|---|---|---|---|
| Characteristic | Cancer | Benign | P* | Cancer | Benign | P* |
| Current | 90 | 50 | | 23 | 23 | |
| Former | 153 | 82 | | 43 | 41 | |
| Gender, No.* | | | 0.57 | | | 0.72 |
| Male | 151 | 86 | | 42 | 38 | |
| Female | 92 | 46 | | 24 | 26 | |
| Mass Size, No.* | | | <0.001 | | | <0.001 |
| ≥3 cm | 140 | 31 | | 46 | 13 | |
| <3 cm | 80 | 62 | | 16 | 38 | |
| Infiltrates | 12 | 32 | | 4 | 13 | |
| Unknown | 11 | 7 | | 0 | 0 | |
| Age, y (SD)† | 61.1 (9.5) | 56.6 (11.4) | <0.001 | 62.2 (9.6) | 61.1 (13.3) | 0.58 |
| Pack-years (SD)† | 40.7 (24.6) | 35.7 (30.5) | 0.11 | 37.9 (28.1) | 31.6 (33.1) | 0.24 |
| Time Since Quit, yr. (SD)† | 6.7 (11.5) | 8.9 (14.8) | 0.17 | 6.4 (10.6) | 12.2 (15.3) | 0.02 |
| RNA Integrity Number(SD)† | 4.4 (1.8) | 4.3 (1.9) | 0.92 | 4.7 (1.8) | 4.3 (1.9) | 0.24 |

*p-value calculated using a two-sided Fisher's Exact test to compare cancer vs. benign.
†p-value calculated using a two-sided Student t-test to compare cancer vs. benign.

TABLE 9

Clinical and demographic characteristics for patients with matched nasal and bronchial epithelial samples included in this study.

| Characteristic* | Matched Nasal Samples (n = 157) | Non-matched Nasal Samples (n = 218) |
|---|---|---|
| Cancer Status, No. | | |
| Lung Cancer | 97 | 146 |
| Benign Disease | 60 | 72 |
| Smoking Status, No. | | |
| Current | 53 | 87 |
| Former | 104 | 131 |
| Gender, No. | | |
| Male | 104 | 85 |
| Female | 53 | 133 |
| Cumulative Smoke Exposure, pack-yr (SD) | 37.8 (24.7) | 39.9 (28.4) |
| Time Since Quit, y (SD) | 8.1 (12.6) | 7.0 (13.2) |
| Age, y (SD) | 59.6 (11.2) | 59.5 (9.8) |
| Lesion Size, No. | | |
| >3 cm | 66 | 105 |
| <3 cm | 68 | 74 |

TABLE 9-continued

Clinical and demographic characteristics for patients with matched nasal and bronchial epithelial samples included in this study.

| Characteristic* | Matched Nasal Samples (n = 157) | Non-matched Nasal Samples (n = 218) |
|---|---|---|
| Infiltrate | 17 | 27 |
| Unknown | 6 | 12 |
| Lesion Location, No. | | |
| Central | 55 | 79 |
| Peripheral | 51 | 63 |
| Central and Peripheral | 42 | 58 |
| Unknown | 9 | 18 |
| Lung Cancer Histological Type, No. | | |
| Small-cell | 14 | 26 |
| Non-small-cell | 83 | 117 |
| Adenocarcinoma | 41 | 49 |
| Squamous | 30 | 42 |
| Large-cell | 3 | 5 |
| Not specified | 9 | 20 |
| Unknown | 0 | 4 |
| Diagnosis of Benign Condition, No. | | |
| Infection | 15 | 21 |
| Sarcoidosis | 11 | 10 |
| Other | 18 | 30 |

*No statistically significant differences were observed between matched and unmatched nasal samples.

TABLE 10

Comparison of clinical risk-factor model and clinicogenomic classifiers in patient subgroups stratified by lesion size and location*

| Group | All Patients | Patients with Cancer | % Sensitivity (95% CI) | | % Negative Predictive Value (95% CI) | |
|---|---|---|---|---|---|---|
| | | | Clinical Risk-Factor Model | Clinicogenomic Model | Clinical Risk-Factor Model | Clinicogenomic Model |
| All patients | 130 | 66 | 78.8 (67.0-87.9) | 90.9 (81.3-96.6) | 72.5 (58.3-84.1) | 84.6 (69.5-94.1) |
| Lesion Size | | | | | | |
| <3 cm | 54 | 16 | 50.0 (24.7-75.3) | 75.0 (47.6-92.7) | 77.1 (59.9-89.6) | 84.6 (65.1-95.6) |
| ≥3 cm | 59 | 46 | 95.6 (85.2-99.5) | 100.0 (88.7-100.0) | 0.0 (0.0-90.6) | 100.0 (1.3-100.0) |
| Infiltrates | 17 | 4 | 0.0 (0.0-71.6) | 50 (7-93) | 71.4 (41.9-91.6) | 83.3 (51.6-97.9) |
| Lesion Location | | | | | | |
| Central | 55 | 28 | 78.6 (59.0-91.7) | 92.9 (76.5-99.1) | 76.9 (56.4-91.0) | 88.2 (63.6-98.5) |
| Peripheral | 31 | 6 | 66.7 (22.2-95.7) | 83.3 (35.9-99.6) | 86.7 (59.5-98.3) | 92.9 (66.1-99.8) |
| Both | 44 | 32 | 81.2 (63.6-92.8) | 90.6 (75.0-98.0) | 40.0 (12.2-73.8) | 62.5 (24.5-91.5) |

*CI = confidence interval.

TABLE 11

| Microarray quality control metrics and thresholds | | |
|---|---|---|
| Metric | Pre/Post RMA | Threshold |
| L1 Distance Between Arrays | Pre | 353 |
| Array Intensity Distribution | Pre | 0.175 |
| Relative Log Expression | Pre | 0.162 |
| Normalized Unscaled Standard Error | Pre | 1.07 |
| MA Plot Floeffding's Statistic | Pre | 0.15 |
| Spatial Distribution of Feature Intensities | Pre | 0.108 |
| L1 Distance Between Arrays | Post | 243 |
| Array Intensity Distribution | Post | 0.0272 |
| MA Plot Hoeffding's Statistic | Post | 0.15 |

TABLE 12

| 535 cancer-associated differentially expressed genes in nasal epithelium | | | | | |
|---|---|---|---|---|---|
| Probeset | Gene Symbol | Gene Cluster | Probeset | Gene Symbol | Gene Cluster |
| 7892618 | NA | 1 | 7988124 | PPIP5K1 | 1 |
| 7892678 | NA | 1 | 7988132 | STRC | 1 |
| 7892766 | NA | 1 | 7989619 | PPIB | 1 |
| 7892947 | NA | 1 | 7991323 | PEX11A | 1 |
| 7893061 | NA | 1 | 7993223 | CLEC16A | 1 |
| 7893173 | NA | 1 | 7996725 | DU52 | 1 |
| 7893248 | NA | 1 | 7996908 | SNTB2 | 1 |
| 7893296 | NA | 1 | 7999791 | NA | 1 |
| 7893333 | NA | 1 | 8002919 | KARS | 1 |
| 7893647 | NA | 1 | 8005994 | ERAL1 | 1 |
| 7893862 | NA | 1 | 8006392 | PSMD11 | 1 |
| 7894331 | NA | 1 | 8006531 | SLFN5 | 1 |
| 7894501 | NA | 1 | 8006812 | PSMB3 | 1 |
| 7894737 | NA | 1 | 8007302 | TUBG1 | 1 |
| 7894926 | NA | 1 | 8007312 | TUBG2 | 1 |
| 7895180 | NA | 1 | 8007715 | NMT1 | 1 |
| 7895602 | NA | 1 | 8008139 | UBEZZ | 1 |
| 7895618 | NA | 1 | 8009164 | DCAF7 | 1 |
| 7896201 | NA | 1 | 8010924 | VPS53 | 1 |
| 7896651 | NA | 1 | 8011599 | ANKFY1 | 1 |
| 7901110 | AKR1A1 | 1 | 8012856 | ELAC2 | 1 |
| 7904830 | RNF115 | 1 | 8013588 | POLDIP2 | 1 |
| 7905938 | SLC50A1 | 1 | 8013641 | PIG5 | 1 |
| 7906079 | RAB25 | 1 | 8014115 | MYO1D | 1 |
| 7908147 | TSEN15 | 1 | 8014903 | NA | 1 |
| 7910416 | URB2 | 1 | 8015545 | RAB5C | 1 |
| 7912412 | MTOR | 1 | 8016099 | EFTUD2 | 1 |
| 7914563 | YARS | 1 | 8021727 | CNDP2 | 1 |
| 7914834 | PSMB2 | 1 | 8026106 | CALR | 1 |
| 7915504 | ELOVL1 | 1 | 8027876 | TMEM147 | 1 |
| 7915578 | TMEM53 | 1 | 8028705 | TIMM50 | 1 |
| 7917359 | ZNHIT6 | 1 | 8028756 | PSMC4 | 1 |
| 7920971 | C1orf85 | 1 | 8031827 | ZNFS87 | 1 |
| 7923483 | RABIF | 1 | 8033912 | DNMT1 | 1 |
| 7923929 | PIGR | 1 | 8036010 | PEPD | 1 |
| 7928630 | EIFSAL1 | 1 | 8042576 | NAGK | 1 |
| 7930031 | GBF1 | 1 | 8043100 | TMSB10 | 1 |
| 7930498 | AC5L5 | 1 | 8043197 | VAMP8 | 1 |
| 7930533 | LOC143188 | 1 | 8043937 | CNOT11 | 1 |
| 7930577 | CASP7 | 1 | 8047403 | CASP10 | 1 |
| 7931778 | PITRM1 | 1 | 8048926 | SP140L | 1 |
| 7933760 | CCDC6 | 1 | 8058914 | AAMP | 1 |
| 7934133 | PPA1 | 1 | 8059350 | AP153 | 1 |
| 7934653 | POLR3A | 1 | 8059361 | WDFY1 | 1 |
| 7934753 | NA | 1 | 8062349 | RPN2 | 1 |
| 7936284 | XPNPEP1 | 1 | 8062981 | PIGT | 1 |
| 7937217 | ECHS1 | 1 | 8063211 | NCOA3 | 1 |
| 7938834 | NAV2 | 1 | 8063369 | RNF114 | 1 |
| 7940775 | RARRES3 | 1 | 8064522 | IDH3B | 1 |
| 7944803 | VWA5A | 1 | 8065832 | TRPC4AP | 1 |
| 7950248 | FCHSD2 | 1 | 8066939 | BAGALT5 | 1 |
| 7950906 | CTSC | 1 | 8075585 | RTCB | 1 |
| 7951565 | ARHGAP20 | 1 | 8080938 | MITF | 1 |
| 7952557 | SRPR | 1 | 8086028 | GLB1 | 1 |
| 7953395 | COP57A | 1 | 8088247 | ARHGEF3 | 1 |
| 7953981 | ETV6 | 1 | 8088634 | NA | 1 |

TABLE 12-continued

| | 535 cancer-associated differentially expressed genes in nasal epithelium | | | | | |
|---|---|---|---|---|---|
| Probeset | Gene Symbol | Gene Cluster | Probeset | Gene Symbol | Gene Cluster |
| 7958828 | TRAFD1 | 1 | 8089544 | CCDC80 | 1 |
| 7959153 | COX6A1 | 1 | 8089568 | CD200R1 | 1 |
| 7962869 | DDX23 | 1 | 8091385 | CP | 1 |
| 7963187 | LIMA1 | 1 | 8091991 | NA | 1 |
| 7967175 | KDM2B | 1 | 8092169 | TNFSF10 | 1 |
| 7969794 | LOC100132099 | 1 | 8092230 | ZMAT3 | 1 |
| 7973314 | OXA1L | 1 | 8092541 | LIPH | 1 |
| 7973564 | PSME1 | 1 | 8099398 | PCGF3 | 1 |
| 7979743 | RDH11 | 1 | 8093685 | HTT | 1 |
| 7979757 | ZFYVE26 | 1 | 8095139 | SRD5A3 | 1 |
| 7980146 | NPC2 | 1 | 8098547 | NA | 1 |
| 7981824 | NA | 1 | 8102311 | CASP6 | 1 |
| 7985959 | GDPGP1 | 1 | 8103911 | IRF2 | 1 |
| 7987536 | RMDN3 | 1 | 8105077 | CARD6 | 1 |
| 8108558 | SLC35A4 | 1 | 8072735 | APOL1 | 2 |
| 8108593 | WDR55 | 1 | 8075720 | APOL2 | 2 |
| 8114145 | VDAC1 | 1 | 8082075 | DTX3L | 2 |
| 8116096 | DDX41 | 1 | 8086125 | TRANK1 | 2 |
| 8117243 | LRRC16A | 1 | 8090018 | PARP9 | 2 |
| 8117321 | TRIM38 | 1 | 8115147 | CD74 | 2 |
| 8122013 | L3MBTL3 | 1 | 8117435 | BTN3A2 | 2 |
| 8122803 | NA | 1 | 8117458 | BTN3A1 | 2 |
| 8123062 | TMEM181 | 1 | 8117476 | BTN3A3 | 2 |
| 8123800 | NA | 1 | 8117760 | HLA-F | 2 |
| 8123951 | ADTRP | 1 | 8117777 | NA | 2 |
| 8126588 | XPO5 | 1 | 8118556 | NA | 2 |
| 8126729 | NA | 1 | 8118594 | HLA-DPB1 | 2 |
| 8129254 | MAN1A1 | 1 | 8125463 | NA | 2 |
| 8131631 | HDAC9 | 1 | 8125483 | TAP2 | 2 |
| 8133690 | MDH2 | 1 | 8125993 | ETV7 | 2 |
| 8134091 | CLDN12 | 1 | 8140971 | SAMD9L | 2 |
| 8135422 | BCAP 29 | 1 | 8143327 | PARP12 | 2 |
| 8136095 | AHCYL2 | 1 | 8145317 | ADAMDEC1 | 2 |
| 8136580 | RAB19 | 1 | 8146092 | IDO1 | 2 |
| 8139392 | DDX56 | 1 | 8161964 | FRMD3 | 2 |
| 8147112 | NA | 1 | 8177732 | HLA-A | 2 |
| 8148059 | DEPTOR | 1 | 8178193 | HLA-DRA | 2 |
| 8153474 | TSTA3 | 1 | 8178205 | HLA-DQA2 | 2 |
| 8154733 | ACO1 | 1 | 8179019 | HLA-F | 2 |
| 8156770 | GALNT12 | 1 | 8179041 | NA | 2 |
| 8159249 | MRPS2 | 1 | 8179049 | HLA-J | 2 |
| 8160914 | VCP | 1 | 8179481 | HLA-DRA | 2 |
| 8163452 | FKBP15 | 1 | 8179489 | NA | 2 |
| 8165866 | STS | 1 | 8179495 | PSMB9 | 2 |
| 8168762 | CSTF2 | 1 | 8179519 | HLA-DPB1 | 2 |
| 8169249 | MID2 | 1 | 8179731 | NA | 2 |
| 8170882 | ATP6AP1 | 1 | 8180003 | NA | 2 |
| 8173979 | NOX1 | 1 | 8180022 | NA | 2 |
| 8173999 | XKRX | 1 | 8180029 | HLA-DOB2 | 2 |
| 8175844 | IDH3G | 1 | 8180034 | TAP2 | 2 |
| 8179298 | CSNK2B | 1 | 8180049 | PSMB8 | 2 |
| 8180343 | RAC1 | 1 | 8180061 | TAP1 | 2 |
| 7897728 | FBXO6 | 2 | 8180078 | HLA-DMB | 2 |
| 7898799 | C1QC | 2 | 8180086 | HLA-DMA | 2 |
| 7898805 | C1QB | 2 | 8180093 | HLA-DOA | 2 |
| 7906355 | CD1E | 2 | 8180100 | HLA-DPA1 | 2 |
| 7917561 | GBP4 | 2 | 7894264 | NA | 3 |
| 7919971 | RFX5 | 2 | 7895149 | NA | 3 |
| 7931951 | SFMBT2 | 2 | 7896038 | NA | 3 |
| 7934215 | SPOCK2 | 2 | 7896908 | PUSL1 | 3 |
| 7938035 | TRIM22 | 2 | 7897263 | RNF207 | 3 |
| 7942569 | SLGO2B1 | 2 | 7898115 | TMEM51 | 3 |
| 7945962 | TRIM21 | 2 | 7898161 | EFHD2 | 3 |
| 7948274 | UBE2L6 | 2 | 7903827 | STRIP1 | 3 |
| 7949340 | BATF2 | 2 | 7904050 | MOV10 | 3 |
| 7953428 | CD4 | 2 | 7905881 | ADAM15 | 3 |
| 7953993 | BCL2L14 | 2 | 7908694 | NAV1 | 3 |
| 7960947 | A2M | 2 | 7908793 | NA | 3 |
| 7964119 | STAT2 | 2 | 7909127 | MFSD4 | 3 |
| 7978123 | PSME2 | 2 | 7909188 | IKBKE | 3 |
| 7980958 | LGMN | 2 | 7912239 | GPR157 | 3 |
| 7981290 | WAR5 | 2 | 7912374 | SRM | 3 |
| 7993195 | NA | 2 | 7912496 | MTHFR | 3 |
| 7995926 | NLRC5 | 2 | 7912537 | NA | 3 |
| 8006214 | ADAP2 | 2 | 7912638 | TMEM51-AS1 | 3 |
| 8010426 | RNF213 | 2 | 7913256 | DDOST | 3 |

TABLE 12-continued

| | | 535 cancer-associated differentially expressed genes in nasal epithelium | | | |
|---|---|---|---|---|---|
| Probeset | Gene Symbol | Gene Cluster | Probeset | Gene Symbol | Gene Cluster |
| 8010454 | RNF213 | 2 | 7915184 | NA | 3 |
| 8026971 | IFI30 | 2 | 7915543 | SLC6A9 | 3 |
| 8029536 | APOC1 | 2 | 7915659 | HECTD3 | 3 |
| 8034304 | ACP5 | 2 | 7918394 | EPS8L3 | 3 |
| 8057744 | STAT1 | 2 | 7919872 | FAM63A | 3 |
| 8066214 | TGM2 | 2 | 7920271 | S100A4 | 3 |
| 8066905 | ZNFX1 | 2 | 7920291 | NA | 3 |
| 8072710 | APOL6 | 2 | 7920642 | MUC1 | 3 |
| 7923662 | PIK3C2B | 3 | 8005661 | NA | 3 |
| 7924150 | TMEM206 | 3 | 8006984 | PSMD3 | 3 |
| 7924823 | JMUD4 | 3 | 8007188 | CNP | 3 |
| 7925876 | NA | 3 | 8007505 | DHX8 | 3 |
| 7929882 | SEMA4G | 3 | 8007620 | GRN | 3 |
| 7930537 | TCF7L2 | 3 | 8008664 | AKAP1 | 3 |
| 7931899 | NA | 3 | 8009666 | RAB37 | 3 |
| 7934196 | PSAP | 3 | 8009693 | TMEM104 | 3 |
| 7934477 | CAMK2G | 3 | 8010354 | GAA | 3 |
| 7935058 | MYOF | 3 | 8011293 | CLUH | 3 |
| 7935188 | NA | 3 | 8011516 | ATP2A3 | 3 |
| 7937518 | TSPAN4 | 3 | 8011671 | GGT6 | 3 |
| 7937713 | SYT8 | 3 | 8011713 | CXCL16 | 3 |
| 7938519 | MICALCL | 3 | 8012126 | CLDN7 | 3 |
| 7939546 | CD82 | 3 | 8014768 | NA | 3 |
| 7939665 | MDK | 3 | 8017867 | FAM20A | 3 |
| 7939767 | MADD | 3 | 8018324 | GGA3 | 3 |
| 7940160 | DTX4 | 3 | 8019211 | NPLOC4 | 3 |
| 7940530 | MYRF | 3 | 8019622 | TMEM106A | 3 |
| 7940798 | MARK2 | 3 | 8021301 | RAB27B | 3 |
| 7941621 | DPP3 | 3 | 8023043 | PSTPIP2 | 3 |
| 7942697 | NA | 3 | 8024687 | TJP3 | 3 |
| 7944164 | TMPRSS4 | 3 | 8028524 | ACTN4 | 3 |
| 7945204 | ST14 | 3 | 8029086 | CEACAM5 | 3 |
| 7945666 | CTSD | 3 | 8029098 | CEACAM6 | 3 |
| 7946781 | LEKHA7 | 3 | 8029560 | CLPTM1 | 3 |
| 7947815 | ACP2 | 3 | 8032789 | STAP2 | 3 |
| 7948444 | TCN1 | 3 | 8034420 | MAN2B1 | 3 |
| 7948588 | SYT7 | 3 | 8034589 | FAR5A | 3 |
| 7949765 | PPP1CA | 3 | 8037205 | NA | 3 |
| 7951309 | MMP13 | 3 | 8037222 | CEACAM8 | 3 |
| 7951896 | PCSK7 | 3 | 8037794 | PRKD2 | 3 |
| 7952132 | SLC37A4 | 3 | 8038261 | GYS1 | 3 |
| 7952290 | TRIM29 | 3 | 8039389 | PTPRH | 3 |
| 7953341 | TAPBPL | 3 | 8040365 | TRIB2 | 3 |
| 7953483 | USP5 | 3 | 8040698 | SLC35F6 | 3 |
| 7955613 | KRT7 | 3 | 8040753 | TMEM214 | 3 |
| 7958989 | PLBD2 | 3 | 8043657 | CNNM4 | 3 |
| 7962842 | NA | 3 | 8045539 | NA | 3 |
| 7964203 | BAZ2A | 3 | 8047738 | NA | 3 |
| 7969414 | KLF5 | 3 | 8048717 | SGPP2 | 3 |
| 7976000 | ADCK1 | 3 | 8050160 | MBOAT2 | 3 |
| 7976567 | BDKRB1 | 3 | 8051298 | GALNT14 | 3 |
| 7977046 | TNFAIP2 | 3 | 8051322 | XDH | 3 |
| 7977249 | INF2 | 3 | 8053214 | AUP1 | 3 |
| 7977511 | TEP1 | 3 | 8053406 | RETSAT | 3 |
| 7978260 | DHRS1 | 3 | 8054054 | NA | 3 |
| 7983405 | DUOXA2 | 3 | 8058390 | RAPH1 | 3 |
| 7983478 | C15orf48 | 3 | 8058973 | ZNF142 | 3 |
| 7983512 | SQRDL | 3 | 8059222 | DNPEP | 3 |
| 7984779 | PML | 3 | 8060353 | RBCK1 | 3 |
| 7985240 | TMED3 | 3 | 8062041 | ACSS2 | 3 |
| 7985620 | ALPK3 | 3 | 8062251 | NA | 3 |
| 7987230 | LPCAT4 | 3 | 8062927 | PI3 | 3 |
| 7988350 | DUOX2 | 3 | 8063000 | NA | 3 |
| 7990417 | SCAMP2 | 3 | 8063078 | CTSA | 3 |
| 7994737 | NA | 3 | 8063351 | SLC9A8 | 3 |
| 7997152 | CHST4 | 3 | 8063893 | ADRM1 | 3 |
| 7997158 | NA | 3 | 8064613 | SLC4A11 | 3 |
| 7997401 | BCO1 | 3 | 8065612 | NOL4L | 3 |
| 7998222 | MRPL28 | 3 | 8065920 | NA | 3 |
| 7999909 | GPRC5B | 3 | 8065948 | FER1L4 | 3 |
| 8000375 | ARHGAP17 | 3 | 8066513 | SDC4 | 3 |
| 8000543 | NA | 3 | 8068254 | IL10RB | 3 |
| 8000811 | MAPK3 | 3 | 8068810 | SLC37A1 | 3 |
| 8001030 | PYCARD | 3 | 8069399 | NA | 3 |
| 8001552 | CIAPIN1 | 3 | 8070538 | C2CD2 | 3 |
| 8002133 | PSMB10 | 3 | 8072108 | ASPHD2 | 3 |

TABLE 12-continued 535 cancer-associated differentially expressed genes in nasal epithelium

| Probeset | Gene Symbol | Gene Cluster | Probeset | Gene Symbol | Gene Cluster |
|---|---|---|---|---|---|
| 8002421 | VAC14 | 3 | 8072926 | H1F0 | 3 |
| 8005475 | TRIM16L | 3 | 8073605 | BIK | 3 |
| 8076569 | TTLL12 | 3 | 8179638 | TRIM26 | 3 |
| 8076998 | PLXNB2 | 3 | 8180166 | TAPBP | 3 |
| 8077082 | LMF2 | 3 | 7892796 | NA | 4 |
| 8080100 | RAD54L2 | 3 | 7893130 | NA | 4 |
| 8082797 | TF | 3 | 7894970 | NA | 4 |
| 8084717 | ST6GAL1 | 3 | 7895574 | NA | 4 |
| 8084895 | MUC20 | 3 | 7896160 | NA | 4 |
| 8084929 | SLCS1A | 3 | 7899502 | RNU11 | 4 |
| 8085300 | SEC13 | 3 | 7902043 | DNAJC6 | 4 |
| 8087485 | NA | 3 | 7916506 | C1orf168 | 4 |
| 8088425 | FAM3D | 3 | 7930612 | NA | 4 |
| 8090823 | SLCO2A1 | 3 | 7932498 | SKIDA1 | 4 |
| 8092978 | MUC4 | 3 | 7944765 | NA | 4 |
| 8093230 | NA | 3 | 7953383 | SCARNA10 | 4 |
| 8096070 | BMP3 | 3 | 7961710 | ABCC9 | 4 |
| 8103025 | ZNF827 | 3 | 7964631 | FAM19A2 | 4 |
| 8104079 | FAT1 | 3 | 7971165 | NA | 4 |
| 8106170 | TMEM171 | 3 | 7978407 | PRKD1 | 4 |
| 8114050 | 8-Sep | 3 | 7985317 | CEMIP | 4 |
| 8115623 | ATP10B | 3 | 7999291 | C16orf89 | 4 |
| 8118833 | UHRF1BP1 | 3 | 8006504 | FNDC8 | 4 |
| 8119926 | TMEM63B | 3 | 8009380 | SNORA38B | 4 |
| 8122843 | ESR1 | 3 | 8013521 | NA | 4 |
| 8123606 | SERPINB9P1 | 3 | 8013523 | NA | 4 |
| 8125766 | BAK1 | 3 | 8043782 | CNGA3 | 4 |
| 8129677 | SGK1 | 3 | 8045287 | NA | 4 |
| 8133721 | HSPB1 | 3 | 8049530 | LRRAP1 | 4 |
| 8136849 | GSTK1 | 3 | 8076223 | NA | 4 |
| 8136863 | TMEM139 | 3 | 8089145 | ABI3BP | 4 |
| 8137798 | PSMG3 | 3 | 8098604 | ANKRD37 | 4 |
| 8139859 | GUSB | 3 | 8101762 | SNCA | 4 |
| 8143575 | EPHA1 | 3 | 8104141 | PLEKHG4B | 4 |
| 8144880 | SH2D4A | 3 | 8107204 | NA | 4 |
| 8145027 | FAM160B2 | 3 | 8108180 | NA | 4 |
| 8145669 | NA | 3 | 8127658 | NA | 4 |
| 8146921 | RDH10 | 3 | 8132248 | NA | 4 |
| 8148548 | PSCA | 3 | 8147990 | NA | 4 |
| 8148572 | LY6E | 3 | 8156358 | NA | 4 |
| 8149330 | CTSB | 3 | 8165694 | NA | 4 |
| 8150036 | KIF13B | 3 | 8165696 | NA | 4 |
| 8150112 | GSR | 3 | 8165698 | NA | 4 |
| 8152828 | GSDMC | 3 | 8165700 | NA | 4 |
| 8153334 | PSCA | 3 | 8165707 | NA | 4 |
| 8153342 | LYPD2 | 3 | 8168868 | ARMCX1 | 4 |
| 8155707 | NA | 3 | 8175531 | CDR1 | 4 |
| 8156058 | NA | 3 | | | |
| 8157362 | ZNF618 | 3 | | | |
| 8157381 | ZNF618 | 3 | | | |
| 8158167 | LCN2 | 3 | | | |
| 8158242 | URM1 | 3 | | | |
| 8158671 | NA | 3 | | | |
| 8158684 | NA | 3 | | | |
| 8158961 | GTF3C5 | 3 | | | |
| 8160670 | AQP3 | 3 | | | |
| 8161174 | GNE | 3 | | | |
| 8162502 | FBP1 | 3 | | | |
| 8162729 | TRIM14 | 3 | | | |
| 8162744 | CORO2A | 3 | | | |
| 8163505 | HDHD3 | 3 | | | |
| 8164535 | CRAT | 3 | | | |
| 8164580 | PIGES | 3 | | | |
| 8172280 | SLC9A7 | 3 | | | |
| 8175924 | NAA10 | 3 | | | |
| 8178115 | CFB | 3 | | | |
| 8178561 | ABHD16A | 3 | | | |
| 8179028 | LOC554223 | 3 | | | |
| 8179112 | ABCF1 | 3 | | | |
| 8179331 | C2 | 3 | | | |
| 8179351 | CFB | 3 | | | |
| 8179364 | SKIV2L | 3 | | | |

TABLE 13

Genes and parameters of the genomic lung cancer weighted voting classifier

| Probeset | Gene Symbol | Weight | Probeset | Gene Symbol | Weight |
|---|---|---|---|---|---|
| 8091385 | CP | −0.076842875 | 8117476 | BTN3A3 | −0.097876771 |
| 8115147 | CD74 | −0.06681241 | 8180078 | HLA-DMB | −0.112823827 |
| 8034420 | MAN2B1 | −0.050873844 | 7925876 | NA | −0.042561684 |
| 8075720 | APOL2 | −0.08530029 | 8092978 | MUC4 | −0.048934863 |
| 7940775 | RARRES3 | −0.066344128 | 7940160 | DTX4 | −0.040517314 |
| 8125463 | NA | −0.10036146 | 8076998 | PLXNB2 | −0.025531407 |
| 7912638 | TMEM51-AS1 | −0.073178603 | 8179041 | NA | −0.029847889 |
| 7978123 | PSME2 | −0.058857757 | 8145317 | ADAMDEC1 | −0.152455958 |
| 7937217 | ECHS1 | −0.029153753 | 8180049 | PSMB8 | −0.073333856 |
| 8002133 | PSMB10 | −0.059579001 | 7993195 | NA | −0.056308918 |
| 8084895 | MUC20 | −0.053920489 | 7929882 | SEMA4G | −0.059567336 |
| 8180166 | TAPBP | −0.043521631 | 8179049 | HLA-J | −0.029200433 |
| 8179331 | C2 | −0.102616464 | 7947815 | ACP2 | −0.042164826 |
| 8146092 | IDO1 | −0.256702735 | 8096070 | BMP3 | −0.081582712 |
| 7898115 | TMEM51 | −0.047151531 | 8063000 | NA | −0.032633301 |

TABLE 14

Genes and parameters of the genomic smoking status logistic regression model

| Probeset | Gene Symbol | Coefficient |
|---|---|---|
| Intercept | NA | −24.1410 |
| 8051583 | CYP1B1 | 0.2521 |
| 7990391 | CYP1A1 | 0.0544 |
| 7942693 | B3GNT6 | 2.5181 |
| 8080578 | CACNA2D3 | 1.7191 |
| 8033257 | C3 | −0.4727 |

TABLE 15

Genes and parameters of the genomic time since quit logistic regression model

| Probeset | Gene Symbol | Coefficient |
|---|---|---|
| Intercept | NA | −1.8161 |
| 7990391 | GRAMD2 | 0.5726 |
| 8051583 | CYP1B1 | −0.4519 |

TABLE 16

Genes and parameters of the clinical risk-factor lung cancer classifier

| Variable | Coefficient |
|---|---|
| Intercept | −5.14689 |
| Genomic Smoking Classifier Score | 1.82244 |
| Genomic Time Since Quit Classifier Score | 2.31235 |
| Age | 0.04947 |
| Mass Size (Infiltrate vs <3 cm) | 1.27246 |
| Mass Size (Infiltrate vs >3 cm) | 2.59898 |

TABLE 17

Genes and parameters of the clinicogenomic lung cancer classifier

| Variable | Coefficient |
|---|---|
| Intercept | −4.1504024 |
| Genomic Smoking Classifier Score | 0.7534516 |
| Genomic Time Since Quit Classifier Score | 0.3276714 |
| Genomic Cancer Classifier Score | 0.6629011 |
| Age | 0.0452670 |

TABLE 17-continued

Genes and parameters of the clinicogenomic lung cancer classifier

| Variable | Coefficient |
|---|---|
| Mass Size (Infiltrate vs <3 cm) | 1.3423457 |
| Mass Size (Infiltrate vs >3 cm) | 2.6932782 |

TABLE 18

Performance metrics of clinical risk-factor and clinicogenomic classifiers in the independent AEGIS-2 validation set

| | Clinical Risk-Factor Mode* | Clinico-genomic | p-value |
|---|---|---|---|
| AUC | 0.76 | 0.80 | 0.0495 |
| Sens | 0.85 | 0.94 | 0.0412 |
| Spec | 0.42 | 0.44 | 1.0000 |
| NPV | 0.73 | 0.87 | — |
| PPV | 0.60 | 0.63 | — |
| ACC | 0.64 | 0.69 | — |

TABLE 19

Comparison of clinical risk-factor model and clinicogenomic classifiers in lesion size and location patient subgroups

| | | | Sensitivity (%) | | |
|---|---|---|---|---|---|
| Group | All Patients | Patients with Cancer | Clinical Risk-Factor Model | Clinico-genomic Model | p-value |
| All patients | 130 | 66 | 85 | 94 | 0.0412 |
| Lesion Size | | | | | |
| <3 cm | 54 | 16 | 63 | 88 | 0.1336 |
| >= 3 cm | 59 | 46 | 100 | 100 | 1.0000 |
| Infiltrates | 17 | 4 | 0 | 50 | n/a |
| Lesion Location | | | | | |
| Central | 55 | 28 | 89 | 96 | 0.4795 |
| Peripheral | 31 | 6 | 67 | 83 | 1.0000 |
| Both | 44 | 32 | 84 | 94 | 0.2482 |

TABLE 20

| | Comparison of clinical risk-factor and clinicogenomic classifiers in disease stage and disease cell type subgroups | | | |
|---|---|---|---|---|
| | | Sensitivity (%) | | |
| Group | Patients with Cancer | Clinical Risk-Factor Model | Clinicogenomic Model | p-value |
| Stage | | | | |
| 1a, 1b | 6 | 50 | 67 | 1.0000 |
| 2a, 2b | 4 | 100 | 100 | 1.0000 |
| 3a, 3b | 17 | 94 | 94 | 1.0000 |
| 4 | 22 | 86 | 95 | 0.4795 |
| Extensive | 7 | 71 | 100 | n/a |
| Other | 10 | 90 | 100 | n/a |
| Cell Type | | | | |
| Adenocarinoma | 26 | 85 | 92 | 0.4795 |
| Squamous | 17 | 82 | 94 | 0.4795 |
| Small Cell | 7 | 71 | 100 | n/a |
| Unknown or NA | 16 | 94 | 94 | 1.0000 |

TABLE 21

| Probeset | Gene Symbol | Direction in Cancer |
|---|---|---|
| 7892618 | NA | down |
| 7892678 | NA | down |
| 7892766 | NA | down |
| 7892947 | NA | down |
| 7893061* | NA | down |
| 7893173 | NA | down |
| 7893248 | NA | down |
| 7893296* | NA | down |
| 7893333 | NA | down |
| 7893647 | NA | down |
| 7893862 | NA | down |
| 7894331 | NA | down |
| 7894501 | NA | down |
| 7894737 | NA | down |
| 7894926 | NA | down |
| 7895180 | NA | down |
| 7895602* | NA | down |
| 7895618 | NA | down |
| 7896201 | NA | down |
| 7896651 | NA | down |
| 7901110* | AKR1A1 | down |
| 7904830 | RNF115 | down |
| 7905938 | SLC50A1 | down |
| 7906079* | RAB25 | down |
| 7908147 | TSEN15 | down |
| 7910416 | URB2 | down |
| 7912412 | MTOR | down |
| 7914563 | YARS | down |
| 7914834* | PSMB2 | down |
| 7915504 | ELOVL1 | down |
| 7915578* | TMEM53 | down |
| 7917359 | ZNHIT6 | down |
| 7920971* | C1orf85 | down |
| 7923483* | RABIF | down |
| 7923929* | PIGR | down |
| 7928630 | EIF5AL1 | down |
| 7930031 | GBF1 | down |
| 7930498* | ACSL5 | down |
| 7930533 | LOC143188 | Down |
| 7930577 | CASP7 | down |
| 7931778 | PITRM1 | down |
| 7933760* | CCDC6 | down |
| 7934133 | PPA1 | down |
| 7934653 | POLR3A | down |
| 7934753 | NA | down |
| 7936284* | XPNPEP1 | down |
| 7937217* | ECHS1 | down |
| 7938834 | NAV2 | down |
| 7940775 | RARRES3 | down |

TABLE 21-continued

| Probeset | Gene Symbol | Direction in Cancer |
|---|---|---|
| 7944803* | VWA5A | down |
| 7950248* | FCHSD2 | down |
| 7950906* | CTSC | down |
| 7951565* | ARHGAP20 | down |
| 7952557 | SRPR | down |
| 7953395 | COPS7A | down |
| 7953981* | ETV6 | down |
| 7958828 | TRAFD1 | down |
| 7959153 | COX6A1 | down |
| 7962869 | DDX23 | down |
| 7963187 | LIMA1 | down |
| 7967175 | KDM2B | down |
| 7969794 | LOC100132099 | down |
| 7973314* | OXA1L | down |
| 7973564* | PSME1 | down |
| 7979743 | RDH11 | down |
| 7979757* | ZFYVE26 | down |
| 7980146* | NPC2 | down |
| 7981824 | NA | down |
| 7985959* | GDPGP1 | down |
| 7987536* | RMDN3 | down |
| 7988124 | PPIP5K1 | down |
| 7988132* | STRC | down |
| 7989619 | PPIB | down |
| 7991323* | PEX11A | down |
| 7993223* | CLEC16A | down |
| 7996725 | DUS2 | down |
| 7996908 | SNTB2 | down |
| 7999791 | NA | down |
| 8002919 | KARS | Down |
| 8005994 | ERAL1 | down |
| 8006392 | PSMD11 | down |
| 8006531 | SLFN5 | down |
| 8006812* | PSMB3 | down |
| 8007302* | TUBG1 | down |
| 8007312* | TUBG2 | down |
| 8007715 | NMT1 | down |
| 8008139* | UBE2Z | down |
| 8009164* | DCAF7 | down |
| 8010924 | VPS53 | down |
| 8011599 | ANKFY1 | down |
| 8012856* | ELAC2 | down |
| 8013588 | POLDIP2 | down |
| 8013641* | PIGS | down |
| 8014115 | MYO1D | down |
| 8014903* | NA | down |
| 8015545 | RAB5C | down |
| 8016099* | EFTUD2 | down |
| 8021727 | CNDP2 | down |
| 8026106 | CALR | down |
| 8027876 | TMEM147 | down |
| 8028705 | TIMM50 | down |
| 8028756 | PSMC4 | down |
| 8031827 | ZNF587 | down |
| 8033912 | DNMT1 | down |
| 8036010* | PEPD | down |
| 8042576* | NAGK | down |
| 8043100 | TMSB10 | down |
| 8043197 | VAMP8 | down |
| 8043937* | CNOT11 | down |
| 8047403* | CASP10 | down |
| 8048926 | SP140L | down |
| 8058914 | AAMP | down |
| 8059350 | AP1S3 | down |
| 8059361* | WDFY1 | down |
| 8062349 | RPN2 | down |
| 8062981 | PIGT | down |
| 8063211 | NCOA3 | down |
| 8063369* | RNF114 | down |
| 8064522* | IDH3B | Down |
| 8065832* | TRPC4AP | down |
| 8066939* | B4GALT5 | down |
| 8075585 | RTCB | down |
| 8080938 | MITF | down |
| 8086028 | GLB1 | down |
| 8088247 | ARHGEF3 | down |
| 8088634 | NA | down |
| 8089544 | CCDC80 | down |

TABLE 21-continued

| Probeset | Gene Symbol | Direction in Cancer |
|---|---|---|
| 8089568 | CD200R1 | down |
| 8091385 | CP | down |
| 8091991 | NA | down |
| 8092169* | TNFSF10 | down |
| 8092230 | ZMAT3 | down |
| 8092541 | LIPH | down |
| 8093398* | PCGF3 | down |
| 8093685 | HTT | down |
| 8095139* | SRD5A3 | down |
| 8098547 | NA | down |
| 8102311* | CASP6 | down |
| 8103911 | IRF2 | down |
| 8105077 | CARD6 | down |
| 8108558* | SLC35A4 | down |
| 8108593* | WDR55 | down |
| 8114145 | VDAC1 | down |
| 8116096 | DDX41 | down |
| 8117243* | LRRC16A | down |
| 8117321* | TRIM38 | down |
| 8122013 | L3MBTL3 | down |
| 8122803* | NA | down |
| 8123062 | TMEM181 | down |
| 8123800* | NA | down |
| 8123951* | ADTRP | down |
| 8126588* | XPO5 | down |
| 8126729 | NA | down |
| 8129254* | MAN1A1 | down |
| 8131631* | HDAC9 | down |
| 8133690* | MDH2 | down |
| 8134091* | CLDN12 | down |
| 8135422* | BCAP29 | down |
| 8136095 | AHCYL2 | Down |
| 8136580 | RAB19 | down |
| 8139392 | DDX56 | down |
| 8147112* | NA | down |
| 8148059 | DEPTOR | down |
| 8153474 | TSTA3 | down |
| 8154733* | ACO1 | down |
| 8156770 | GALNT12 | down |
| 8159249 | MRPS2 | down |
| 8160914 | VCP | down |
| 8163452 | FKBP15 | down |
| 8165866 | STS | down |
| 8168762 | CSTF2 | down |
| 8169249 | MID2 | down |
| 8170882 | ATP6AP1 | down |
| 8173979* | NOX1 | down |
| 8173999* | XKRX | down |
| 8175844 | IDH3G | down |
| 8179298* | CSNK2B | down |
| 8180343 | RAC1 | down |
| 7897728 | FBXO6 | down |
| 7898799* | C1QC | down |
| 7898805* | C1QB | down |
| 7906355* | CD1E | down |
| 7917561 | GBP4 | down |
| 7919971* | RFX5 | down |
| 7931951 | SFMBT2 | down |
| 7934215* | SPOCK2 | down |
| 7938035* | TRIM22 | down |
| 7942569* | SLCO2B1 | down |
| 7945962* | TRIM21 | down |
| 7948274* | UBE2L6 | down |
| 7949340 | BATF2 | down |
| 7953428 | CD4 | down |
| 7953993 | BCL2L14 | down |
| 7960947 | A2M | down |
| 7964119 | STAT2 | down |
| 7978123* | PSME2 | down |
| 7980958* | LGMN | down |
| 7981290 | WARS | down |
| 7993195* | NA | Down |
| 7995926* | NLRC5 | down |
| 8006214* | ADAP2 | down |
| 8010426 | RNF213 | down |
| 8010454 | RNF213 | down |
| 8026971* | IFI30 | down |
| 8029536* | APOC1 | down |

TABLE 21-continued

| Probeset | Gene Symbol | Direction in Cancer |
|---|---|---|
| 8034304* | ACP5 | down |
| 8057744 | STAT1 | down |
| 8066214 | TGM2 | down |
| 8066905 | ZNFX1 | down |
| 8072710 | APOL6 | down |
| 8072735 | APOL1 | down |
| 8075720 | APOL2 | down |
| 8082075 | DTX3L | down |
| 8086125* | TRANK1 | down |
| 8090018 | PARP9 | down |
| 8115147* | CD74 | down |
| 8117435* | BTN3A2 | down |
| 8117458 | BTN3A1 | down |
| 8117476* | BTN3A3 | down |
| 8117760* | HLA-F | down |
| 8117777* | NA | down |
| 8118556* | NA | down |
| 8118594* | HLA-DPB1 | down |
| 8125463* | NA | down |
| 8125483 | TAP2 | down |
| 8125993 | ETV7 | down |
| 8140971 | SAMD9L | down |
| 8143327 | PARP12 | down |
| 8145317* | ADAMDEC1 | down |
| 8146092* | IDO1 | down |
| 8161964 | FRMD3 | down |
| 8177732* | HLA-A | down |
| 8178193* | HLA-DRA | down |
| 8178205* | HLA-DQA2 | down |
| 8179019* | HLA-F | down |
| 8179041* | NA | down |
| 8179049* | HLA-J | down |
| 8179481* | HLA-DRA | down |
| 8179489* | NA | Down |
| 8179495* | PSMB9 | down |
| 8179519* | HLA-DPB1 | down |
| 8179731* | NA | down |
| 8180003* | NA | down |
| 8180022* | NA | down |
| 8180029* | HLA-DQB2 | down |
| 8180034* | TAP2 | down |
| 8180049* | PSMB8 | down |
| 8180061* | TAP1 | down |
| 8180078* | HLA-DMB | down |
| 8180086* | HLA-DMA | down |
| 8180093* | HLA-DOA | down |
| 8180100* | HLA-DPA1 | down |
| 7894264 | NA | down |
| 7895149 | NA | down |
| 7896038 | NA | down |
| 7896908 | PUSL1 | down |
| 7897263* | RNF207 | down |
| 7898115* | TMEM51 | down |
| 7898161* | EFHD2 | down |
| 7903827 | STRIP1 | down |
| 7904050* | MOV10 | down |
| 7905881* | ADAM15 | down |
| 7908694 | NAV1 | down |
| 7908793 | NA | down |
| 7909127 | MFSD4 | down |
| 7909188* | IKBKE | down |
| 7912239 | GPR157 | down |
| 7912374 | SRM | down |
| 7912496 | MTHFR | down |
| 7912537 | NA | down |
| 7912638* | TMEM51-AS1 | down |
| 7913256 | DDOST | down |
| 7915184* | NA | down |
| 7915543* | SLC6A9 | down |
| 7915659 | HECTD3 | down |
| 7918394* | EPS8L3 | down |
| 7919872* | FAM63A | down |
| 7920271* | S100A4 | down |
| 7920291 | NA | Down |
| 7920642 | MUC1 | down |
| 7923662* | PIK3C2B | down |
| 7924150* | TMEM206 | down |
| 7924823 | JMJD4 | down |

TABLE 21-continued

| Probeset | Gene Symbol | Direction in Cancer |
|---|---|---|
| 7925876 | NA | down |
| 7929882 | SEMA4G | down |
| 7930537* | TCF7L2 | down |
| 7931899 | NA | down |
| 7934196* | PSAP | down |
| 7934477* | CAMK2G | down |
| 7935058 | MYOF | down |
| 7935188 | NA | down |
| 7937518 | TSPAN4 | down |
| 7937713 | SYT8 | down |
| 7938519* | MICALCL | down |
| 7939546* | CD82 | down |
| 7939665* | MDK | down |
| 7939767* | MADD | down |
| 7940160 | DTX4 | down |
| 7940530 | MYRF | down |
| 7940798 | MARK2 | down |
| 7941621 | DPP3 | down |
| 7942697 | NA | down |
| 7944164 | TMPRSS4 | down |
| 7945204 | ST14 | down |
| 7945666 | CTSD | down |
| 7946781* | PLEKHA7 | down |
| 7947815* | ACP2 | down |
| 7948444 | TCN1 | down |
| 7948588 | SYT7 | down |
| 7949765 | PPP1CA | down |
| 7951309 | MMP13 | down |
| 7951896 | PCSK7 | down |
| 7952132* | SLC37A4 | down |
| 7952290 | TRIM29 | down |
| 7953341* | TAPBPL | down |
| 7953483 | USP5 | down |
| 7955613* | KRT7 | down |
| 7958989* | PLBD2 | down |
| 7962842 | NA | down |
| 7964203* | BAZ2A | down |
| 7969414 | KLF5 | down |
| 7976000 | ADCK1 | down |
| 7976567 | BDKRB1 | down |
| 7977046* | TNFAIP2 | down |
| 7977249 | INF2 | down |
| 7977511 | TEP1 | down |
| 7978260 | DHRS1 | down |
| 7983405* | DUOXA2 | down |
| 7983478* | C15orf48 | down |
| 7983512* | SQRDL | down |
| 7984779 | PML | down |
| 7985240 | TMED3 | down |
| 7985620* | ALPK3 | down |
| 7987230* | LPCAT4 | down |
| 7988350* | DUOX2 | down |
| 7990417 | SCAMP2 | down |
| 7994737* | NA | down |
| 7997152* | CHST4 | down |
| 7997158 | NA | down |
| 7997401 | BCO1 | down |
| 7998222* | MRPL28 | down |
| 7999909* | GPRC5B | down |
| 8000375* | ARHGAP17 | down |
| 8000543* | NA | down |
| 8000811* | MAPK3 | down |
| 8001030* | PYCARD | down |
| 8001552* | CIAPIN1 | down |
| 8002133* | PSMB10 | down |
| 8002421* | VAC14 | down |
| 8005475 | TRIM16L | down |
| 8005661* | NA | down |
| 8006984 | PSMD3 | down |
| 8007188 | CNP | down |
| 8007505* | DHX8 | down |
| 8007620* | GRN | down |
| 8008664 | AKAP1 | down |
| 8009666 | RAB37 | down |
| 8009693* | TMEM104 | down |
| 8010354 | GAA | Down |
| 8011293 | CLUH | down |
| 8011516 | ATP2A3 | down |
| 8011671* | GGT6 | down |
| 8011713* | CXCL16 | down |
| 8012126 | CLDN7 | down |
| 8014768 | NA | down |
| 8017867* | FAM20A | down |
| 8018324* | GGA3 | down |
| 8019211 | NPLOC4 | down |
| 8019622 | TMEM106A | down |
| 8021301 | RAB27B | down |
| 8023043* | PSTPIP2 | down |
| 8024687* | TJP3 | down |
| 8028524 | ACTN4 | down |
| 8029086 | CEACAM5 | down |
| 8029098 | CEACAM6 | down |
| 8029560 | CLPTM1 | down |
| 8032789* | STAP2 | down |
| 8034420* | MAN2B1 | down |
| 8034589* | FARSA | down |
| 8037205 | NA | down |
| 8037222 | CEACAM8 | down |
| 8037794* | PRKD2 | down |
| 8038261* | GYS1 | down |
| 8039389 | PTPRH | down |
| 8040365* | TRIB2 | down |
| 8040698 | SLC35F6 | down |
| 8040753 | TMEM214 | down |
| 8043657* | CNNM4 | down |
| 8045539* | NA | down |
| 8047738 | NA | down |
| 8048717 | SGPP2 | down |
| 8050160 | MBOAT2 | down |
| 8051298* | GALNT14 | down |
| 8051322 | XDH | down |
| 8053214 | AUP1 | down |
| 8053406 | RETSAT | down |
| 8054054* | NA | down |
| 8058390* | RAPH1 | down |
| 8058973 | ZNF142 | Down |
| 8059222 | DNPEP | down |
| 8060353* | RBCK1 | down |
| 8062041* | ACSS2 | down |
| 8062251 | NA | down |
| 8062927* | PI3 | down |
| 8063000* | NA | down |
| 8063078* | CTSA | down |
| 8063351* | SLC9A8 | down |
| 8063893 | ADRM1 | down |
| 8064613 | SLC4A11 | down |
| 8065612* | NOL4L | down |
| 8065920* | NA | down |
| 8065948* | FER1L4 | down |
| 8066513 | SDC4 | down |
| 8068254* | IL10RB | down |
| 8068810 | SLC37A1 | down |
| 8069399* | NA | down |
| 8070538 | C2CD2 | down |
| 8072108 | ASPHD2 | down |
| 8072926* | H1F0 | down |
| 8073605* | BIK | down |
| 8076569 | TTLL12 | down |
| 8076998* | PLXNB2 | down |
| 8077082 | LMF2 | down |
| 8080100* | RAD54L2 | down |
| 8082797 | TF | down |
| 8084717* | ST6GAL1 | down |
| 8084895* | MUC20 | down |
| 8084929 | SLC51A | down |
| 8085300 | SEC13 | down |
| 8087485 | NA | down |
| 8088425* | FAM3D | down |
| 8090823 | SLCO2A1 | down |
| 8092978 | MUC4 | down |
| 8093230 | NA | down |
| 8096070 | BMP3 | down |
| 8103025* | ZNF827 | down |
| 8104079* | FAT1 | down |
| 8106170 | TMEM171 | down |
| 8114050* | 8-Sep | Down |

TABLE 21-continued

| Probeset | Gene Symbol | Direction in Cancer |
|---|---|---|
| 8115623* | ATP10B | down |
| 8118833* | UHRF1BP1 | down |
| 8119926 | TMEM63B | down |
| 8122843 | ESR1 | down |
| 8123606 | SERPINB9P1 | down |
| 8125766 | BAK1 | down |
| 8129677* | SGK1 | down |
| 8133721 | HSPB1 | down |
| 8136849* | GSTK1 | down |
| 8136863* | TMEM139 | down |
| 8137798 | PSMG3 | down |
| 8139859* | GUSB | down |
| 8143575 | EPHA1 | down |
| 8144880* | SH2D4A | down |
| 8145027 | FAM160B2 | down |
| 8145669* | NA | down |
| 8146921 | RDH10 | down |
| 8148548 | PSCA | down |
| 8148572* | LY6E | down |
| 8149330* | CTSB | down |
| 8150036 | KIF13B | down |
| 8150112 | GSR | down |
| 8152828 | GSDMC | down |
| 8153334 | PSCA | down |
| 8153342* | LYPD2 | down |
| 8155707 | NA | down |
| 8156058 | NA | down |
| 8157362* | ZNF618 | down |
| 8157381* | ZNF618 | down |
| 8158167* | LCN2 | down |
| 8158242* | URM1 | down |
| 8158671* | NA | down |
| 8158684* | NA | down |
| 8158961* | GTF3C5 | down |
| 8160670 | AQP3 | down |
| 8161174 | GNE | down |
| 8162502* | FBP1 | down |
| 8162729* | TRIM14 | down |
| 8162744* | CORO2A | down |
| 8163505* | HDHD3 | Down |
| 8164535* | CRAT | down |
| 8164580* | PTGES | down |
| 8172280* | SLC9A7 | down |
| 8175924* | NAA10 | down |
| 8178115* | CFB | down |
| 8178561 | ABHD16A | down |
| 8179028 | LOC554223 | down |
| 8179112* | ABCF1 | down |
| 8179331* | C2 | down |
| 8179351* | CFB | down |
| 8179364* | SKIV2L | down |
| 8179638 | TRIM26 | down |
| 8180166* | TAPBP | down |
| 7892796 | NA | up |
| 7893130 | NA | up |
| 7894970* | NA | up |
| 7895574 | NA | up |
| 7896160 | NA | up |
| 7899502* | RNU11 | up |
| 7902043* | DNAJC6 | up |
| 7916506* | C1orf168 | up |
| 7930612 | NA | up |
| 7932498* | SKIDA1 | up |
| 7944765 | NA | up |
| 7953383* | SCARNA10 | up |
| 7961710* | ABCC9 | up |
| 7964631 | FAM19A2 | up |
| 7971165 | NA | up |
| 7978407* | PRKD1 | up |
| 7985317* | CEMIP | up |
| 7999291 | C16orf89 | up |
| 8006504* | FNDC8 | up |
| 8009380 | SNORA38B | up |
| 8013521* | NA | up |
| 8013523 | NA | up |
| 8043782* | CNGA3 | up |
| 8045287* | NA | up |
| 8049530 | LRRFIP1 | up |

TABLE 21-continued

| Probeset | Gene Symbol | Direction in Cancer |
|---|---|---|
| 8076223* | NA | up |
| 8089145 | ABI3BP | Up |
| 8098604 | ANKRD37 | up |
| 8101762* | SNCA | up |
| 8104141* | PLEKHG4B | up |
| 8107204* | NA | up |
| 8108180* | NA | up |
| 8127658 | NA | up |
| 8132248 | NA | up |
| 8147990 | NA | up |
| 8156358 | NA | up |
| 8165694* | NA | up |
| 8165696 | NA | up |
| 8165698* | NA | up |
| 8165700 | NA | up |
| 8165707 | NA | up |
| 8168868 | ARMCX1 | up |
| 8175531* | CDR1 | up |

*indicates leading edge gene

TABLE 22

| Term | FDR |
|---|---|
| antigen processing and presentation of exogenous antigen (GO:0019884) | 2.64E−13 |
| antigen processing and presentation of exogenous peptide antigen (GO:0002478) | 2.64E−13 |
| antigen processing and presentation of peptide antigen (GO:0048002) | 8.84E−13 |
| antigen processing and presentation (GO:0019882) | 1.19E−11 |
| antigen processing and presentation of exogenous peptide antigen via MHC class I (GO:0042590) | 1.74E−08 |
| antigen processing and presentation of peptide antigen via MHC class I (GO:0002474) | 1.74E−08 |
| antigen processing and presentation of exogenous peptide antigen via MHC class I, TAP- dependent (GO:0002479) | 6.31E−08 |
| antigen processing and presentation of exogenous peptide antigen via MHC class II (GO:0019886) | 3.53E−05 |
| antigen processing and presentation of peptide antigen via MHC class II (GO:0002495) | 3.53E−05 |
| interferon-gamma-mediated signaling pathway (GO:0060333) | 3.53E−05 |
| antigen processing and presentation of peptide or polysaccharide antigen via MHC class II (GO:0002504) | 3.68E−05 |
| signal transduction involved in mitotic G1 DNA damage checkpoint (GO:0072431) | 3.68E−05 |
| intracellular signal transduction involved in G1 DNA damage checkpoint (GO:1902400) | 3.68E−05 |
| DNA damage response, signal transduction by p53 class mediator resulting in cell cycle arrest (GO:0006977) | 3.68E−05 |
| signal transduction involved in mitotic DNA integrity checkpoint (GO:1902403) | 3.68E−05 |
| signal transduction involved in mitotic cell cycle checkpoint (GO:0072413) | 3.68E−05 |
| signal transduction involved in mitotic DNA damage checkpoint (GO:1902402) | 3.68E−05 |
| signal transduction involved in DNA integrity checkpoint (GO:0072401) | 4.33E−05 |
| signal transduction involved in DNA damage checkpoint (GO:0072422) | 4.33E−05 |
| signal transduction involved in cell cycle checkpoint (GO:0072395) | 4.71E−05 |
| regulation of cellular amino acid metabolic process (GO:0006521) | 7.97E−05 |
| regulation of cellular amine metabolic process (GO:0033238) | 0.000147804 |
| positive regulation of cell cycle arrest (GO:0071158) | 0.000198665 |
| cellular response to interferon-gamma (GO:0071346) | 0.000264094 |
| DNA damage response, signal transduction by p53 class mediator (GO:0030330) | 0.000334076 |

TABLE 22-continued

| Term | FDR |
|---|---|
| response to interferon-gamma (GO:0034341) | 0.000334076 |
| negative regulation of Gl/S transition of mitotic cell cycle (GO:2000134) | 0.000681069 |
| negative regulation of cell cycle Gl/S phase transition (GO:1902807) | 0.000681069 |
| negative regulation of ubiquitin-protein ligase activity involved in mitotic cell cycle (GO:0051436) | 0.000741508 |
| regulation of antigen processing and presentation (GO:0002577) | 0.000976729 |
| proteasome-mediated ubiquitin-dependent protein catabolic process (GO:0043161) | 0.000976729 |
| regulation of cell cycle arrest (GO:0071156) | 0.001026492 |
| signal transduction in response to DNA damage (GO:0042770) | 0.001086018 |
| positive regulation of ubiquitin-protein ligase activity involved in mitotic cell cycle (GO:0051437) | 0.001116512 |
| proteasomal protein catabolic process (GO:0010498) | 0.001272502 |
| negative regulation of ligase activity (GO:0051352) | 0.001272502 |
| negative regulation of ubiquitin-protein transferase activity (GO:0051444) | 0.001272502 |
| regulation of G1/S transition of mitotic cell cycle (GO:2000045) | 0.001303525 |
| regulation of cell cycle Gl/S phase transition (GO:1902806) | 0.001475051 |
| signal transduction by p53 class mediator (GO:0072331) | 0.001548279 |
| regulation of ubiquitin-protein ligase activity involved in mitotic cell cycle (GO:0051439) | 0.00173373 |
| regulation of cellular ketone metabolic process (GO:0010565) | 0.001946114 |
| antigen processing and presentation of endogenous antigen (GO:0019883) | 0.002234329 |
| negative regulation of protein modification by small protein conjugation or removal (GO:1903321) | 0.002330593 |
| anaphase-promoting complex-dependent proteasomal ubiquitin-dependent protein catabolic process (GO:0031145) | 0.002330593 |
| post-translational protein modification (GO:0043687) | 0.003201008 |
| positive regulation of ubiquitin-protein transferase activity (GO:0051443) | 0.003523951 |
| proteolysis involved in cellular protein catabolic process (GO:0051603) | 0.003541561 |
| cytokine-mediated signaling pathway (GO:0019221) | 0.004071611 |
| protein catabolic process (GO:0030163) | 0.004704633 |
| positive regulation of ligase activity (GO:0051351) | 0.004980771 |
| regulation of antigen processing and presentation of peptide antigen (GO:0002583) | 0.005288359 |
| negative regulation of protein ubiquitination (GO:0031397) | 0.005404568 |
| modification-dependent protein catabolic process (GO:0019941) | 0.008295631 |
| protein polyubiquitination (GO:0000209) | 0.008295631 |
| modification-dependent macromolecule catabolic process (GO:0043632) | 0.009325558 |
| antigen processing and presentation of endogenous peptide antigen via MHC class I (GO:0019885) | 0.009413569 |
| regulation of ubiquitin-protein transferase activity (GO:0051438) | 0.010265072 |
| antigen processing and presentation of endogenous peptide antigen (GO:0002483) | 0.012182104 |
| negative regulation of protein modification process (GO:0031400) | 0.012670399 |
| regulation of ligase activity (GO:0051340) | 0.013876213 |
| ubiquitin-dependent protein catabolic process (GO:0006511) | 0.013915779 |
| regulation of apoptotic signaling pathway (GO:2001233) | 0.014172597 |
| positive regulation of antigen processing and presentation (GO:0002579) | 0.018895095 |
| negative regulation of transferase activity (GO:0051348) | 0.019241154 |
| regulation of T cell activation (GO:0050863) | 0.019692533 |
| O-glycan processing (GO:0016266) | 0.019692533 |
| T cell costimulation (GO:0031295) | 0.022242877 |
| protein N-linked glycosylation via asparagine (GO:0018279) | 0.022242877 |
| regulation of I-kappaB kinase/NF-kappaB signaling (GO:0043122) | 0.022924012 |

TABLE 22-continued

| Term | FDR |
|---|---|
| lymphocyte costimulation (GO:0031294) | 0.022924012 |
| peptidyl-asparagine modification (GO:0018196) | 0.022924012 |
| positive regulation of T cell activation (GO:0050870) | 0.023552255 |
| T cell receptor signaling pathway (GO:0050852) | 0.025340097 |
| negative regulation of viral release from host cell (GO:1902187) | 0.025340097 |
| tRNA metabolic process (GO:0006399) | 0.028902105 |
| protein N-linked glycosylation (GO:0006487) | 0.033855 |
| regulation of cytokine production (GO:0001817) | 0.03675597 |
| Gl/S transition of mitotic cell cycle (GO:0000082) | 0.037323339 |
| cell cycle Gl/S phase transition (GO:0044843) | 0.037323339 |
| regulation of type I interferon production (GO:0032479) | 0.04117111 |
| positive regulation of protein modification by small protein conjugation or removal (GO:1903322) | 0.048722949 |

TABLE 23

| Pathway | FDR |
|---|---|
| Interferon gamma signaling | 9.67E−08 |
| ER-Phagosome pathway | 1.34E−07 |
| Antigen processing-Cross presentation | 1.74E−06 |
| Interferon Signaling | 3.74E−06 |
| MHC class II antigen presentation | 3.74E−06 |
| Class I MHC mediated antigen processing & presentation | 7.67E−05 |
| Vpu mediated degradation of CD4 | 8.51E−05 |
| AUF1 (hnRNP D0) destabilizes mRNA | 0.00012195 |
| Hh ligand biogenesis disease | 0.00019564 |
| Hedgehog ligand biogenesis | 0.00019564 |
| Processing-defective Hh variants abrogate ligand secretion | 0.00019564 |
| Ubiquitin-dependent degradation of Cyclin D1 | 0.00019564 |
| Cross-presentation of soluble exogenous antigens (endosomes) | 0.00019564 |
| Autodegradation of the E3 ubiquitin ligase COP1 | 0.00019564 |
| Regulation of activated PAK-2p34 by proteasome mediated degradation | 0.00019564 |
| Regulation of Apoptosis | 0.00019564 |
| CDK-mediated phosphorylation and removal of Cdc6 | 0.00019564 |
| p53-Independent DNA Damage Response | 0.00019564 |
| Stabilization of p53 | 0.00019564 |
| Ubiquitin-dependent degradation of Cyclin D | 0.00019564 |
| Regulation of ornithine decarboxylase (ODC) | 0.00019564 |
| Ubiquitin Mediated Degradation of Phosphorylated Cdc25A | 0.00019564 |
| p53-Independent G1/S DNA damage checkpoint | 0.00019564 |
| Programmed Cell Death | 0.00019564 |
| Vif-mediated degradation of APOBEC3G | 0.00021794 |
| degradation of AXIN | 0.00023347 |
| SCF-beta-TrCP mediated degradation of Emi1 | 0.00023347 |
| Apoptosis | 0.00024085 |
| degradation of DVL | 0.0002789 |
| SCF(Skp2)-mediated degradation of p27/p21 | 0.0002789 |
| p53-Dependent G1 DNA Damage Response | 0.00030002 |
| p53-Dependent Gl/S DNA damage checkpoint | 0.00030002 |
| CDT1 association with the CDC6:ORC:origin complex | 0.00033297 |
| Degradation of GLI2 by the proteasome | 0.00033904 |
| GLI3 is processed to GLI3R by the proteasome | 0.00033904 |
| Degradation of GLI1 by the proteasome | 0.00033904 |
| Antigen Presentation: Folding, assembly and peptide loading of class I MHC | 0.00033904 |
| G1/S DNA Damage Checkpoints | 0.00036634 |
| Autodegradation of Cdh1 by Cdh1:APC/C | 0.00036634 |
| Asymmetric localization of PCP proteins | 0.00052044 |
| Cytokine Signaling in Immune system | 0.00052735 |
| AMER1 mutants destabilize the destruction complex | 0.00052735 |
| Host Interactions of HIV factors | 0.00052735 |
| Degradation of beta-catenin by the destruction complex | 0.00052735 |
| phosphorylation site mutants of CTNNB1 are not targeted to the proteasome by the destruction complex | 0.00052735 |

TABLE 23-continued

| Pathway | FDR |
| --- | --- |
| S33 mutants of beta-catenin aren't phosphorylated | 0.00052735 |
| truncated APC mutants destabilize the destruction complex | 0.00052735 |
| deletions in the AXIN genes in hepatocellular carcinoma result in elevated WNT signaling | 0.00052735 |
| APC/C:Cdc20 mediated degradation of Securin | 0.00052735 |
| deletions in the AMER1 gene destabilize the destruction complex | 0.00052735 |
| Activation of NF-kappaB in B cells | 0.00052735 |
| T41 mutants of beta-catenin aren't phosphorylated | 0.00052735 |
| Assembly of the pre-replicative complex | 0.00052735 |
| Cyclin E associated events during Gl/S transition | 0.00052735 |
| Cyclin A:Cdk2-associated events at S phase entry | 0.00052735 |
| AXIN mutants destabilize the destruction complex, activating WNT signaling | 0.00052735 |
| APC truncation mutants have impaired AXIN binding | 0.00052735 |
| misspliced GSK3beta mutants stabilize beta-catenin | 0.00052735 |
| truncations of AMER1 destabilize the destruction complex | 0.00052735 |
| APC truncation mutants are not K63 polyubiquitinated | 0.00052735 |
| TCF7L2 mutants don't bind CTBP | 0.00052735 |
| S45 mutants of beta-catenin aren't phosphorylated | 0.00052735 |
| S37 mutants of beta-catenin aren't phosphorylated | 0.00052735 |
| AXIN missense mutants destabilize the destruction complex | 0.00052735 |
| Cdc20:Phospho-APC/C mediated degradation of Cyclin A | 0.00063305 |
| APC/C:Cdh1 mediated degradation of Cdc20 and other APC/C:Cdh1 targeted proteins in late mitosis/early G1 | 0.00063305 |
| Orc1 removal from chromatin | 0.00067558 |
| Switching of origins to a post-replicative state | 0.00067558 |
| APC:Cdc20 mediated degradation of cell cycle proteins prior to satisfaction of the cell cycle checkpoint | 0.00067558 |
| Regulation of mRNA stability by proteins that bind AU-rich elements | 0.00071424 |
| Translocation of ZAP-70 to Immunological synapse | 0.00077576 |
| Removal of licensing factors from origins | 0.00079073 |
| APC/C:Cdc20 mediated degradation of mitotic proteins | 0.00079073 |
| Activation of APC/C and APC/C:Cdc20 mediated degradation of mitotic proteins | 0.00086583 |
| PCP/CE pathway | 0.00104426 |
| Regulation of DNA replication | 0.00104426 |
| Phosphorylation of CD3 and TCR zeta chains | 0.00109603 |
| Regulation of APC/C activators between G1/S and early anaphase | 0.00122728 |
| Antigen processing: Ubiquitination & Proteasome degradation | 0.00165974 |
| M/G1 Transition | 0.00186599 |
| DNA Replication Pre-Initiation | 0.00186599 |
| PD-1 signaling | 0.00186599 |
| Regulation of mitotic cell cycle | 0.00199262 |
| APC/C-mediated degradation of cell cycle proteins | 0.00199262 |
| Hedgehog 'on' state | 0.00234744 |
| beta-catenin independent WNT signaling | 0.00307868 |
| Post-translational protein modification | 0.0045083 |
| Synthesis of DNA | 0.00577858 |
| Hedgehog 'off' state | 0.00577858 |
| Defective ALG14 causes congenital myasthenic syndrome (ALG14-CMS) | 0.00577858 |
| Defective DPAGT1 causes DPAGT1-CDG (CDG-1j) and CMSTA2 | 0.00577858 |
| Defective ALG1 causes ALG1-CDG (CDG-1k) | 0.00577858 |
| Diseases associated with N-glycosylation of proteins | 0.00577858 |
| Defective MGAT2 causes MGAT2-CDG (CDG-2a) | 0.00577858 |
| Asparagine N-linked glycosylation | 0.00577858 |
| Defective ALG8 causes ALG8-CDG (CDG-1h) | 0.00577858 |
| Defective ALG3 causes ALG3-CDG (CDG-1d) | 0.00577858 |
| Defective MAN1B1 causes MRT15 | 0.00577858 |
| Defective RFT1 causes RFT1-CDG (CDG-1n) | 0.00577858 |
| Defective MUGS causes MOGS-CDG (CDG-2b) | 0.00577858 |
| Defective ALG12 causes ALG12-CDG (CDG-1g) | 0.00577858 |
| Defective ALG11 causes ALG11-CDG (CDG-1p) | 0.00577858 |
| Defective MPDU1 causes MPDUl-CDG (CDG-1f) | 0.00577858 |
| Defective ALG6 causes ALG6-CDG (CDG-1c) | 0.00577858 |
| Defective ALG2 causes ALG2-CDG (CDG-1i) | 0.00577858 |
| Defective ALG9 causes ALG9-CDG (CDG-1l) | 0.00577858 |
| Generation of second messenger molecules | 0.00577858 |

TABLE 23-continued

| Pathway | FDR |
| --- | --- |
| Cytosolic tRNA aminoacylation | 0.00716219 |
| DNA Replication | 0.00836342 |
| Metabolism of amino acids and derivatives | 0.009109 |
| Costimulation by the CD28 family | 0.0094808 |
| G1/S Transition | 0.0105585 |
| HIV Infection | 0.01259271 |
| Downstream TCR signaling | 0.01527904 |
| Signaling by Hedgehog | 0.0155106 |
| Cell Cycle Checkpoints | 0.01753312 |
| O-linked glycosylation of mucins | 0.02063405 |
| S Phase | 0.02401362 |
| Downstream signaling events of B Cell Receptor (BCR) | 0.02749436 |
| Mitotic G1-G1/S phases | 0.04108854 |
| Separation of Sister Chromatids | 0.04827289 |

TABLE 24

| Term | FDR |
| --- | --- |
| response to magnesium ion (GO:0032026) | 0.01178146 |
| positive regulation of release of sequestered calcium ion into cytosol (GO:0051281) | 0.01178146 |
| potassium ion transport (GO:0006813) | 0.01178146 |
| cellular potassium ion transport (GO:0071804) | 0.01178146 |
| potassium ion transmembrane transport (GO:0071805) | 0.01178146 |
| regulation of endocytosis (GO:0030100) | 0.01247912 |
| positive regulation of calcium ion transport into cytosol (GO:0010524) | 0.01909394 |
| regulation of release of sequestered calcium ion into cytosol (GO:0051279) | 0.03574339 |
| regulation of vesicle-mediated transport (GO:0060627) | 0.04808581 |
| regulation of calcium ion transport into cytosol (GO:0010522) | 0.04808581 |

REFERENCES

1. Adachi, et al., "Correlation of KAI1/CD82 gene expression with good prognosis in patients with non-small cell lung cancer. *Cancer Res.* 1996; 56(8):1751-1755.

2. Agresti A. "Categorical Data Analysis." New York: Wiley. 1990:350-354.

3. Bach, et al., "Benefits and Harms of CT Screening for Lung Cancer." *JAMA* 2012, 307(22): 2418-2429.

4. Beane, et al., "Reversible and permanent effects of tobacco smoke exposure on airway epithelial gene expression." *Genome Biology* 2007 8:R201.

5. Beane, et al., "A prediction model for diagnosing lung cancer that integrates genomic and clinical features." *Cancer Prevention Research* 2008.

6. Blomquist, et al., "Pattern of antioxidant and DNA repair gene expression in normal airway epithelium associated with lung cancer diagnosis." *Cancer Res.* 2009; 69(22): 8629-8635.

7. Chari, et al., "Effect of active smoking on the human bronchial epithelium transcriptome." *BMC Genomics* 2007, 8:297.

8. Chen, et al., "Enrichr: interactive and collaborative HTMLS gene list enrichment analysis tool." *BMC Bioinformatics* 2013, 14:128.

9. DeLong, et al., "Comparing the areas under two or more correlated receiver operating characteristic curves: A nonparametric approach." *Biometrics.* 1988; 44(3):837-845.

10. Dong, et al., "KAI1, a metastasis suppressor gene for prostate cancer on human chromosome 11p11.2". *Science.* 1995; 268(5212):884-886.

11. Edge, et al., "The American Joint Committee on Cancer: The 7$^{th}$ edition of the AJCC Cancer Staging Manual and the future of TNM." *Ann Surg Oncol.* 2010; 17:1471.

12. Gould, et al., "A Clinical Model To Estimate the Pretest Probability of Lung Cancer in Patients With Solitary Pulmonary Nodules." *Chest* 2007, 131(2): 383-388.

13. Gould, et al., "Recent Trends in the Identification of Incidental Pulmonary Nodules." *Am J Respir Crit Care Med.* 2015, 192(10): 1208-1214.

14. Gu, et al., "Down-regulation of miR-150 induces cell proliferation inhibition and apoptosis in non-small-cell lung cancer by targeting BAK1 in vitro." *Tumor Biol.* 2014; 35(6):5287-5293.

15. Irizarry, et al. "Exploration, normalization, and summaries of high density oligonucleotide array probe level data." *Biostat Oxf Engl.* 2003; 4(2):249-264.

16. Johnson, et al. "Adjusting batch effects in microarray expression data using empirical Bayes methods." *Biostatistics.* 2007; 8(1):118-127.

17. Kauffmann et al., "arrayQualityMetrics—a bioconductor package for quality assessment of microarray data." *Bioinforma Oxf Engl.* 2009; 25(3):415-416.

18. Leisenring W, et al., "Comparisons of predictive values of binary medical diagnostic tests for paired designs." *Biometrics* 2000; 56(2):345-351.

19. Lewis, et al., "Cotinine levels and self-reported smoking status in patients attending a bronchoscopy clinic." *Biomarkers* 2003, 8: 3-4.

20. Lochhead, et al., "Etiologic field effect: Reappraisal of the field effect concept in cancer predisposition and progression." *Mod Pathol.* 2015; 28(1):14-29.

21. Majhi, et al., "Pathobiological implications of MUC4 in non-small-cell lung cancer." *J Thorac Oncol Off Publ Int Assoc Study Lung Cancer.* 2013; 8(4):398-407.

22. Morales, et al., "Accuracy of self-reported tobacco use in newly diagnosed cancer patients." *Cancer Causes Control* 2013, 24(6):1223-30.

23. Ost, et al., "Diagnostic yield and complications of bronchoscopy for peripheral lung lesions. Results of the AQuIRE registry." *Am J Respir Crit Care Med.* 2015; 193(1): 68-77.

24. Rivera, et al., "Establishing the diagnosis of lung cancer: Diagnosis and management of lung cancer, 3rd ed.: American College of Chest Physicians evidence-based clinical practice guidelines." *Chest.* 2013; 143(5 suppl): e142S-e165S.

25. Rosell, et al., "Genetics and biomarkers in personalization of lung cancer treatment," *The Lancet.* 2013; 382 (9893):720-731.

26. Silvestri, et al., "A bronchial genomic classifier for the diagnostic evaluation of lung cancer." *N. Engl. J Med.* 2015, 373: 243-251.

27. Singhal, et al., "Gene expression profiling of nonsmall cell lung cancer." *Lung Cancer.* 2008; 60(3):313-324.

28. Smyth, G K. "limma: Linear models for microarray data." In: R Gentleman, V J Carey, W Huber, R A Irizarry, S Dudoit, eds. Bioinformatics and Computational Biology Solutions Using R and Bioconductor. Statistics for Biology and Health. New York: Springer; 2005:397-420.

29. Spira, et al., "Airway epithelial gene expression in the diagnostic evaluation of smokers with suspect lung cancer." *Nature Medicine,* 2007.

30. Subramanian, et al., "Gene set enrichment analysis: A knowledge-based approach for interpreting genome-wide expression profiles." *Proc Natl Acad Sci USA.* 2005; 102(43): 15545-15550.

31. The National Lung Screening Trial Research Team (NLST), "Reduced Lung-Cancer Mortality with Low-Dose Computed Tomographic Screening." *N. Engl J Med,* 2011, 365: 395-409.

32. Tanner, et al., "Management of pulmonary nodules by community pulmonologists: A multicenter observational study." *Chest.* 2015; 148(6):1405-1414.

33. Tukey, et al., "Population-based estimates of transbronchial lung biopsy utilization and complications." *Respir Med.* 2012; 106(11):1559-65.

34. Wang, et al., "ST14 (suppression of tumorigenicity 14) gene is a target for miR-27b, and the inhibitory effect of ST14 on cell growth is independent of miR-27b regulation." *J Biol Chem.* 2009; 284(34):23094-23106.

35. Weiner, et al., "Population-based risk for complications after transthoracic needle lung biopsy of a pulmonary nodule: an analysis of discharge records." *Ann Intern Med.* 2011, 155(3): 137-44.

36. Weiner, et al., "An Official American Thoracic Society/American College of Chest Physicians Policy Statement: Implementation of Low-Dose Computed Tomography Lung Cancer Screening Programs in Clinical Practice." *American Journal of Respiratory and Critical Care Medicine* 2015, 192(7): 881-891.

37. Wiener, et al., "Resource use and guideline concordance in evaluation of pulmonary nodules for cancer: Too much and too little care." *JAMA Intern Med.* 2014; 174(6): 871-880.

38. Whitney, et al., "Derivation of a bronchial genomic classifier for lung cancer in a prospective study of patients undergoing diagnostic bronchoscopy." *BMC Medical Genomics* 2015, 8:18.

39. Zhang, et al., "Similarity and differences in effect of cigarette smoking on gene expression in nasal and bronchial epithelium." *Physiological Genomics* 2010; 41(1): 1-8.

What is claimed is:

1. A method, comprising:

(a) performing a diagnostic procedure on a subject to determine a risk of malignancy for a subject for having or developing lung cancer, wherein said diagnostic procedure comprises a computer-aided tomography, a chest X-ray, or a bronchoscopy, and wherein said diagnostic procedure provides an indeterminate result for lung cancer;

(b) responsive to said indeterminate result for lung cancer, obtaining a nasal epithelial sample of said subject;

(c) generating a data set comprising (i) one or more genomic features in said nasal epithelial sample of said subject and (ii) one or more clinical features of said subject, wherein generating said data set comprises sequencing ribonucleic acid (RNA) molecules derived from said nasal epithelial sample to determine said one or more genomic features, wherein said one or more genomic features comprise genomic markers that are differentially expressed in nasal epithelium of subjects with lung cancer as compared to subjects without lung cancer;

(d) in a programmed computer, using a classifier to process said data set comprising said one or more genomic features and said one or more clinical features, to determine whether said subject has an increased risk of having or developing said lung cancer; and (e) responsive to said determining in (d), administering to said subject a therapeutic intervention for lung cancer, wherein said therapeutic intervention comprises chemotherapy, radiation therapy, immunotherapy, surgical resection, or a combination thereof.

2. The method of claim 1, wherein said one or more genomic features comprise a genomic marker indicative of smoking status.

3. The method of claim 2, wherein said genomic marker indicative of smoking status is determined based at least in part on expression products of genes differentially expressed in current smokers and former smokers.

4. The method of claim 1, wherein said one or more genomic features comprise a genomic marker indicative of time since quitting smoking.

5. The method of claim 1, wherein said subject has lung nodules that are inconclusive for lung cancer as determined by computer aided tomography scan or bronchoscopy.

6. The method of claim 1, wherein said nasal epithelial sample comprises nasal epithelial cells.

7. The method of claim 1, further comprising obtaining said nasal epithelial sample from said subject by brushing.

8. The method of claim 1, wherein said subject has a lung nodule or lesion greater than 3 centimeters.

9. The method of claim 1, wherein said subject has a lung nodule or lesion less than 3 centimeters.

10. The method of claim 1, wherein said one or more clinical features are selected from the group consisting of: age, nodule or lesion size, nodule or lesion location, and any combination thereof.

11. The method of claim 1, wherein said one or more genomic features comprise gene expression products of said nasal epithelial sample obtained from said subject.

12. The method of claim 1, wherein said classifier uses a trained algorithm.

13. The method of claim 12, wherein said trained algorithm has been trained with a training data set comprising sequence information derived from transcripts of bronchial epithelial cells.

14. The method of claim 12, wherein said trained algorithm has been trained with a training data set comprising sequence information derived from transcripts of nasal epithelial cells.

15. The method of claim 1, wherein said data set further comprises a ribonucleic acid (RNA) integrity number.

16. The method of claim 1, wherein said lung cancer is selected from the group consisting of adenocarcinoma, squamous cell carcinoma, small cell cancer, and non-small cell cancer.

17. The method of claim 1, wherein said diagnostic procedure comprises said computer-aided tomography.

18. The method of claim 1, wherein said diagnostic procedure comprises said chest X-ray.

19. The method of claim 1, wherein said diagnostic procedure comprises said bronchoscopy.

20. The method of claim 1, wherein said therapeutic intervention comprises said chemotherapy.

21. The method of claim 1, wherein said therapeutic intervention comprises said radiation therapy.

22. The method of claim 1, wherein said therapeutic intervention comprises said immunotherapy.

23. The method of claim 1, wherein said therapeutic intervention comprises said surgical resection.

\*　\*　\*　\*　\*